United States Patent
Boctor et al.

(10) Patent No.: US 10,349,917 B2
(45) Date of Patent: Jul. 16, 2019

(54) SYNTHETIC APERTURE ULTRASOUND SYSTEM

(71) Applicants: The Johns Hopkins University, Baltimore, MD (US); Duke University, Durham, NC (US)

(72) Inventors: Emad M. Boctor, Baltimore, MD (US); Gregg Trahey, Durham, NC (US); Nick Bottenus, Durham, NC (US); Haichong Zhang, Baltimore, MD (US)

(73) Assignees: The Johns Hopkins University, Baltimore, MD (US); Duke University, Durham, NC (US)

( * ) Notice: Subject to any disclaimer, the term of this patent is extended or adjusted under 35 U.S.C. 154(b) by 859 days.

(21) Appl. No.: 14/737,318

(22) Filed: Jun. 11, 2015

(65) Prior Publication Data
US 2015/0359512 A1 Dec. 17, 2015

Related U.S. Application Data

(60) Provisional application No. 62/010,808, filed on Jun. 11, 2014.

(51) Int. Cl.
*A61B 8/00* (2006.01)
*A61B 8/14* (2006.01)
(Continued)

(52) U.S. Cl.
CPC ............ *A61B 8/4263* (2013.01); *A61B 8/145* (2013.01); *A61B 8/4416* (2013.01);
(Continued)

(58) Field of Classification Search
CPC ..... A61B 8/4263; A61B 8/145; A61B 8/4416; A61B 8/4477
See application file for complete search history.

(56) References Cited

U.S. PATENT DOCUMENTS

| 4,277,367 A | 7/1981 | Madsen et al. |
| 5,538,004 A * | 7/1996 | Bamber ............. G01S 7/52044 128/916 |

(Continued)

FOREIGN PATENT DOCUMENTS

| KR | 2014-0012043 A | 1/2014 |
| WO | WO-99/30617 A1 | 6/1999 |

OTHER PUBLICATIONS

Aalamifar et al (2015) Co-robotic ultrasound tomography: dual arm setup and error analysis. SPIE Medical Imaging 94190N-94190N-9.
(Continued)

*Primary Examiner* — Joseph M Santos Rodriguez
(74) *Attorney, Agent, or Firm* — Harrity & Harrity, LLP

(57) ABSTRACT

A synthetic aperture ultrasound system includes an ultrasound probe, and an ultrasound signal processor configured to communicate with the ultrasound probe to receive phase and amplitude information from a plurality of ultrasonic echo signals from a corresponding plurality of ultrasound pulses. The synthetic aperture ultrasound system also includes a positioning system configured to communicate with the ultrasound signal processor to provide probe position information. The positioning system is configured to determine a first position and a second position of the ultrasound probe relative to a region of interest. The ultrasound signal processor is further configured to coherently sum, utilizing the probe position information, at least one of the plurality of ultrasonic echo signals from the first position with at least one of the plurality of ultrasonic echo signals from the second position to provide a synthetic aperture that is larger than a physical aperture of the ultrasound probe.

20 Claims, 34 Drawing Sheets

(51) Int. Cl.
  A61B 8/08   (2006.01)
  G01S 15/89  (2006.01)
  A61B 34/30  (2016.01)
(52) U.S. Cl.
  CPC .......... *A61B 8/4461* (2013.01); *A61B 8/4477* (2013.01); *A61B 8/4494* (2013.01); *A61B 8/461* (2013.01); *A61B 8/469* (2013.01); *A61B 8/52* (2013.01); *G01S 15/8936* (2013.01); *G01S 15/8997* (2013.01); *A61B 34/30* (2016.02); *G01S 15/8927* (2013.01)

(56) References Cited

U.S. PATENT DOCUMENTS

| | | | |
|---|---|---|---|
| 5,951,479 | A | 9/1999 | Holm et al. |
| 6,432,054 | B1 | 8/2002 | Ustuner et al. |
| 2002/0138004 | A1 | 9/2002 | Dickey et al. |
| 2007/0161899 | A1 | 7/2007 | Barnes et al. |
| 2011/0172538 | A1* | 7/2011 | Sumi ................ A61B 8/06 600/453 |
| 2012/0044785 | A1* | 2/2012 | Yoda ................ G01S 7/52046 367/92 |

OTHER PUBLICATIONS

Ackerman et al (2014) Online Ultrasound Sensor Calibration Using Gradient Descent on the Euclidean Group. Robotics and Automation (ICRA), 2014 IEEE International Conference on.

Andresen et al (2010) Three-dimensional synthetic aperture focusing using a rocking convex array transducer. IEEE Trans Ultrason Ferroelectr Freq Control. May 2010;57(5):1051-63. doi: 10.1109/TUFFC.2010.1517.

Andresen et al (2011) Synthetic aperture focusing for a single-element transducer undergoing helical motion. IEEE Trans Ultrason Ferroelectr Freq Control. May 2011;58(5):935-43. doi: 10.1109/TUFFC.2011.1894.

Bottenus et al (2013) A synthetic aperture study of aperture size in the presence of noise and in vivo clutter. Proc. SPIE 8675, 1-10.

Cheng et al (2014) Design and development of an ultrasound calibration phantom and system. Proc. SPIE Medical Imaging 9036-76.

Corl et al (1978) *A Digital Synthetic Focus Acoustic Imaging System for NDE. 1978 Ultrasonics Symposium*, 263-268.

Durgin et al (1992) Large aperture phase error measurement and effects. IEEE Transactions on Ultrasonics, Ferroelectrics and Frequency Control 51(5).

Flax et al (1988) Phase-aberration correction using signals from point reflectors and diffuse scatterers: basic principles. IEEE Trans Ultrason Ferroelectr Freq Control. 1988;35(6):758-67.

Frazier et al (1998) Synthetic Aperture Techniques with a Virtual Source Element. Ultrasonics, Ferroelectrics, and Frequency Control, IEEE Transactions on, 45(1):196-207.

Gammelmark et al (2014) 2-D tissue motion compensation of synthetic transmit aperture images. IEEE Transactions on Ultrasonics, Ferroelectrics, and Frequency Control 61(4):594-610.

Greenleaf et al (1974) Algebraic reconstruction of spatial distributions of acoustic absorption within tissue from their two-dimensional acoustic projections. Acoustical Holography 5:591-603.

Guo et al (2014) Active echo: a new paradigm for ultrasound calibration. Medical Imaging Computing & Computer Assisted Interventions Conference 2014.

Guo et al (2014) Photoacoustic Active Ultrasound Element for Catheter Tracking. Proc. SPIE Photonics West, BiOS 89435M.

Hansen et al (2011) Introduction to Synthetic Aperture Sonar, InTech 2011.

Hansen et al (2012) Compounding in synthetic aperture imaging. IEEE Trans Ultrason Ferroelectr Freq Control. Sep. 2012;59(9):2054-65.

Harris et al (2010) Speckle tracking in a phantom and feature-based tracking in liver in the presence of respiratory motion using 4D ultrasound. Phys Med Biol. Jun. 21, 2010;55(12):3363-80. doi: 10.1088/0031-9155/55/12/007. Epub May 26, 2010.

Holmes et al (1955) The Ultrasonic Visualization of Soft Tissue Structures in the Human Body. Trans Am Clin Climatol Assoc. 1955; 66: 208-225.

Huang et al (2004) Aperture size effect on ultrasonic wavefront distortion correction. IEEE Trans Ultrason Ferroelectr Freq Control. May 2004;51(5):589-605.

Jensen et al (1992) Calculation of Pressure Fields from Arbitrarily Shaped, Apodized, and Excited Ultrasound Transducers. IEEE Transactions on Ultrasonics, Ferroelectrics, and Frequency Control 39(2): 262-267.

Jensen et al (1996) Field: A Program for Simulating Ultrasound Systems. Medical & Biological Engineering & Computing 34, Suppl. 1 Part 1 pp. 351-343.

Jensen et al (2006) Synthetic aperture ultrasound imaging. Ultrasonics 44:e5-e15.

Johnson et al (2005) Coherent-array imaging using phased subarrays. Part I: basic principles. IEEE Transactions on Ultrasonics, Ferroelectrics, and Frequency Control 52(1):37-50.

Karaman et al (1995) Synthetic aperture imaging for small scale systems. IEEE Trans. Ultrason. Ferroelect. Freq. Cont. 42:429-442.

Kortbek et al (2013) Sequential beamforming for synthetic aperture imaging. Ultrasonics 53(1):1-16.

Liu et al (1998) Estimation and correction of ultrasonic wavefront distortion using pulse-echo data received in a two-dimensional aperture. IEEE Trans Ultrason Ferroelectr Freq Control. 1998;45(2):473-90. doi: 10.1109/58.660157.

Lockwood et al (1998) Real-time 3-D ultrasound imaging using sparse synthetic aperture beamforming. IEEE Trans Ultrason Ferroelectr Freq Control. 1998;45(4):980-8. doi: 10.1109/58.710573.

Mercier et al (2005) A review of calibration techniques for freehand 3-D ultrasound systems. Ultrasound Med Biol. Apr. 2005;31(4):449-71.

Mitra et al (2004) Registration of point cloud data from a geometric optimization perspective. Symposium on Geometry Processing 2004.

Moshfeghi et al (1988) In vivo and in vitro ultrasound beam distortion measurements of a large aperture and a conventional aperture focussed transducer. Ultrasound Med Biol. 1988;14(5):415-28.

Nikolov et al (2002) Three-dimensional real-time synthetic aperture imaging using a rotating phased array transducer. 2002 IEEE Ultrasonics Symposium 1585-1588.

Nikolov et al (2002) Virtual ultrasound sources in high-resolution ultrasound imaging. Proc. SPIE 487:395-405.

Nock et al (1989) Phase aberration correction in medical ultrasound using speckle brightness as a quality factor. J Acoust Soc Am. May 1989;85(5):1819-33.

Shattuck et al (1982) Compound scanning with a phased array. Ultrasonic Imaging 4:93-107.

Smith et al (1983) Low contrast detectability and contrast/detail analysis in medical ultrasound. IEEE Transactions on Sonics and Ultrasonics 3(3):164-173.

Stepinski et al (2010) Synthetic aperture focusing techniques for ultrasonic imaging of solid objects. Synthetic Aperture Radar (EUSAR) 2010.

Trahey et al (1992) Synthetic receive aperture imaging with phase correction for motion and for tissue inhomogeneities. II. Effects of and correction for motion. IEEE Trans. Ultrason. Ferroelect. Freq. Cont. 39:496-501.

Treece et al (2003) High-definition freehand 3-D ultrasound. Ultrasound Med Biol. Apr. 2003;29(4):529-46.

Weng et al (1997) US extended-field-of-view imaging technology. Radiology. Jun. 1997;203(3):877-80.

Walker et al (1998) The application of k space in pulse echo ultrasound. IEEE Trans Ultrason Ferroelectr Freq Control. 1998;45(3):541-58. doi: 10.1109/58.677599.

(56) References Cited

OTHER PUBLICATIONS

International Search Report an Written Opinion issued in PCT International Application No. PCT/US2015/035357 dated Sep. 10, 2015.

* cited by examiner

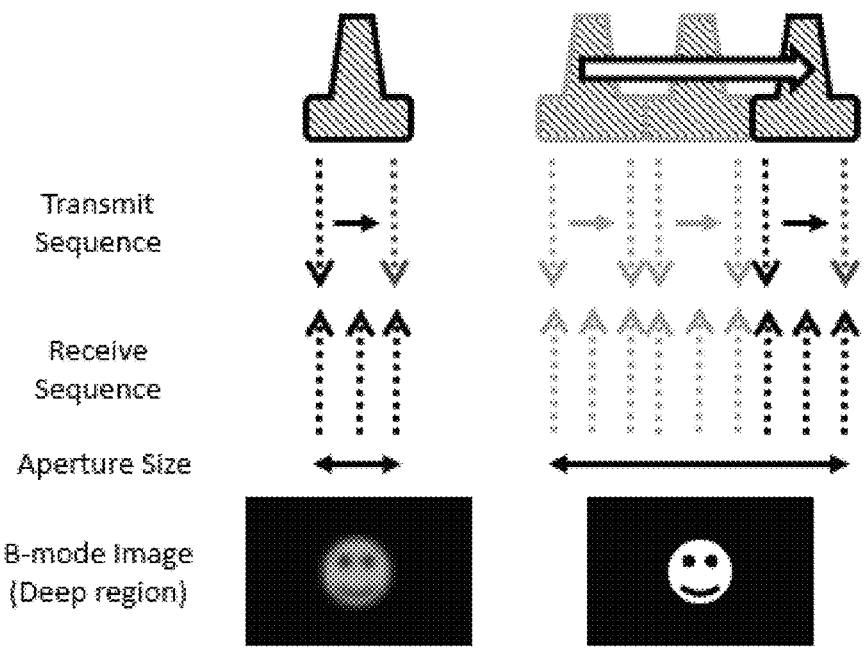
FIG. 3A
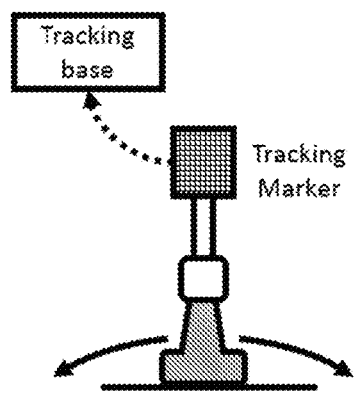
FIG. 3B

STEP 1 $\quad$ $^{USimage}p = R_i \cdot {}^{Model}p$

STEP 2 $\quad$ ${}^{Model}I_i(x,y,0) = \begin{bmatrix} 1 & 0 & 0 \\ 0 & 1 & 0 \\ 0 & 0 & 0 \end{bmatrix} \cdot {}^{Model}I_i(x,y,z).$ $\Delta t^{ij}(x,y) = {}^{Model}I_i(x,y) - {}^{Model}I_j(x,y)$ STEP 3 $\quad$ $\Delta t^{ij} = \begin{bmatrix} x \\ y \\ z \end{bmatrix}$ $^A R^{ij}\, ^X R = {}^X R\, ^B R^{ij},$ $^A R^{ij}\, ^X T + \begin{bmatrix} R_i^T(1,1)x + R_i^T(1,2)y + R_i^T(1,3)z \\ R_i^T(2,1)x + R_i^T(2,2)y + R_i^T(2,3)z \\ R_i^T(3,1)x + R_i^T(3,2)y + R_i^T(3,3)z \end{bmatrix} = {}^X R\, ^B P^{ij} + {}^X T$

SYNTHETIC APERTURE ULTRASOUND SYSTEM

This application claims priority to U.S. Provisional Application No. 62/010,808 filed Jun. 11, 2014, the entire content of which is hereby incorporated by reference.

This invention was made with Government support of Grant Nos. R01-EB017711 and T32-EB001040, awarded by the National Institutes of Health. The U.S. Government has certain rights in this invention.

BACKGROUND

1. Technical Field

The field of the currently claimed embodiments of this invention relates to ultrasound systems, and more particularly to a synthetic aperture ultrasound system.

2. Discussion of Related Art

Ultrasound imaging is used in various medical diagnoses. Resolution of the ultrasound image depends on the center frequency of transmission and the F-number determined by the imaging depth and the aperture size. Even though higher frequency transmission enables one to achieve higher resolution, high center frequency is easily absorbed in the near field due to strong attenuation, so that the contrast decreases with the increased image depth. Thus, only low frequency and low resolution are available if the region of interest is located in the far field.

Synthetic aperture is a technique to synthetize transmit and receive apertures, and utilizes wider aperture in reconstruction. Synthetic aperture is actively applied to medical ultrasound and successfully contributes to an increase in the image resolution[1-3]. Nevertheless, an ultrasound array has a fixed number of elements, so that the maximum available aperture size depends on the width of the ultrasound transducer and the number of elements on it. Therefore, it is challenging to achieve higher resolution in conventional synthetic aperture imaging since the F number becomes too high in the deeper regions. Although using large arrays is a possible solution, these require huge costs, and the flexibility for different usage requirements is low.

SUMMARY

According to some embodiments of the present invention, a synthetic aperture ultrasound system includes an ultrasound probe, and an ultrasound signal processor configured to communicate with the ultrasound probe to receive both phase and amplitude information from a plurality of ultrasonic echo signals from a corresponding plurality of transmitted ultrasound pulses. The synthetic aperture ultrasound system also includes a positioning system configured to communicate with the ultrasound signal processor to provide probe position information to the ultrasound signal processor. The positioning system is configured to determine a first position of the ultrasound probe relative to a region of interest and a second position of the ultrasound probe relative to the region of interest, the second position of the ultrasound probe being translated with respect to the first position of the ultrasound probe. The ultrasound signal processor is further configured to coherently sum, utilizing the probe position information, at least one of the plurality of ultrasonic echo signals while the ultrasound probe is in the first position with at least one of the plurality of ultrasonic echo signals while the ultrasound probe is in the second position to provide a synthetic aperture that is larger than a physical aperture of the ultrasound probe.

According to some embodiments of the present invention, a method for providing a synthetic aperture that is larger than a physical aperture of an ultrasound probe includes transmitting a plurality of ultrasound pulses, and receiving both phase and amplitude information from a plurality of ultrasonic echo signals corresponding to the plurality of ultrasound pulses. The method further includes determining a first transmission and reception position relative to a region of interest and a second transmission and reception position relative to the region of interest, the second transmission and reception position being translated with respect to the first transmission and reception position, and coherently summing, utilizing the position information, at least one of the plurality of ultrasonic echo signals received at the first transmission and reception position with at least one of the plurality of ultrasonic echo signals received at second transmission and reception position to provide the synthetic aperture.

BRIEF DESCRIPTION OF THE DRAWINGS

Further objectives and advantages will become apparent from a consideration of the description, drawings, and examples.

FIG. 3A illustrates how the tracking technique expands the aperture size for reconstruction according to an embodiment of the invention;

FIG. 3B illustrates single probe synthetic tracked aperture imaging with free-hand tracking according to some embodiments of the invention;

FIG. 4 shows mathematical steps for a first ultrasound calibration method according to some embodiments of the invention;

DETAILED DESCRIPTION

Figure 1:
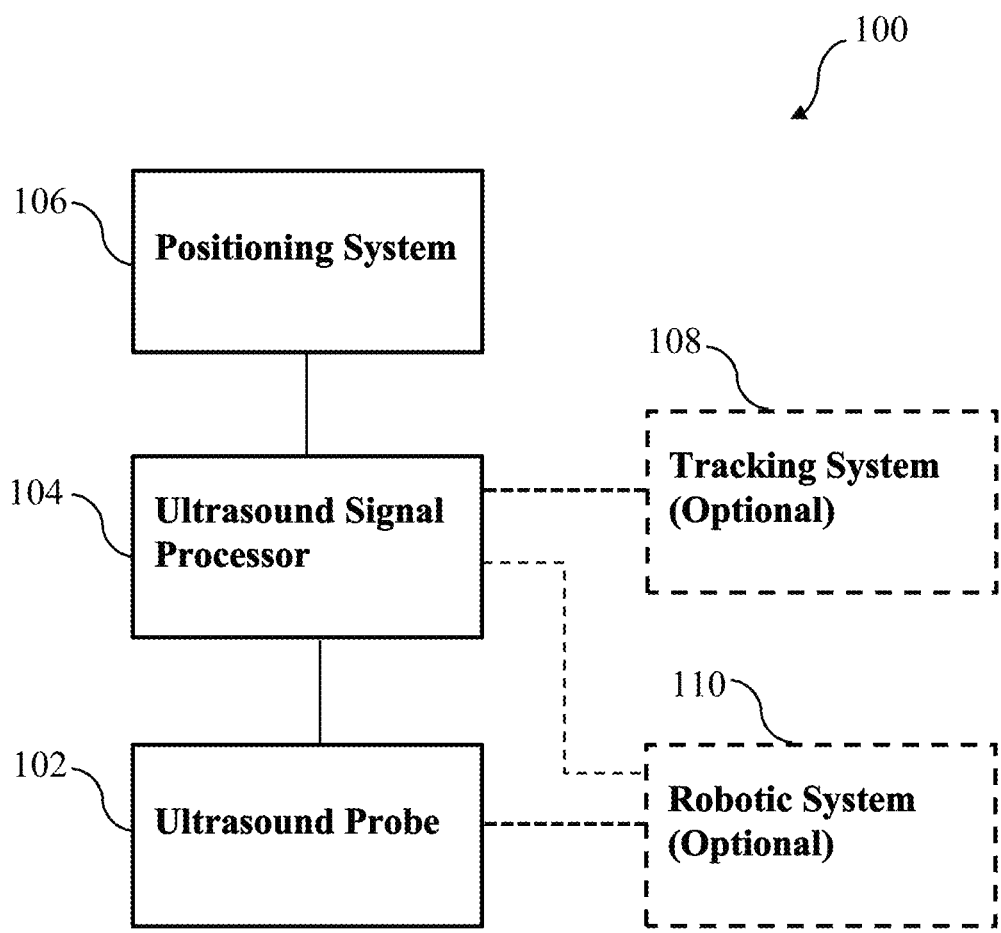
FIG. 1 is a schematic illustration of a synthetic aperture ultrasound system according to some embodiments of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

An embodiment of the current invention is directed to the combination of a high precision positioning system and an ultrasonic imaging system employing synthetic aperture methods. A synthetic aperture method is defined as any method in which ultrasonic echoes from two or more pulses are coherently summed and when those pulses are acquired with differing physical locations of all or a subset of transmit or receive element positions on the ultrasonic probe. A coherent summation is defined as the addition of raw ultrasonic echoes (either radio-frequency or I/Q as opposed to the addition of envelope-detected echoes.

As the ultrasonic probe is translated across the patient, echo data from various probe positions is coherently combined to form large effective apertures. In some embodiments, the operator can select a region of interest with a cursor or by positioning it within a pre-determined position in the image display. The operator or a robot sweeps the probe over the patient's body. If the operator controls the sweep, a position sensing system can report the position of the probe to the transmit and receive beamformers. The transmit beamformer can adaptively modify the direction, focal depth, aperture size, virtual element position, beam width, and/or other transmit parameters of subsequently fired pulses in response to array position information. The transmit beamformer can also use the array position information to steer pulses towards the region of interest.

According to some embodiments of the invention, the receive beamformer calculates the acoustic path length from an element to a voxel in the region of interest at a position of the array as the array. Across numerous array positions and for numerous transmit events, received echoes from the element are combined coherently using one of several synthetic aperture methods. If the robot executes a pre-programmed sweep, the transmit and receive beamformers can use predetermined rather than adaptive transmit and receive synthetic aperture beamforming methods. If the robot executes an adaptive sweep of the probe (potentially responding to force-feedback or the measured contours of the patient) the transmit and receive beamformers can adaptively respond to the probe position as described above. In some embodiments, a two-dimensional array is swept over the patient.

According to some embodiments, if the robot executes a pre-determined probe trajectory, the beamformer may only need a trigger signal and knowledge of the trajectory, not feedback from a positioning system. In some embodiments, if the position sensor reports a probe velocity that is greater than some pre-determined value (for example, 20 cm/s) it could automatically trigger the synthetic aperture imaging mode and turn it off once the velocity falls below a second pre-determined value. The first and second pre-determined values may be the same, or they may be different. Before and after the synthetic mode, the system may operate in normal B-mode. According to some embodiments, the position sensor generates an audio or visual signal to alert the operator as to when the sweep velocity is in the correct range for the synthetic aperture imaging mode (for example, 20-100 cm/s). The early and late probe positions in any sweep may have the most potentially compromised data. The system can include an operator control to weight or eliminate data from these positions.

FIG. 1 provides a schematic illustration of a synthetic aperture ultrasound system 100 according to some embodiments of the current invention. The synthetic aperture ultrasound system 100 includes an ultrasound probe 102, and an ultrasound signal processor 104 configured to communicate with the ultrasound probe 102 to receive both phase and amplitude information from a plurality of ultrasonic echo signals from a corresponding plurality of transmitted ultrasound pulses. The plurality of ultrasonic echo signals may be sent to the ultrasound signal processor 104 by a plurality of receive elements in the ultrasound probe 102. The synthetic aperture ultrasound system 100 further includes a positioning system 106 configured to communicate with the ultrasound signal processor 104 to provide probe position information to the ultrasound signal processor 104. The positioning system 106 is configured to determine a first position of the ultrasound probe 102 and a second position of the ultrasound probe 102, the second position of the ultrasound probe 102 being translated with respect to the first position. The ultrasound signal processor 104 is further configured to coherently sum, utilizing the probe position information, at least one of the plurality of ultrasonic echo signals while the ultrasound probe 102 is in the first position with at least one of the plurality of ultrasonic echo signals while the ultrasound probe 102 is in the second position to provide a synthetic aperture that is larger than a physical aperture of the ultrasound probe 102. The synthetic aperture ultrasound system 100 may be configured to repeatedly acquire and coherently sum ultrasonic echo signals.

According to some embodiments of the invention, the probe position information of the synthetic aperture ultrasound system 100 has an accuracy in an axial direction towards the region of interest that is at least one-quarter a wavelength of ultrasound waves of the plurality of transmitted ultrasound pulses.

According to some embodiments of the invention, the synthetic aperture ultrasound system 100 includes a tracking system 108, and the probe position information can be obtained from the tracking system 108. According to some embodiments of the invention, the ultrasound probe 102 is a hand-operable ultrasound probe.

According to some embodiments of the invention, the synthetic aperture ultrasound system 100 includes a robotic system 110 comprising a robotic arm adapted to attach to the ultrasound probe 102. The probe position information can be obtained from the robotic system 110.

According to some embodiments of the invention, a method for providing a synthetic aperture that is larger than a physical aperture of an ultrasound probe includes transmitting a plurality of ultrasound pulses, and receiving both phase and amplitude information from a plurality of ultrasonic echo signals corresponding to the plurality of ultrasound pulses. The method further includes determining a first transmission and reception position and a second transmission and reception position, the second transmission and reception position translated with respect to the first transmission and reception position. Finally, the method includes coherently summing, utilizing the position information, at least one of the plurality of ultrasonic echo signals received at the first position with at least one of the plurality of ultrasonic echo signals received at second position to provide the synthetic aperture. The method can be repeated for additional transmission and reception positions.

The following examples describe some further concepts of the invention with reference to particular examples. The general concepts of the current invention are not limited to the particular examples.

EXAMPLES

Example 1—Synthetic Aperture Ultrasound Imaging

Figure 2:
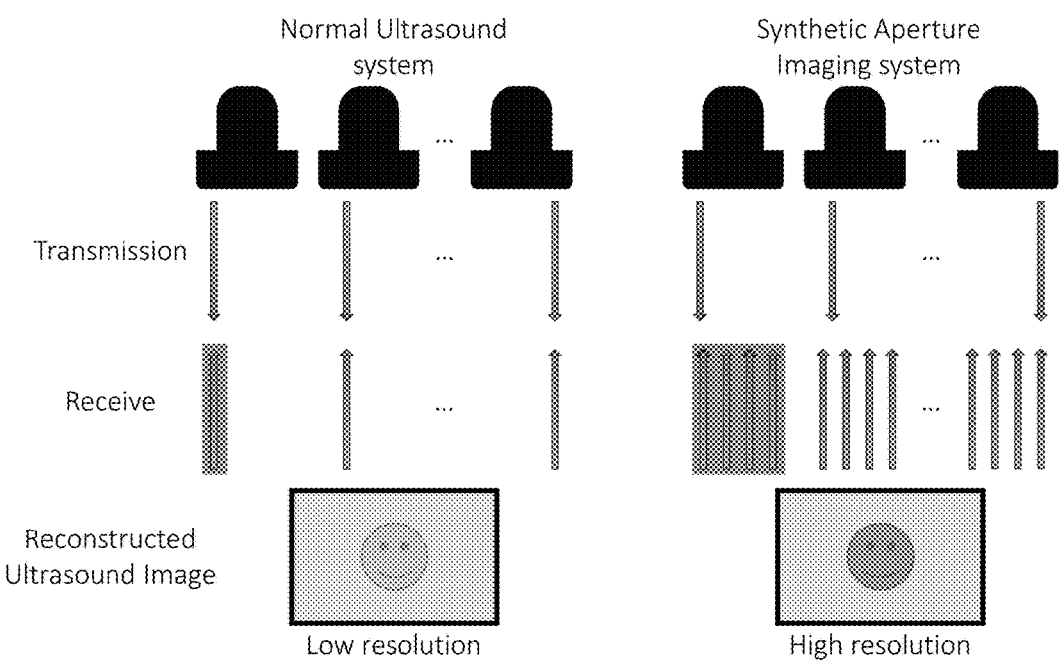
FIG. 2 illustrates a general concept of a synthetic aperture imaging system according to some embodiments of the invention.

As described above, it is challenging to achieve higher resolution in conventional synthetic aperture imaging since the F number becomes too high in the deeper regions, and large arrays require huge costs and provide little flexibility for different usage requirements. To address these problems, some embodiment of the current invention expand the size of the available aperture by utilizing a robotic system. Having the ultrasound probe held by a robot arm allows rotational motion and translational displacement, which can generate imaginary elements, and the expanded aperture can be utilized in reconstruction. Since the F number can be reduced by widening the aperture, lateral resolution improvement can be expected. Therefore, some embodiments of the current invention provide higher resolution through an extended aperture implemented by a robotically controlled transducer. FIG. 2 illustrates the general idea of a synthetic aperture imaging system.

An embodiment of the current invention combines robotic tracking techniques with synthetic aperture ultrasound imaging to achieve higher resolution images. FIG. 3A shows an example of how the tracking technique expands the aperture size for reconstruction. The left-hand image represents a conventional synthetic aperture imaging system, and the right-hand image represents the synthetic tracked aperture ultrasound imaging system according to some embodiments of the invention. An ultrasound calibration method is also provided with sub-millimeter error to enable some embodiments of the current invention.

Figures 3C, 3D:
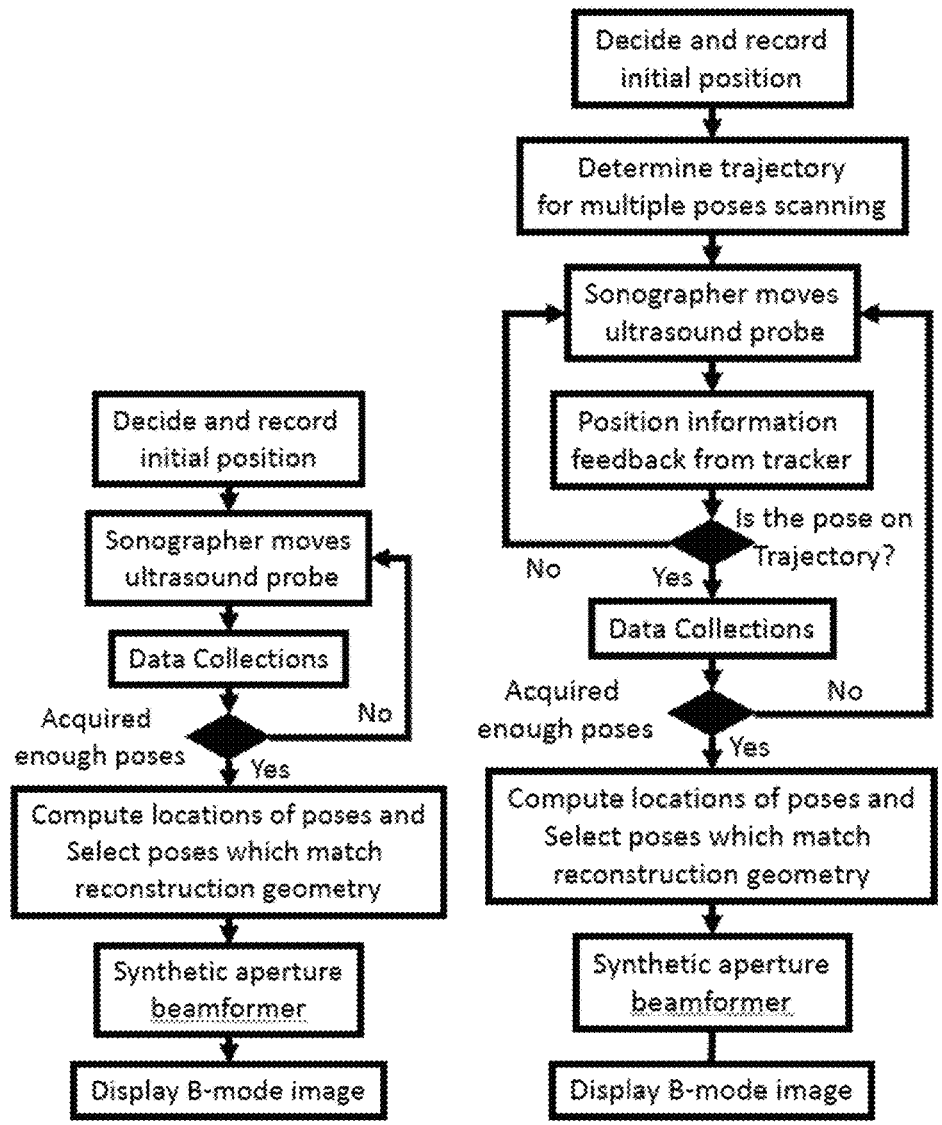
FIG. 3C illustrates freehand scanning strategies for synthetic tracked aperture ultrasound (STrAtUS) imaging using a blind scanning mode.
FIG. 3D illustrates freehand scanning strategies for synthetic tracked aperture ultrasound imaging using a guided scanning mode.

FIG. 3B illustrates single probe synthetic tracked aperture imaging with free-hand tracking according to some embodiments of the invention. FIG. 3C is a flow chart with freehand scanning strategies for synthetic tracked aperture ultrasound (STrAtUS) imaging using a blind scanning mode according to some embodiments of the invention. The positioning system is used to record the initial position of the probe. The sonographer then moves the ultrasound probe and collects data from a new position. This process is repeated until data has been collected from a sufficient number of poses. The positioning system can compute the locations of the poses, and the ultrasound signal processor can select the poses which match the reconstruction geometry. The ultrasound signal processor can the coherently sum the data from these poses to provide a synthetic aperture that is larger than a physical aperture of the ultrasound probe. The ultrasound signal processor can display the acquired B-mode image.

The determination of whether a sufficient amount of data has been collected can be based on the desired aperture size. The deeper the target depth is, the more data is needed to expand the aperture size to keep the F-number low. Moreover, the interval distance between two poses should be so small that sufficient coverage is kept in the K-space. Especially in the case of the blind scanning mode, the positioning system can trace the positioning information of the probe, and that information can be used to determine if sufficient coherent information and aperture size are acquired.

FIG. 3D is a flow chart with freehand scanning strategies for synthetic tracked aperture ultrasound imaging using a guided scanning mode according to some embodiments of the invention. The positioning system is used to record the initial position of the probe, and trajectories for multiple poses scanning are determined. The imaging depth can be a primary factor in determining the trajectory. As described above, a wider aperture is expected when the target is in a deeper region. Although the wider aperture provides higher resolution, it can also introduce factors such as motion artifacts. According to some embodiments of the invention, the sonographer can define an F-number and the ultrasound signal processor can a compute a trajectory based on that F-number. The sonographer then moves the ultrasound probe, and receives feedback from the positioning system indicating whether the probe is one the intended trajectory. The sonographer moves the probe until the positioning system indicates that the probe is on the intended trajectory, and then the probe collects data from the new position. This process is repeated until data has been collected from a sufficient number of poses. The positioning system can compute the locations of the poses, and the ultrasound signal processor can select the poses which match the reconstruction geometry. The ultrasound signal processor can the coherently sum the data from these poses to provide a synthetic aperture that is larger than a physical aperture of the ultrasound probe. The ultrasound signal processor can display the acquired B-mode image.

The performance of reconstructed synthetic aperture images depends on the accuracy of the calibrated transformation, the tracking accuracy, and the accuracy of the transformation between images and to the probe. In order to move the probe to a designated position, or to know the location of the origin of the ultrasound image, an unknown rigid-body transformation on the transducer from the sensor to the image is calibrated. The process to identify this unknown transformation is called ultrasound (US) calibration. The strategy taken to get the transformation between the tracking device and the image is to solve the hand-eye calibration problem, also known as the AX=XB problem, where A and B are relative motions connected by the unknown rigid body transformation X. B is computed from the homogeneous transformation of the robot arm, and A is computed from the transformation between each image and the phantom. The tracking accuracy can be improved using the robot and creating a new ultrasound calibration method to utilize the accurate transformation from the probe to the image.

The problem of the conventional approach based on segmentation is that the accuracy of the chosen points greatly depends on the image quality and the point spread function of the phantom. The accuracy is directly related to the range of potential applications. The accuracy of ultrasound calibration based on segmentation is about 1.5 mm, although various compensation methods are applied [1]. On the other hand, the accuracy required for synthetic aperture ultrasound imaging (SAUI) is sub-wavelength (616 μm for a 2.5 MHz transducer), which cannot be achieved with the segmentation based approach. Therefore, a more accurate calibration technique is necessary. Such an ultrasound calibration method is provided herein.

The approach according to some embodiments of the invention relies not on segmentation but instead on utilizing the trajectory of the moved phantom. While fixing the position of the ultrasound probe, the phantom is moved a designated distance in two axes in the phantom's coordinate system (x and y, for example), so that the motion appears in the ultrasound image frame in the lateral and axial directions. The amount of the displacement of a target appearing in the image is compared to the actual displacement. Compared to the segmentation method, normalized cross-correlation involves the information of the entire characteristic of the acoustic response including the shape and amplitude, and it is possible to obtain an accurate displacement of the target. At the same time, the robotic tracking system can also be implemented to further improve the accuracy of the reconstructed transformation.

Figures 3E, 3F, 3G:
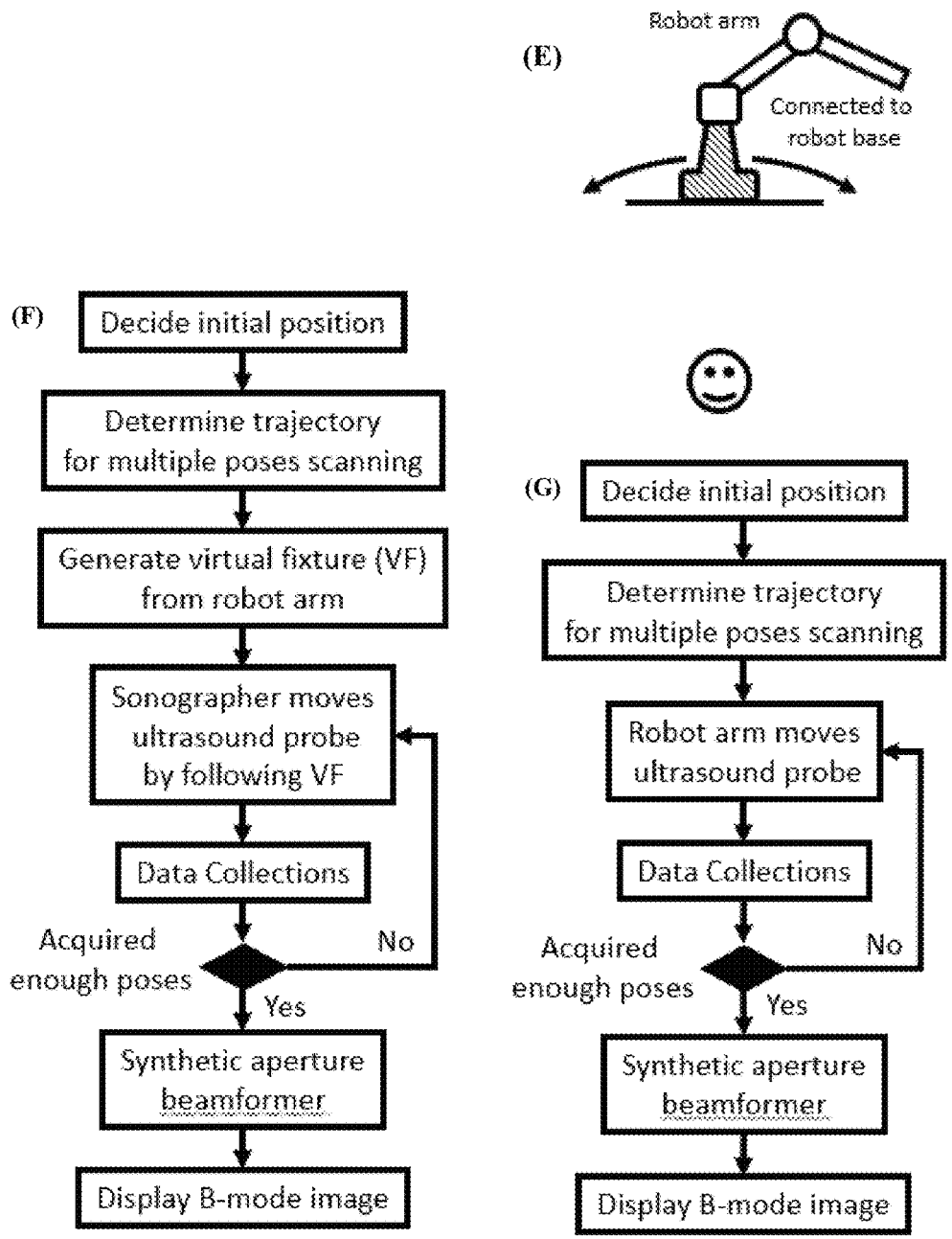
FIG. 3E illustrates single probe synthetic tracked aperture imaging with robotic tracking according to some embodiments of the invention.
FIG. 3F illustrates robotic scanning strategies for synthetic tracked aperture ultrasound imaging using a co-pilot virtual fixture approach.
FIG. 3G illustrates robotic scanning strategies for synthetic tracked aperture ultrasound imaging in an auto-pilot/autonomous scanning mode.

FIG. 3E illustrates single probe synthetic tracked aperture imaging with robotic tracking according to some embodiments of the invention. FIG. 3F is a flow chart with robotic scanning strategies for synthetic tracked aperture ultrasound imaging using a co-pilot virtual fixture approach according to some embodiments of the invention. The positioning system or a robotic tracking system is used to record the initial position of the probe. A trajectory for multiple poses scanning is then determined. A virtual fixture (VF) is generated from the robot arm. The sonographer then moves the ultrasound probe by following the VF and collects data from a new position. This process is repeated until data has been collected from a sufficient number of poses. The positioning system or robot tracking system can compute the locations of the poses, and the ultrasound signal processor can select the poses which match the reconstruction geometry. The ultrasound signal processor can the coherently sum the data from these poses to provide a synthetic aperture that is larger than a physical aperture of the ultrasound probe. The ultrasound signal processor can display the acquired B-mode image.

FIG. 3G is a flow chart with robotic scanning strategies for synthetic tracked aperture ultrasound imaging using an auto-pilot/autonomous scanning mode approach according to some embodiments of the invention. The positioning system or a robotic tracking system is used to record the initial position of the probe. A trajectory for multiple poses scanning is then determined. The robot arm then moves the ultrasound probe by following the trajectory and collects data from a new position. This process is repeated until data has been collected from a sufficient number of poses. The positioning system or robot tracking system can compute the locations of the poses, and the ultrasound signal processor can select the poses which match the reconstruction geometry. The ultrasound signal processor can the coherently sum the data from these poses to provide a synthetic aperture that is larger than a physical aperture of the ultrasound probe. The ultrasound signal processor can display the acquired B-mode image.

FIG. 4 shows the mathematical steps for calculating the transformation. STEP1 drives the rotational component of a pose. The points indicate a relative position of the phantom. Points of the model are based on the displacement of the stage, and points of the ultrasound image represent the apparent displacement calculated by the normalized cross correlation. STEP2 calculates the translational component of the relative poses. STEP3 provides the final transformation of X. Grey characters indicate unknowns, so that the equation can be solved as a least squares problem.

Quick validation of the method according to some embodiments of the current invention is conducted through simulations and experiment. In the simulations, the noise of normalized cross-correlation (NCC) was defined as 50 µm, which is the number confirmed though a preliminary experiment, and a tracking system accuracy of 100 µm was set based on the accuracy of the robot (Universal Robot, UR5) used in the experiment. The results, shown in Table 1, depict that the rotational error compared to the ground truth was 0.15±0.10 degrees and the translational error was 0.48±0.32 mm for the 60 ultrasound pose simulation.

TABLE 1

Simulation Results

| Rotation (degree) | Error from GT | STD | Translation (mm) | Error from GT | STD |
|---|---|---|---|---|---|
| Yaw | 0.092 | 0.058 | X | 0.372 | 0.261 |
| Pitch | 0.096 | 0.073 | Y | 0.210 | 0.12 |
| Roll | 0.071 | 0.04 | Z | 0.165 | 0.147 |
| Norm | 0.15 | 0.102 | Norm | 0.165 | 0.147 |

Guo et al. [2] demonstrates an interventional tool tracking and guiding technique active ultrasound pattern injection system (AUSPIS), and solves both the object visualization and mid-plane error problem at the same time. In AUSPIS, an active echo (AE) element, which acts as a miniaturized ultrasound transducer, is integrated with the target object that needs to be tracked in the ultrasound images. An electrical system composed of an ultrasound receiver, a signal processor, and a pulser is connected to the AE element. When the ultrasound system is acquiring a B-mode image, probe elements fire sequentially to scan the entire field of view (FOV). If the active echo element is in the FOV, it will sense the beacon pulse when the transmission beam scans over it. To improve the tool visualization, the AUSPIS will drive the AE element to send an ultrasound pulse immediately after the beacon signal is received. Since the reception-transmission delay is on the order of nanoseconds and is negligible for ultrasound imaging, the ultrasound pulse is superimposed on the catheter echo wave, resulting in an enhanced echo pulse with a much higher amplitude, broader frequency range, and wider emission angle. This wave travels back to the imaging probe and appears as a bright spot (AE spot) that indicates the AE element location in the B-mode image. To improve the localization accuracy along the elevation axis, AUSPIS detects the mid-plane by measuring the local ultrasound signal intensity. The beacon beam intensity from the imaging probe is highest on the mid-plane and lower on the edges. As shown in FIG. 2 of Guo et al., when the AE element is well aligned with the central plane, the received beacon signal amplitude reaches its maximum, and when it moves away the strength of beacon decreases. The reported catheter tip localization accuracy under ex vivo condition is less than 100 µm [2].

Since the AE element is a point that can be accurately localized in an ultrasound image, especially along the elevational axis, it is possible to use it in the same way as the crosswire (CW) point for ultrasound calibration. The first step is to move the ultrasound probe until the AE element is shown in the B-mode image. The second step is to finely adjust the probe position until the AE element fires active ultrasound pulses, which are an indication that the received signal amplitude exceeds the pre-selected AE response threshold. The final step is to increase the threshold and adjust the probe position at the same time, until reaching a position such that any small adjustment from this position will stop the active echo response. This step can also be done by monitoring the signal amplitude reading from the AUSPIS and finding the maximum. After this procedure, the AE element is precisely aligned with the ultrasound image mid-plane. This process may then be repeated multiple times for different ultrasound transducer orientations and positions. With the mid-plane detection feedback from AUSPIS, a more accurate and user independent position accuracy can be achieved along the elevational axis, and thus better and more consistent reconstruction precision using this method can be expected.

The approach is experimentally validated, and the result is shown in Tables 2 and 3. Comparison with the conventional CW method is conducted. Sixty crosswire point images and sixty active echo point images were collected with their respective robot poses. Two users segmented each of the two data sets a total of ten times. The ten CW data sets and the ten active echo data sets were independently used to solve for X, the transformation relating the robot end effector to the ultrasound image plane. The gradient descent solver described by Ackerman et al. [3] was used with a cost function that minimizes every pair of $B_i X p_i = B_j X p_j$. This resulted in ten Xs using the CW points and ten Xs using the active echo points. The repeatability of these ten Xs was tested using a version of the method described by Treece et al. [4]. The ultrasound image corners are transformed by each X and the standard deviations of the resulting point clouds at each corner are reported. Table 2 shows the repeatability of the Xs. For example, the norm of the standard deviations of each corner is shown in Table 2. The corners are chosen to correspond with the ultrasound image dimensions. For another experiment, all of the segmented CW points are used to test each of the active echo Xs and vice versa. Table 3 shows the best reconstruction precision of the Xs. The reconstruction precision shown is the norm of the standard deviation of the transformed test set points.

TABLE 2

Repeatability for Xs computed with segmented AE and CW points

| Type of Points | Corner (Lateral, Axial) | Repeatability |
|---|---|---|
| Active Echo | 0 mm, 0 mm | 0.37 mm |
| Active Echo | 0 mm, 90 mm | 0.60 mm |
| Active Echo | 58.5 mm, 0 mm | 0.48 mm |
| Active Echo | 58.5 mm, 90 mm | 0.71 mm |
| Crosswire | 0 mm, 0 mm | 1.66 mm |

TABLE 2-continued

Repeatability for Xs computed with segmented AE and CW points

| Type of Points | Corner (Lateral, Axial) | Repeatability |
| --- | --- | --- |
| Crosswire | 0 mm, 90 mm | 2.82 mm |
| Crosswire | 58.5 mm, 0 mm | 1.55 mm |
| Crosswire | 58.5 mm, 90 mm | 3.11 mm |

TABLE 3

Best reconstruction precision for Xs computed with segmented AE and CW points

| Type of Points | Reconstruction Precision |
| --- | --- |
| Active Echo | 1.05 mm |
| Crosswire | 2.36 mm |

In conventional diagnostic ultrasound, the number of transmission elements and receiving elements are equivalent, and transmit focusing and receive focusing using delay-and-sum reconstruction are applied. On the contrary, synthetic aperture focusing defocuses the transmission, and utilizes a wider aperture to reconstruct an A-line radio frequency signal, and full dynamic focusing is available on both the transmission and reception processes. Here, a single array element transmission and reception is considered to simplify the geometry.

In the reconstruction process, the delay applied is expressed as $$\tau = \frac{1}{c}(r_T + r_R - 2r_F), \quad (1.1)$$

where $r_T$ represents the distance from the transmission element to the focusing point, $r_R$ represents the distance from received element to the focusing point, $r_F$ represents the depth of the focusing point, and c is the speed of sound. When only one element is active for transmitting and receiving, $r_T = r_R$ stands. Therefore, the focused signal in the two dimensional image $y_F(j,i)$ is $$y_F(j, i) = \sum_{j=1}^{N} \sum_{i=1}^{M} y_R(j + \tau(j, i), i), \quad (1.2)$$

where $y_R$ is the received signal, and i and j represent the line number and sample variable, respectively.

The simulations for the robotic synthetic aperture system were conducted using Field II software which is used within Matlab® (The MathWorks Inc., Natick Mass.). Initially, the number of active elements used for both transmission and reception is set to one to simplify the analysis. In other words, the signal is transmitted and received from a single element instead of received from several elements. This cut back on the processing time during uncertainty testing since the original synthetic aperture algorithm took much longer to run and many different magnitudes of uncertainty were needed. This simplification did not have an effect on the method in principle as the changes were taken into account in the calculations.

Using Field II, simulated data was produced by designing a 64-element linear transducer array with a pitch size of 0.15 mm for both transmission and reception, which corresponds to a 9.6 mm transducer. The robot poses were simulated, and the expanded aperture size yielded 19.2 mm if the simulated probe was moved 9.6 mm in the lateral direction. Under these conditions, received signals without moving the probe had 64 lines to be reconstructed, while the expanded aperture had 128 lines. The pre-beamformed data from the expanded aperture was split from the middle to simulate different signals taken from different poses of the robot arm that moved in the lateral direction perpendicular to the ultrasound beam. The left side of the pre-beamformed data was defined as the data from the original position (P1) and the right side was regarded as the data received after displacement (P2). The transmission center frequency was set to 5 MHz, and the sampling frequency to 40 MHz based on the experimental setup. Point scatterers were designed so that each identical target was aligned in the axial direction and placed equidistantly in the axial direction (25 mm, 35 mm, 45 mm, and 55 mm) to observe the effect of imaging depth on the resolution. To imitate possible uncertainty caused by the robot movement, small displacements with a range of different magnitudes in the axial and lateral directions and in plane rotation were added to P2 before the resulting image was constructed.

Figures 5A, 5B, 5C, 5D, 5E:
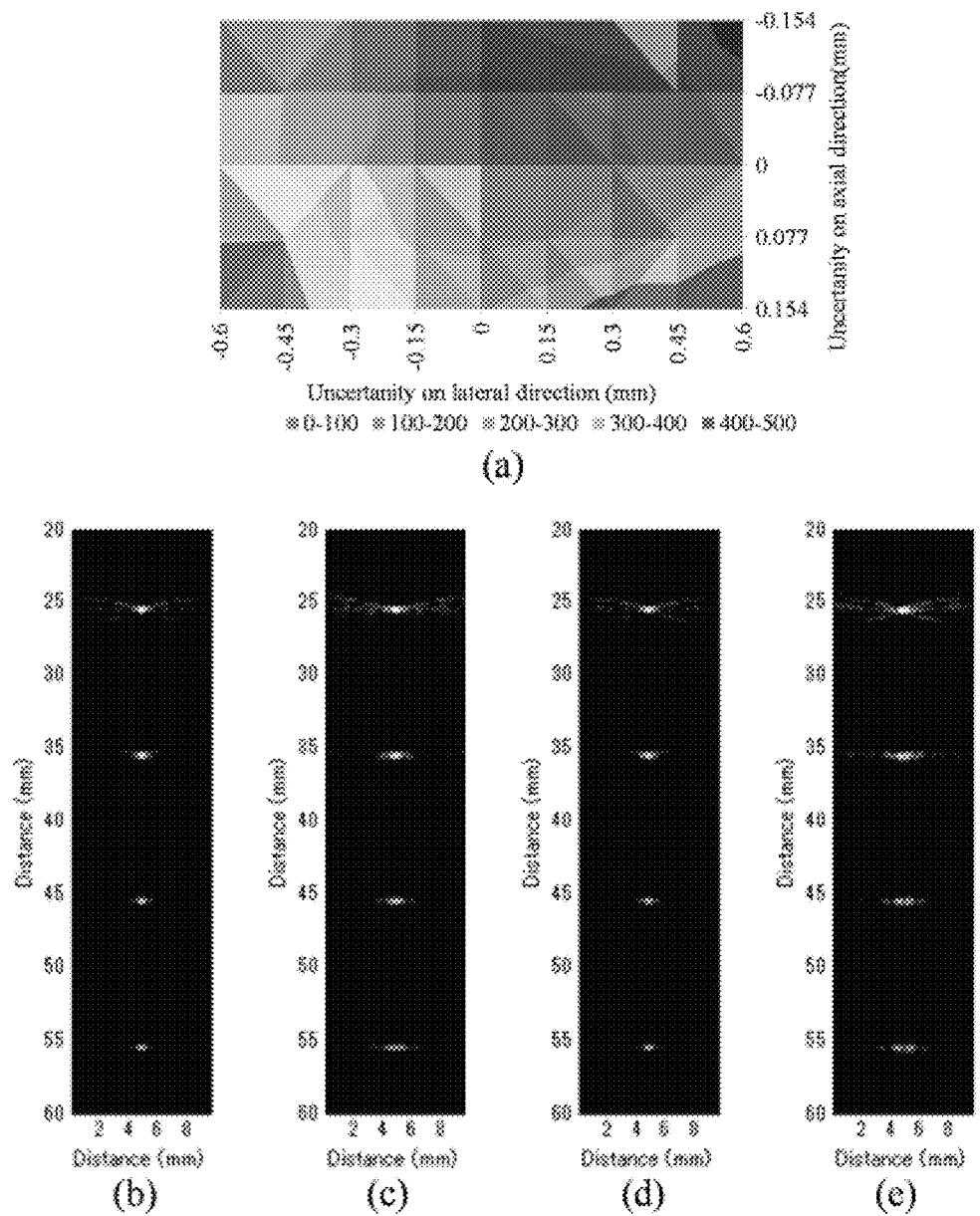
FIG. 5A shows the effect of uncertainty on the size of the reconstructed target.
FIG. 5B shows simulation results for robotic synthetic aperture focusing (R-SAF) with no uncertainty.
FIG. 5C shows simulation results for synthetic aperture focusing (SAF) with no uncertainty.
FIG. 5D shows simulation results for R-SAF with a 0.15 mm displacement in the lateral direction.
FIG. 5E shows simulation results for R-SAF with a 0.15 mm displacement in the axial direction.
Figures 6A, 6B, 6C, 6D, 6E, 6F, 6G:
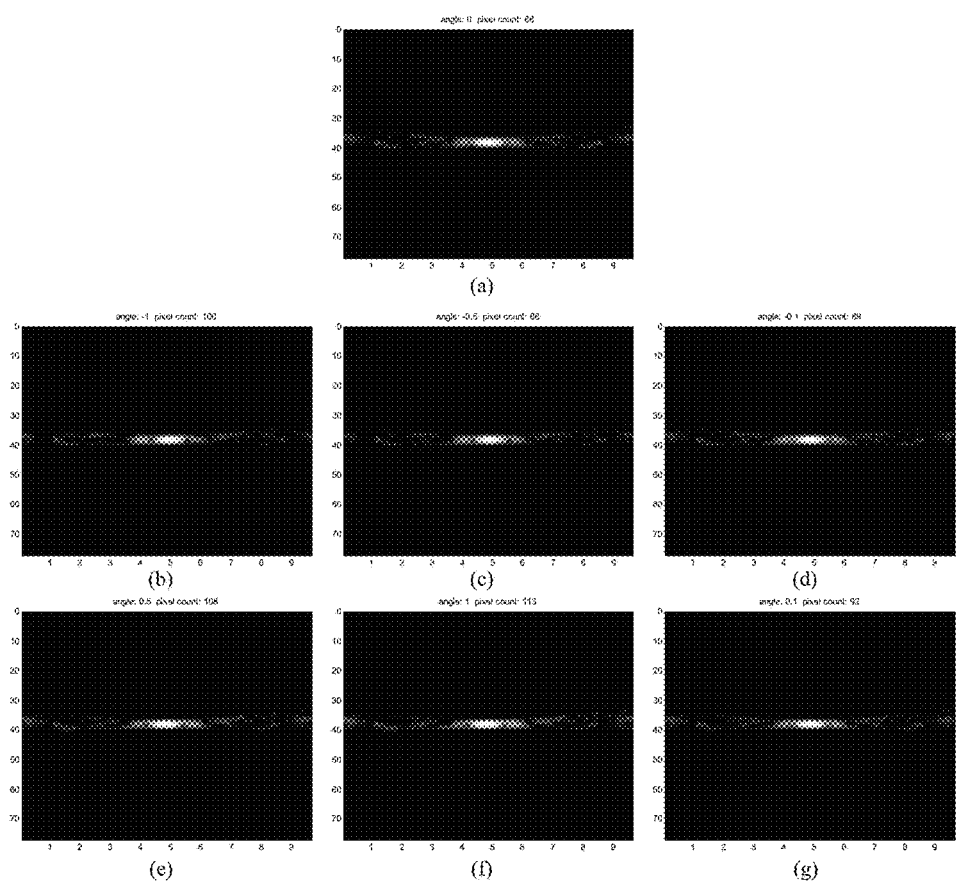
FIG. 6A shows the target with no uncertainty (ground truth)
FIG. 6B shows the effect of in line rotation uncertainty on the size of reconstructed target for a −1° rotation of P2.
FIG. 6C shows the effect of in line rotation uncertainty on the size of reconstructed target for a −0.5° rotation of P2.
FIG. 6D shows the effect of in line rotation uncertainty on the size of reconstructed target for a −0.1° rotation of P2.
FIG. 6E shows the effect of in line rotation uncertainty on the size of reconstructed target for a 1° rotation of P2.
FIG. 6F shows the effect of in line rotation uncertainty on the size of reconstructed target for a 0.5° rotation of P2.
FIG. 6G shows the effect of in line rotation uncertainty on the size of reconstructed target for a 0.1° rotation of P2.

The imaging quality of the point phantoms improved distinguishably in the case of the two-pose reconstruction without any uncertainty for all imaging depths, as shown in FIGS. 5B and 5C. FIG. 5B shows simulation results for robotic synthetic aperture focusing (R-SAF) with no uncertainty, and FIG. 5C shows simulation results for synthetic aperture focusing (SAF) with no uncertainty. On the other hand, different amounts of uncertainty were introduced to the reconstruction of the two-pose data, as shown in FIGS. 5D, 5E, and 6B-6G. FIG. 5D shows simulation results for R-SAF with a 0.15 mm displacement in the lateral direction, and FIG. 5E shows simulation results for R-SAF with a 0.15 mm displacement in the axial direction. In FIGS. 5D and 5E, even though the same amount of displacement (0.15 mm) was applied in both the lateral and axial directions, the displacement in the lateral direction did not have much of an effect on the resolution degradation, while the displacement in the axial direction degraded the lateral resolution more noticeably. The effect of uncertainty (in the axial and lateral directions) is summarized in FIG. 5A. In contrast to the uncertainty in the axial and lateral directions, uncertainty in the direction of the in-plane rotation did not have a significant effect at all for magnitudes less than or equal to 1 degree. FIG. 6A shows the target with no uncertainty (ground truth). FIGS. 6B-6G show the effect of in line rotation uncertainty on the size of reconstructed target for −1°, −0.5°, −0.1°, 1°, 0.5°, and 0.1° rotations, respectively, of P2.

The extent of blurring of the target is expressed as the number of pixels counted over −16 decibel, which is based on the assumption that the more the target is blurred, the more pixels show up on the image at a certain threshold. The condition without any uncertainty is set as the ground truth to express the size under different uncertainty in percentile compared to the ground truth (FIG. 5A). The effect of blurring simulated by introducing uncertainly into in-plain rotation is summarized in Table 4. The results indicate that the uncertainly can be accepted to some extent, and it can be seen that the proposed method is more resilient to the uncertainty in the lateral direction and in the direction of in-plane rotation than the axial direction.

TABLE 4

The effect of blurring simulated by introducing
uncertainly into in-plain rotation

| Angle (°) | % Blurring |
|---|---|
| −1 | 0.14 |
| −0.5 | 0.00 |
| −0.1 | 0.01 |
| 1 | 0.28 |
| 0.5 | 0.23 |
| 0.1 | 0.05 |

An experiment was conducted to confirm the feasibility of the current examples. A universal robot (UR5, Universal Robot) was used to move the transducer, and pre-beamformed RF signals were collected from a clinical ultrasound machine (Sonix Touch, Ultrasonix Inc.) using a data acquisition device. A point target was placed in a water tank at a 3.5 mm depth. A 38.4 mm L14-5W transducer with 128 elements was prepared and the center 32 elements (9.6 mm) were used for easier comparison with the method. This kept the F number high, and the imaging depth was extended. In the single pose case, the target was located at the center with respect to the transducer. A 19.2 mm aperture was generated by sweeping the probe 4.8 mm to the left and 4.8 mm to the right relative to the center position of the single pose. This condition is expressed as two positions because it is equivalent to two 9.6 mm probes that do not overlap. A 5 MHz center frequency was transmitted with a 40 MHz sampling frequency. The dynamic range of −20 dB was set for the display.

For the ultrasound calibration, one directional lateral translation was applied, so two rotations were aligned using an active-echo element [2]. The active-echo element reports the mid-plain of the ultrasound transducer as well as the depth of the element. After that, two relative rotations of the probe to the robot end effector were manually aligned to fit to the robot-based coordinate, which enabled sweeping of the transducer in a pure translation corresponding to the robot.

Figure 7A:
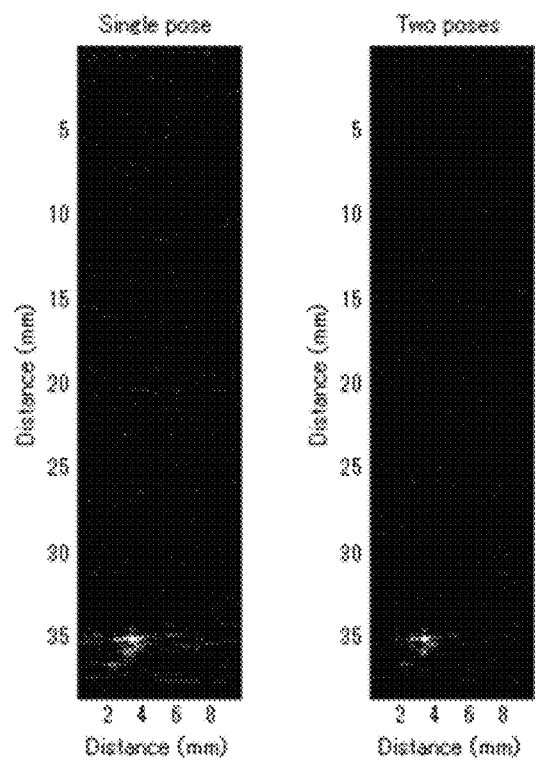
FIG. 7A shows experimental reconstructed images of SAF (left) and R-SAF (right)
Figure 7B:
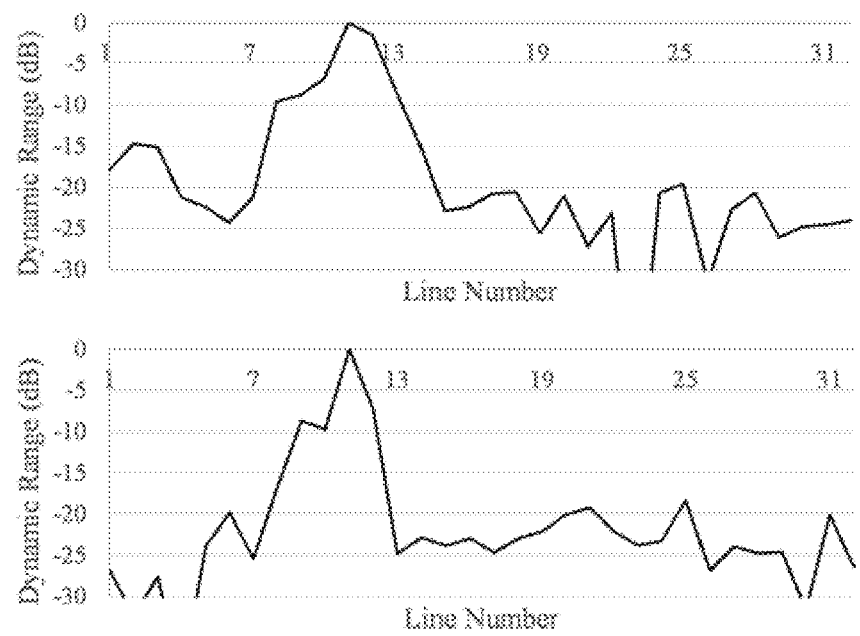
FIG. 7B shows experimental beam profiles of 3.5 mm depth of SAF (upper) and R-SAF (lower)

FIG. 7 depicts the experimental result of the robotic synthetic aperture focusing. Reconstructed images of conventional SAF and R-SAF are compared. During the reconstruction, the existence of uncertainly caused by limited calibration and control accuracy was confirmed in pre-beamformed signals, and the axial direction correction was done to mitigate the artifact from misalignment. The lateral resolution of R-SAF was better than SAF as seen by comparing the width of the target at 3.5 mm depth.

The final process was to combine the ultrasound calibration and the synthetic aperture reconstruction. An ultrasound transducer calibrated through an AE calibration method was used. This ultrasound transducer was mechanically tracked using a robot arm, and ultrasound data was collected while the robot arm was moved to multiple positions. The relationship between the data was determined using tracked information, and a synthetic aperture algorithm was used for reconstruction. A multipurpose ultrasound phantom (Nuclear Associates 84-317) was used. Since the accuracy of the tracking has limitations, image shift compensation was necessary.

Figure 8:
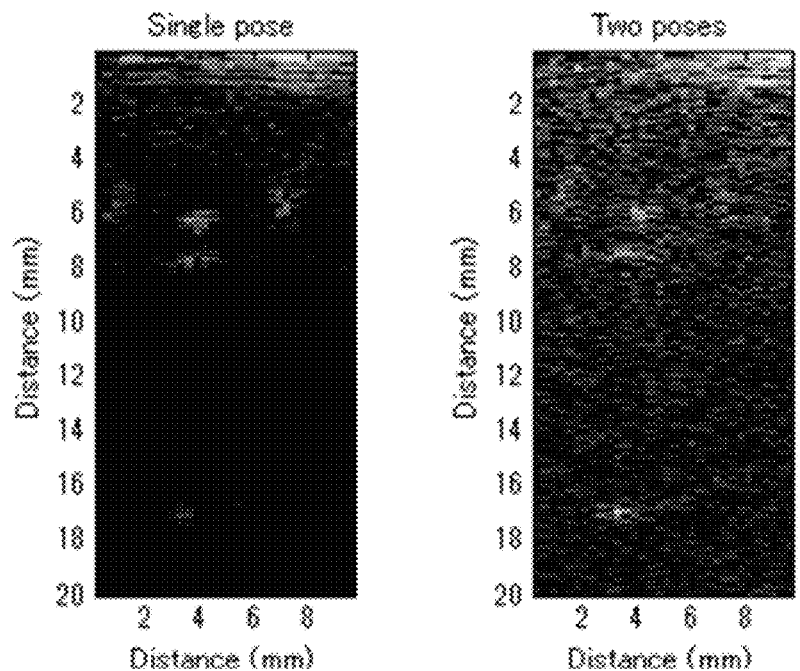
FIG. 8 shows the experimental result of the ultrasound phantom using the tracked transducer.

The experimental result is shown in FIG. 8. There should be two line inclusions at 6 mm and 18 mm, but only the two poses condition could clearly see the line phantoms. The contrast of the two poses was worse than the single pose because the received ultrasound signal was not stable.

From the result of the simulation, we can see that uncertainty of the lateral resolution is not really problematic compared to the axial resolution because the axial resolution is sensitive to the center frequency of transmission. A probe with a center frequency of 5 MHz was used in the simulation to correspond to the center frequency used in the experiment, and decreasing the center frequency canceled the effect of the axial resolution degradation. In reality, a low frequency probe was used to visualize the deep sight because it is hard to receive signals using high frequency due to attenuation. Since the intrinsic resolution of the low frequency probe is bad, expansion of the aperture size is necessary. In other words there is a strong demand to apply the method described herein.

To overcome the uncertainty, image based correction is possible. The continuity of pre-beamformed signals can be an indicator. Also, if there is an overlap between displaced position data, the overlapping area should contain identical signals. Therefore, finding the maximum cross correlation, or using similar methods to find the time lag at which the maximum similarity between echo signals from different poses and/or from different receive elements is realized, can be used to correct for tissue motion or probe position uncertainty. If the uncertainty is predictable, it is possible to compensate for the displacement during the reconstruction process.

For reconstruction, SAF with a single active element for transmission and reception was considered. This was an effective way to evaluate R-SAF because this was the simplest condition, and the received aperture had no overlap. Multi-element reception or transmission can also be considered. An advantage of R-SAF is that assuming a single element transmits a signal, it is possible to receive signals from a wider field by synthetizing the received signals.

Moreover, the advantage of a robotically tracked transducer is that it not only can expand the aperture size in a specific direction as the linear probe, but it also has huge flexibility to acquire signals. For example, curvilinear or arc shape acquisitions are possible. This flexibility can be applied based on demand.

Example 2—Implementation of Swept Synthetic Aperture Imaging

Despite advancements in array construction, beamforming algorithms, and image post-processing, deep imaging targets still pose a challenge for modern ultrasound imaging. The resolution of an ultrasound image is limited by diffraction effects and largely dependent on three factors—transmit wavelength, imaging depth, and aperture extent. For a given target, imaging depth is fixed. The transmit wavelength is variable, but attenuation of the transmitted pulse through tissue increases with frequency, limiting the gains in resolution that can be made in practice. The aperture extent depends on the transducer used and is conventionally limited by the footprint of the array. We describe a system that extends the effective aperture and increases the imaging resolution using precisely tracked transducer motion.

Transducer motion has historically been used to extend the field of view (FOV) of an ultrasound image without altering the resolution or image quality to reduce speckle noise by summing envelope-detected echo signals. Original ultrasound images were formed using a single focused element in conjunction with a moving stage to sweep over the area of interest, forming a C-scan in the focal plane or a B-mode in the sweep plane [1]. Using arrays to acquire a wider field of view from a single physical aperture position, it was demonstrated that multiple FOVs could be stitched together into a panorama without the use of position tracking [2]. Motion can also extend the image into the elevation dimension, using a rocking probe to stitch together multiple axial-lateral planes into a volume. Using images acquired from different locations, it is also possible to perform spatial compounding, incoherently combining images to reduce their speckle texture [3].

In contrast to these image post-processing techniques, it is also possible to coherently combine information from multiple transmit events across an array or steered in different directions into a single RF data set. These "synthetic aperture" methods focus data from each transmit event, accounting for the full transmit and receive path length of the wave, and sum the results to create an effective aperture equivalent to the combination of the subapertures4. Performing single-element transmit events across the array and recording all receive channel data, for example, is enough to reconstruct an image that behaves as if the entire array was used to sample each point in the field with focused transmit events. "K-space" theory can be used to analyze the spatial frequencies sampled by a given acquisition and, by the Fourier transform relationship, predict the resulting point spread function [5]. If each transmit event contributes to a unique region of K-space, the synthetic aperture image will have an extended region of support and therefore produce a higher-resolution point spread function.

We describe herein a system that exploits motion to sample regions of K-space that are not accessible from a single aperture position and uses synthetic aperture techniques to coherently combine the recorded data into a high-resolution image with an effective transducer size beyond the physical transducer footprint. This technique is similar to methods used in radar/sonar for creating a high-resolution image from a moving source/receiver attached to a ship or plane, for example [6].

Figure 9:
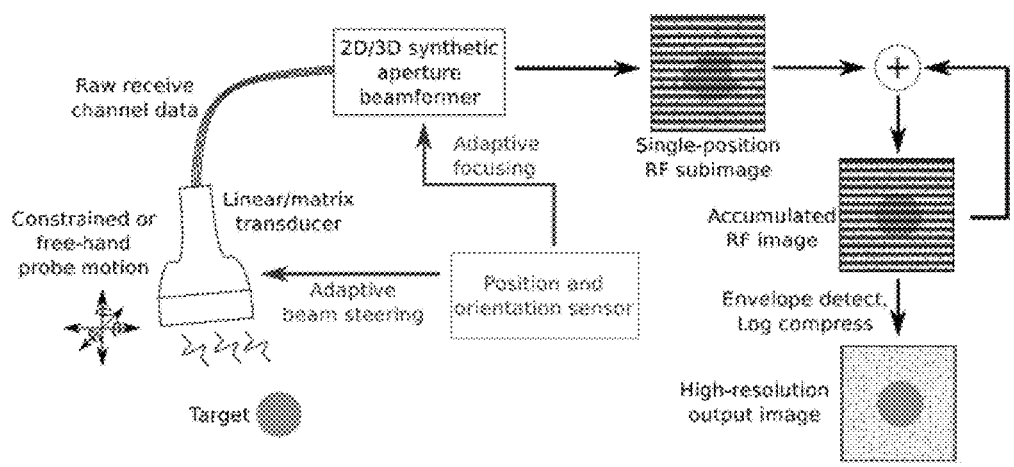
FIG. 9 shows the swept synthetic aperture imaging system according to some embodiments of the invention.

The system described herein extends the effective transmit and receive apertures beyond the physical constraints of the array using "swept synthetic aperture" imaging, as shown in FIG. 9. The transducer can be a conventional clinical linear or matrix array, capable of individually apodizing and focusing each element on transmit. The complexity of the system can vary, and can use a linear array with constrained motion or a matrix array with free-hand motion to collect data. During the acquisition, the probe is swept over the region of interest, keeping the imaging target in the FOV using mechanical rotation/translation and beam steering. The unfocused receive channel data from each transmit event is recorded along with the precise relative position and orientation of the transducer. Position tracking informs both the transmit sequence (if steering is used) and the beamforming to accumulate low-resolution RF images coherently and form a high-resolution output image.

Figures 10A, 10B:
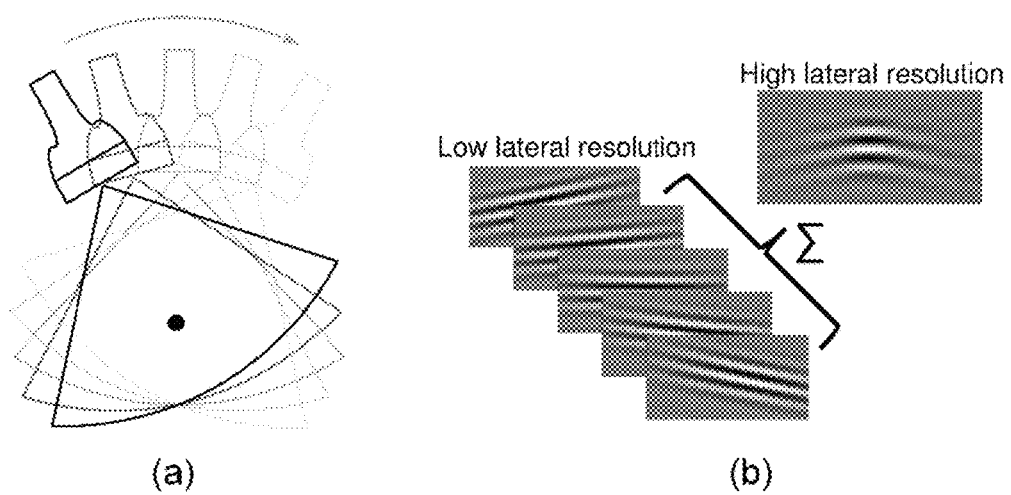
FIG. 10A illustrates the acquisition procedure, in which overlapping FOVs are acquired from each transducer position using rotation of the transducer about the focal point.
FIG. 10B illustrates the reconstruction procedure, wherein a low-resolution image is beamformed for each transducer position using knowledge of the transducer position and orientation and coherently summed to form a high-resolution synthetic aperture image.

Conventionally, a FOV relative to the transducer is beamformed using knowledge of the geometry of the array. For a swept transducer, this procedure is modified to maintain a constant frame of reference in order to coherently align the focused RF data from each transmit event. A fixed grid of points is beamformed across all transmit events, adjusting the transmit and receive path lengths to account for the position and orientation of the transducer. Each individual image formed this way is a low-resolution image, restricted by the physical transmit and receive aperture sizes. The coherent sum of these subimages creates a synthetic aperture over the full extent of the swept probe, resulting in a high-resolution image. This process is illustrated in FIGS. 10A and 10B. FIG. 10A illustrates the acquisition procedure, in which overlapping FOVs are acquired from each transducer position using rotation of the transducer about the focal point. FIG. 10B illustrates the reconstruction procedure, wherein a low-resolution image is beamformed for each transducer position using knowledge of the transducer position and orientation and coherently summed to form a high-resolution synthetic aperture image.

Several types of imaging sequences should be considered for use with the swept aperture system. First, the choice of transmit focus will impact overall image quality and FOV. The method illustrated in FIG. 10A shows a diverging wave transmit, using a single element in transmit as a point source. The wave produced spherically diverges from the face of the transducer, sending energy over an area that expands beyond the physical aperture extent according to the acceptance angle of the element. While this method produces a broad FOV and is technically simple, the energy transmitted by a single transducer element is limited and impacts the signal-to-noise ratio of the recorded signal. It is possible to simulate a diverging wave using a "virtual source" behind the array and several transducer elements, providing a similar broad FOV with improved signal amplitude[7].

An alternative to a diverging source is a plane wave, transmitting a signal from all array elements with no focal delays. The wave produced shows little geometric spreading, restricting the useful FOV to directly in front of the aperture. Depending on the motion of the transducer chosen, the overlap between subimages created using this method may not be sufficient to image the target structure. However, the use of all available array elements greatly improves the signal-to-noise ratio of the recorded signal.

A compromise between the two techniques is to place the virtual source point in front of the array, using a conventional focused transmit[8]. All elements can be used in transmit to increase signal amplitude, but the region beyond the focal point extends beyond the lateral footprint of the aperture. The FOV is limited to an hourglass-shaped region determined by the effective opening angle from the virtual source. This technique requires more post-processing to properly combine the partially-overlapping FOVs.

It is also necessary to consider the combination of electronic and mechanical steering of the transmitted pulse. In a continuous sweep of the transducer, it is possible to use identical transmit events and fully sample frequency space to build up a high-resolution image. However, if the acquisition rate is significantly higher than the sweep rate, redundant information will be captured with this method. Instead, it is possible to steer the transmit beam in the plane wave or focused transmit case or electronically translate the diverging source to sample additional frequency space from the same physical array location. While this may provide redundant information once the array is swept, the same frequency space can then be sampled in different aberration and clutter conditions in vivo in order to potentially average out or to measure and compensate for their effects.

Figures 11A, 11B, 11C:
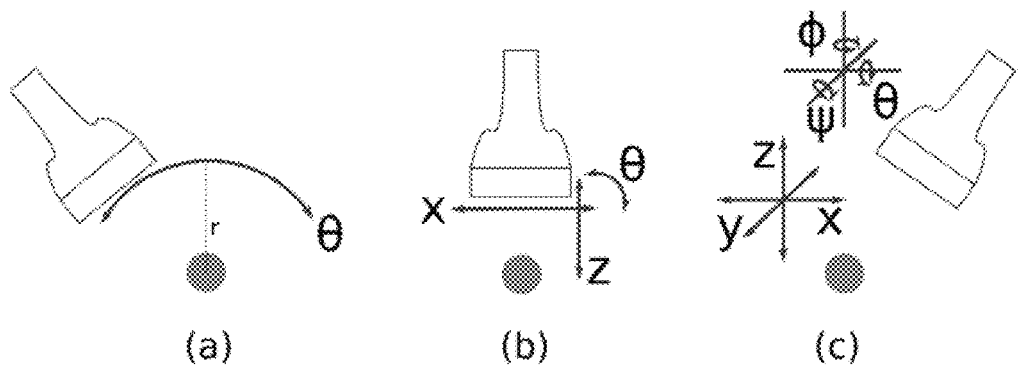
FIG. 11A shows a scanning geometry based on one degree of freedom—a polar scan at a fixed radius.
FIG. 11B shows a scanning geometry based on three degrees of freedom—full motion in the imaging plane.
FIG. 11C shows a scanning geometry based on six degrees of freedom—free motion in space.

The technical complexity of the system is directly tied to the capability of the transducer tracking system. FIGS. 11A-11C illustrate three possible scan geometries. The simplest possibility, shown in FIG. 11A, is a one degree of freedom system that allows an angular sweep at a fixed radius. This could be implemented using a fixed rotational arm or an arc-shaped track around the target. In this setup, in contrast to a single-dimension sweep in the lateral dimension, the transducer is always mechanically rotated to face the imaging target and no beam steering is necessary. The effective aperture is only extended in the plane of the sweep, although a matrix transducer could still be used to provide a volumetric image.

A one degree of freedom system may limit the geometries of targets that can be scanned to cylindrical surfaces or objects in a water tank. A more clinically-useful system would include three degrees of freedom, allowing the same extension of the effective transducer size but free motion in the sweep plane. This motion, illustrated in FIG. 11B, can be achieved using a translation and rotation stage setup. Because it is possible to mechanically direct the transmit beam away from the target in this case, adaptive beam steering or a wide FOV may be necessary.

The least restrictive system would include six degrees of freedom, allowing free-hand motion of the transducer through space. This geometry is illustrated in FIG. 11C. As in the three degree of freedom system, beam steering or a wide FOV may be necessary to maintain overlap between the reconstructed images. The extra degrees of freedom allow for extension of the effective aperture in both the lateral and elevation dimensions based on the sweep path. This method can be achieved using a jointed mechanical arm, an electromagnetic tracker, or an optical positioning system. In all cases, the accuracy required in the axial beam direction is a small fraction of a wavelength, while the orthogonal dimensions have a larger tolerance based on the point spread function.

The Siemens ACUSON SC2000 ultrasound system (Siemens Medical Solutions USA, Inc., Mountain View, Calif.) and 4Z1c volumetric transducer were used with a custom imaging sequence to collect individual receive channel I/Q data for each transmit event. At each aperture position, a 3×3 subelement centered laterally on the array was used to transmit a plane wave (treated as a diverging wave due to the small element pitch). This was repeated for each group of 3 elements in the elevation dimension, covering the full elevation extent of the array at a single transducer position.

The transducer was mounted to a rotation stage coupled with a three-axis translation stage and controlled by a Newport MM3000 motor controller (Newport Corporation, Irvine, Calif.). Although the stage provides axial, lateral, elevation and axial-lateral rotation capabilities, the controls were used to mimic a one degree of freedom system. After each acquisition, the transducer was rotated about the geometric center at 7.1 centimeters by 0.305 degrees. This motion was accomplished using an axial and lateral translation of the array in addition to a rotation. 101 acquisitions were made over a total sweep extent of 30.8 degrees. This is an approximation to the continuous transducer motion required for an in vivo scan, assuming that the acquisition rate is significantly faster than the mechanical sweep rate. The stage position was stored for every transmit event for use in beamforming.

Figure 12:
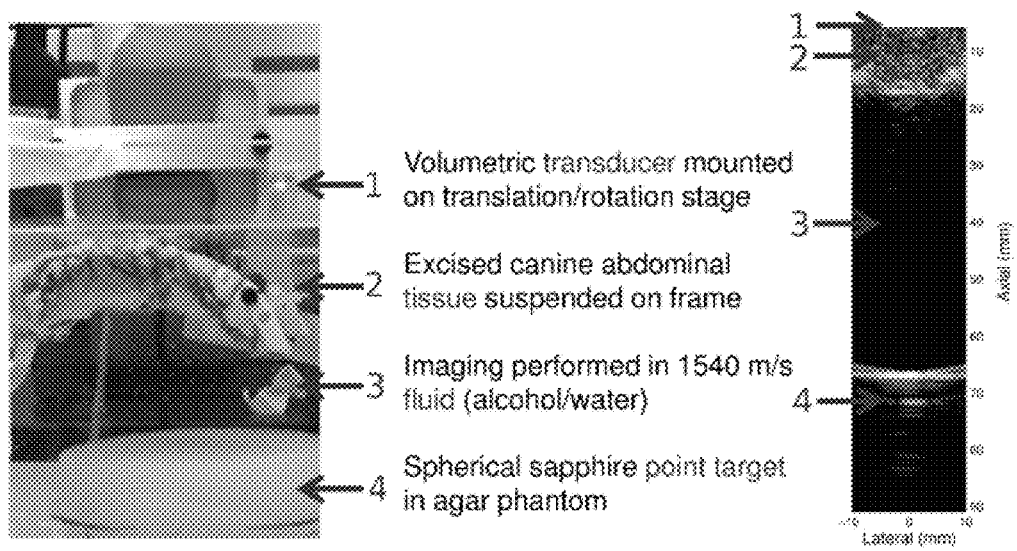
FIG. 12 shows a photo of the translation stage system with labeled components (left) and a single-position B-mode image with labeled components, with 50 dB of dynamic range displayed (right)

The experimental target setup is shown in FIG. 12, which includes a photo of the translation stage system with labeled components (left) and a single-position B-mode image with labeled components, with 50 dB of dynamic range displayed (right). Imaging was performed in a tank filled with a solution of 1-propanol and water to produce a fluid with a sound speed of approximately 1540 m/s at room temperature (approximately 23 C)[9]. A custom agar phantom with a 0.25 mm-diameter sapphire target was placed at the bottom of the tank, with the sapphire located approximately 7.1 cm from the face of the transducer. The distance from the rotation point on the translation stage to the face of the array was measured to be 42.7 mm, allowing for conversion from the recorded coordinate system to the imaging coordinate system.

The imaging sequence was also performed after the addition of ex vivo tissue directly in front of the transducer, between the array and the target. Approximately 10 cm×20 cm of canine anterior abdominal wall was harvested, consisting of skin (hair removed), subcutaneous fat, fascia, abdominal muscle (including rectus abdominus and transverse abdominus) and peritoneum. Adipose tissue underlying the peritoneum was removed. The overall thickness, approximately 2 cm, and elasticity were conserved by mounting the tissue immediately following excision onto a plastic frame and submerging the structure in the tank. The target and relative location of the target to the translation stage was unchanged. Due to technical malfunction, transmit events 31-38 (out of 101) are missing from the data set.

FIG. 12 also shows a 2D B-mode ultrasound image, with features matched between it and the setup photograph. The transducer is located at an axial depth of 0 mm. The abdominal tissue creates a speckle region and produces clutter that decreases in amplitude with depth. There is a large region of fluid between the tissue and the phantom, reducing the impact of clutter and leaving only aberration effects. The top interface of the phantom is bright and creates clutter common to both the control and experimental trials. The point target appears several millimeters below the interface of the phantom.

A Field II simulation[10,11] was constructed to match the experimental protocol described above. The transducer simulated had a center frequency of 2.5 MHz with a fractional bandwidth of 0.6. Three lateral rows of the array were used, exciting all elevation elements in a single transmit event. In lieu of full synthetic aperture focusing, fixed transmit and receive focusing were used at the point target location.

The focused RF data were used to simulate a mechanical sweep by rotating the output about the focal point, equivalent to rotating the transducer. The resulting subimages were summed to create a high-resolution image representing the full 30.8 degree aperture.

The two-dimensional point spread function for each experiment was analyzed by extracting the axial-lateral plane of the reconstructed volume. B-mode images of the point target were made by envelope-detecting the summed RF data and log compressing the result for display over a 50 dB dynamic range. Lateral profiles were extracted from this image using a single axial depth through the peak of the point target. The resolution was measured from these lateral profiles using the full width at half maximum (FWHM), the lateral distance between the −6 dB points on the curve. This resolution was measured as a function of transmit F-number, axial depth divided by lateral aperture width, requiring summed images from varying subsets of the physically rotated images. K-space plots were constructed by taking the two-dimensional Fourier transform of the axial-lateral image to produce a plot of axial and lateral frequency. The plots are rotationally symmetric, so only the positive axial half-plane is shown.

Aberration was estimated for each transducer position by measuring the difference in wave arrival time across the array from the point target and attributing the delays to a thin phase screen model[12,13]. A noise-robust least squares estimation was used to identify the arrival time due to the low signal-to-noise ratio and strong clutter present in some locations.

In the control case, an absolute arrival time for each element was estimated using the peak of the signal and any delay was attributed to the average of all elements on transmit and the selected element on receive. All permutations of cross-correlation between channels were used as additional estimates of the difference in delay between those channels. These estimates were associated with their normalized cross-correlation values to emphasize better-quality estimates.

In the tissue case, an absolute arrival time for each element was estimated using cross-correlation with a reference waveform, the averaged waveform from the control case. All permutations of cross-correlation between channels were computed as in the control case.

The weighted, regularized linear least squares solution for each case was set up as a concatenation of the above estimates into the observation vector Y and the description of each estimate as a linear sum of individual element delays X given by H and weighted by W. A two-dimensional regularization term $\Gamma$ is included to enforce spatial smoothness of estimates across the aperture using a second-order central finite difference. The estimates $\hat{X}$ are given by $$\hat{X} = (H'WH + \Gamma'\Gamma)^{-1} H'WY. \quad (2.1)$$

The results for the control case were subtracted from the experimental results to control for variations in the construction of the array that appear as delays across the aperture. The median delay from each aperture position was removed to control for variations in absolute estimates of arrival time between positions.

The synthetic aperture data set allows for a parametric study of image quality as a function of aperture size and configuration. Aperture size can be studied by summing varying subsets of the full data set since each transmit event (sweep location) is separately beamformed14. The aperture was grown symmetrically outward from the center of the array in 0.305 degree increments to either side (0.61 degrees per step). For each configuration, the envelope of the image was formed from the summed RF data and the FWHM was plotted against the effective transmit F-number.

The data set was also used to study the sampling of the synthetic array, or the distance between swept transmit events used to form the high-resolution image. The original data were sampled at 3.2 samples per degree. The data set was downsampled by factors of two, producing sampling down to 0.1 samples per degree. In each case, the point spread function was observed from the envelope detected signal and the k-space representation was formed.

It is also possible to apply an apodization to the synthesized transmit aperture by weighting the data from each transmit event before summation. A conventional rectangular array has a lateral frequency spectrum shaped like a triangle, equal to the self-convolution of the rectangular function[5]. In order to reproduce this shape, the swept aperture data was multiplied by triangular weights, emphasizing data from the center position over the extremes of the sweep. Lateral frequency profiles were extracted using the average of several axial frequencies centered on the axial center frequency.

The experimentally measured axial-lateral point spread functions were used to simulate anechoic lesions in speckle in order to characterize degradation of the image due to distortion of the side lobes and clutter. The point spread function was convolved with randomly positioned sub-wavelength scatterers of normally distributed scattering amplitudes, with a 5 mm-diameter anechoic region at the center of the FOV. For 1000 speckle realizations, contrast and contrast-to-noise ratio (CNR) were measured as $$\text{Contrast} = \frac{\mu_o - \mu_i}{\mu_o} \text{ and} \quad (2.2)$$

$$CNR = \frac{\mu_o - \mu_i}{\sqrt{\sigma_o^2 + \sigma_i^2}}, \quad (2.3)$$

where $\mu_o$ and $\mu_i$ are the mean values and $\sigma_o^2$ and $\sigma_i^2$ are the standard deviations inside and outside the region of interest. A 5 mm-diameter region at the same depth laterally displaced from the lesion was used as the background comparison for the measurements.

Figures 13A, 13B, 13C, 13D:
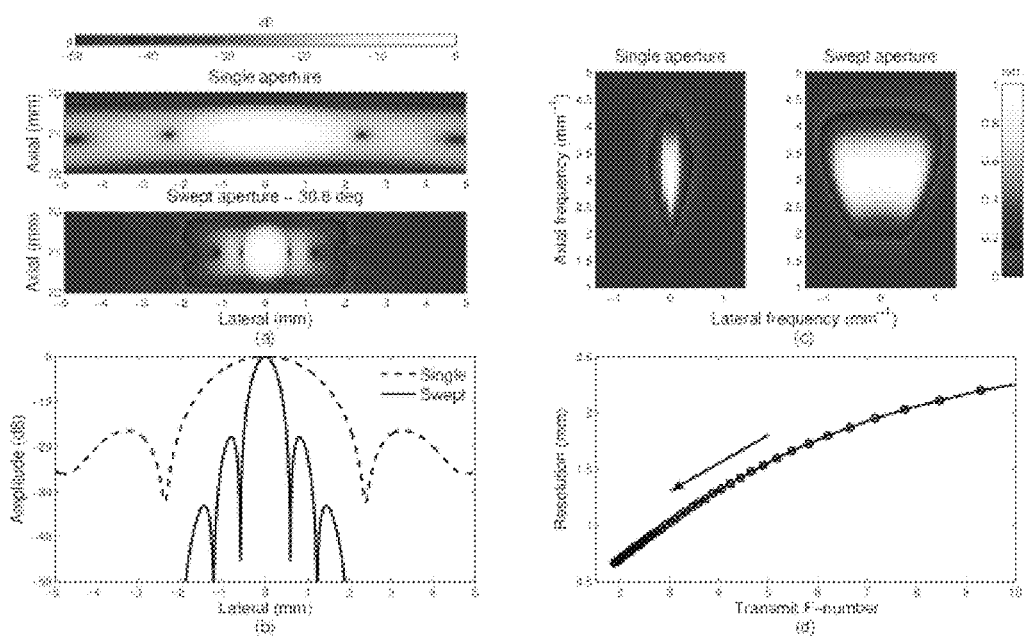
FIG. 13A shows the point spread functions for a single aperture position and swept aperture over 30.8 degrees.
FIG. 13B shows the lateral point spread function through the center of the point target. Resolution improvement in the full width at half maximum (FWHM) is observed from 2.76 mm to 0.66 mm.
FIG. 13C shows the K-space (spatial frequency spectrum) found by Fourier transform showing wider lateral coverage by the swept aperture.
FIG. 13D shows resolution plotted against effective transmit F-number based on the lateral aperture length.

The results of the Field II simulation are shown in FIGS. 13A-13D. FIG. 13A shows the point spread functions for a single aperture position and swept aperture over 30.8 degrees. FIG. 13B shows the lateral point spread function through the center of the point target. Resolution improvement in the full width at half maximum (FWHM) is observed from 2.76 mm to 0.66 mm. FIG. 13C shows the K-space (spatial frequency spectrum) found by Fourier transform showing wider lateral coverage by the swept aperture. FIG. 13D shows resolution plotted against effective transmit F-number based on the lateral aperture length. The arrow indicates the direction of increasing aperture size. The point target reconstructed from a single transmit position has poor lateral resolution with a FWHM of 2.76 mm. The first side lobes can be seen in the lateral profile, with subsequent side lobes expected to be present at decreasing amplitudes. The width of this point spread function is dominated by the extent of the receive aperture, covering the physical array, rather than the narrow transmit aperture. The K-space plot for this target shows the conventional "teardrop"' shape with a narrow lateral extent, corresponding to low spatial frequencies.

The results for the swept aperture show a narrowed point spread function, corresponding to a FWHM of 0.66 mm. The main lobe and side lobes of the point spread function are visible in the lateral profile, showing significantly reduced lateral extent. As the aperture is enlarged, the transmit F-number is reduced and the resolution improves. This function is only asymptotically linear with F-number due to the differently sized transmit and receive apertures. The k-space plot shows the presence of higher lateral spatial frequencies and the same axial spatial frequencies. When the transducer is rotated about the target, the frequency space sampled is also rotated according to the rotation property of the Fourier transform. The k-space plot for this target is effectively the k-space plot for the single aperture swept out over the 30.8 degree sweep and summed together.

Figures 14A, 14B, 14C:
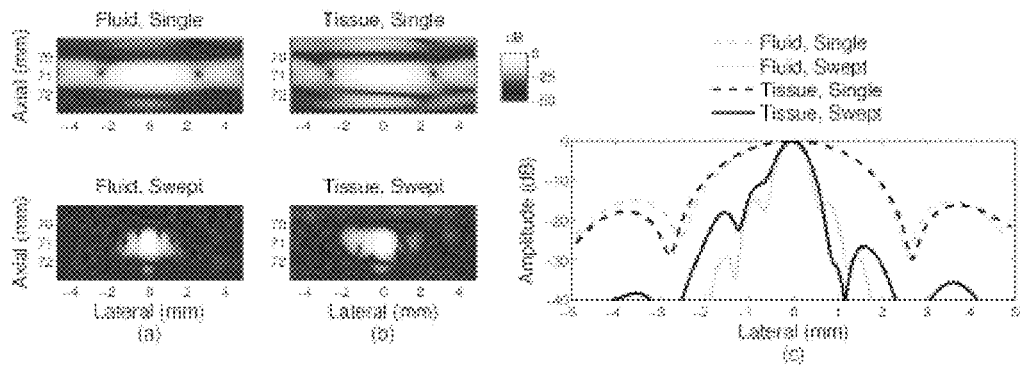
FIG. 14A shows the experimentally measured point spread function for a 30.8 degree sweep without the abdominal tissue layer present.
FIG. 14B shows the experimentally measured point spread function for a 30.8 degree sweep with the abdominal tissue layer present.
FIG. 14C shows the experimentally measured lateral point spread function for a 30.8 degree sweep.

Experimentally measured point spread functions for a 30.8 degree sweep are shown in FIGS. 14A-14C. Resolution gains are observed both without (14A) and with (14B) the abdominal tissue layer present. In the fluid path case, FWHM improves from 3.01 mm to 0.71 mm. In the tissue case, the FWHM improves from 3.15 mm to 0.85 mm. Distorted side lobes are observed due to aberration and the missing transmit events. In the control case, without the tissue layer present, the single aperture position creates a point spread function comparable to the one observed in simulation. Clutter is present in the background of the image due to the acoustically mismatched top interface of the agar phantom, but the point target is clearly visible. The side lobes present have similar extent and amplitude compared to the simulation and a FWHM of 3.01 mm is observed. The swept aperture greatly increases the resolution, reducing the FWHM to 0.71 mm with the 30.8 degree sweep. Clutter in the background is noticeably reduced and the side lobes present match well with simulation.

In the presence of the tissue layer, the observed single position image shows increased clutter but is very similar to the control case. The main lobe and side lobe widths and amplitudes are similar, with a FWHM of 3.15 mm. The effects of aberration are apparent in the swept case, producing distortions and increased clutter despite the increase in resolution. The FWHM improves to 0.85 mm, but the side lobes seen in the lateral profile plot are asymmetrical and have raised amplitudes. Some asymmetry is due to the missing transmit events, but this alone does not account for the magnitude of the distortions present. Despite the artifacts present, the overall resolution improvement is comparable to the control case and suggests that realistic levels of aberration do not impair the swept aperture technique.

Figure 15:
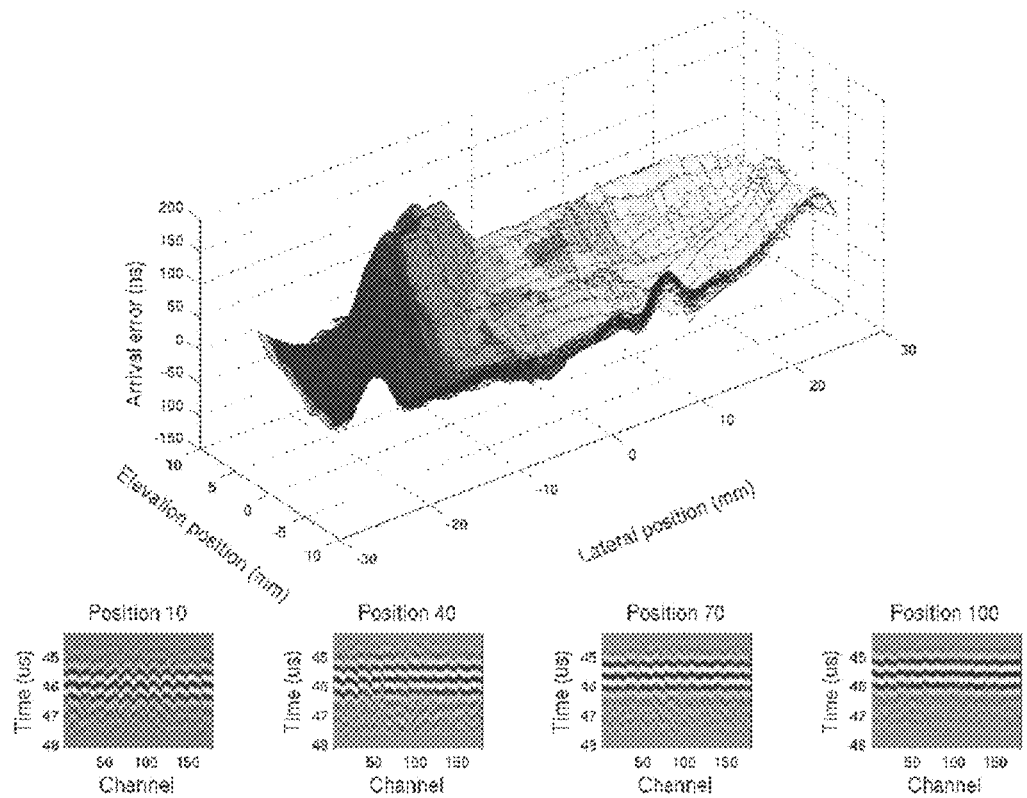
FIG. 15 illustrates the combination of aberration profile estimates from each transmit position in the sweep.

The combination of aberration profile estimates from each transmit position in the sweep are shown in FIG. 15. The upper plot shows estimated aberration profiles from each transmit event, wherein the color scale indicates the aperture position throughout sweep. There is strong agreement between adjacent estimates, showing distinct features in the abdominal tissue layer that corrupt the phase of the arriving wave. The lower plots show sample channel data profiles across the extent of the sweep. Discontinuities appear in these images due to the unwrapping of the 2D aperture onto a single channel dimension.

The color map of the plots in FIG. 15 indicates transmit position, with all estimates overlaid without averaging. Any discontinuities in color indicate disagreement in the estimates, but there is overall excellent agreement across the synthesized aperture. The left side shows a sharp ridge on the order of 100 ns distortion, explaining the asymmetry seen in the point target of FIGS. 14B and 14C. Signals passing through this region experience a different effective acoustic path length from the rest of the array in both transmit and receive. Smaller variations exist across the rest of the aperture, showing distinct ridges and bumps that likely correspond to physical features in the tissue layer. Acoustic effects such as refraction are not accounted for by this model and would cause a gross misregistration if present from a particular imaging location.

With this knowledge, it would be possible to realign the channel data from each transmit event to restore coherence across the synthesized aperture. The correction would be made using the thin phase screen model, varying both the transmit and receive path lengths used in beamforming. The result would look nearly identical to the control case, with the exception of clutter in the background. This result is not presented here as it does not provide any insight in the absence of extended imaging targets. This correction is more difficult in vivo because there is no point target to use to estimate arrival time. Other metrics such as speckle brightness can be used to estimate aberration[15], but these algorithms are computationally intensive. Even without correction, these results suggest that resolution improvements can be made in the presence of aberration.

Figures 16A, 16B, 16C:
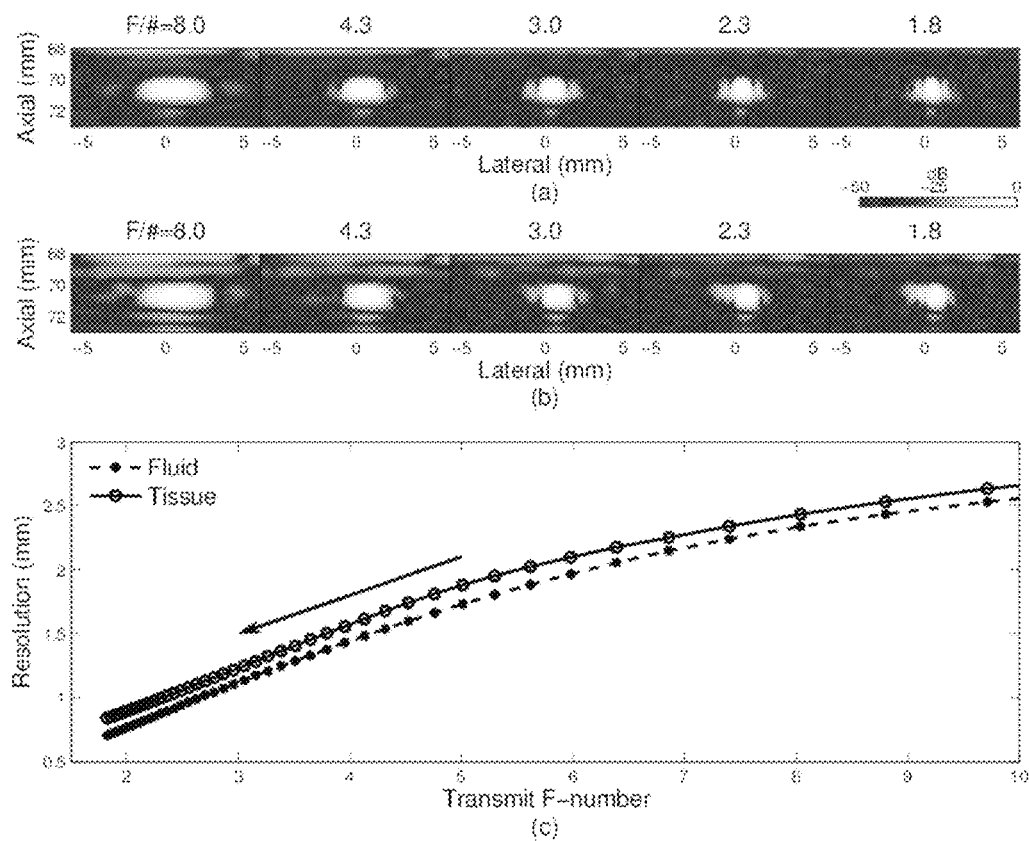
FIG. 16A shows fluid path point target images over a range of F-numbers from 8.0 to 1.8.
FIG. 16B shows point target images with abdominal tissue present over a range of F-numbers from 8.0 to 1.8.
FIG. 16C shows the measured resolution (FWHM) over a range of transmit aperture sizes with and without abdominal tissue present.

The experimental results for the resolution as a function of transmit F-number are shown in FIGS. 16A-16C. FIG. 16A shows fluid path point target images over a range of F-numbers from 8.0 to 1.8. FIG. 16B shows point target images with abdominal tissue present over a range of F-numbers from 8.0 to 1.8. FIG. 16C shows the measured resolution (FWHM) over a range of transmit aperture sizes with and without abdominal tissue present. The arrow indicates the direction of increasing aperture size. Both the control and tissue cases show continued improvement as the aperture expands, with similar results between the two. As in the simulation, the resolution is only asymptotically a function of the transmit f-number, showing reduced improvement in the region where the receive aperture dominates the total effective aperture size. It is important to note that the x-axis varies with the reciprocal of aperture size. Each data marker on the lines represents a fixed difference in aperture size, demonstrating the diminishing returns at large sizes because F-number varies less with each section of aperture added. This may put practical limits on the size of the swept aperture, although resolution should continue to increase.

Figures 17A, 17B, 17C, 17D:
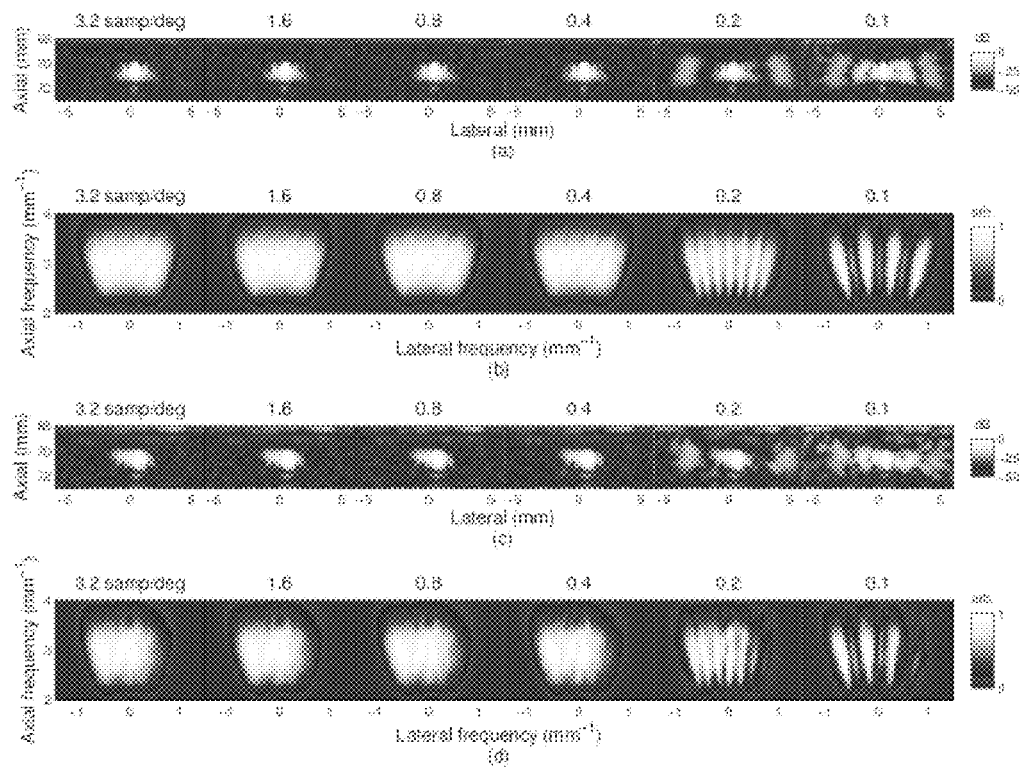
FIG. 17A shows a point target without the abdominal tissue layer using the full swept aperture extent with varying angular sampling.
FIG. 17B shows K-space plots of a point target without the abdominal tissue layer for various amounts of angular sampling.
FIG. 17C shows a point target with the abdominal tissue layer using the full swept aperture extent with varying angular sampling.
FIG. 17D shows K-space plots of a point target with the abdominal tissue layer for various amounts of angular sampling.

Angular sampling of the synthetic aperture space plays an important role in the design of a swept aperture acquisition sequence. FIGS. 17A and 17C show a point target without (17A) and with (17C) the abdominal tissue layer using the full swept aperture extent with varying angular sampling. FIGS. 17B and 17D show K-space plots of point targets showing reduction in angular sampling. The fastest acceptable sweep rate can be determined by dividing the acquisition rate of the imaging system by the necessary spatial sampling rate. In both the control and tissue cases, very little difference can be seen in the point spread functions of K-space plots even after downsampling the spatial sampling to 0.4 samples per degree, a factor of 8 lower than was acquired. A slight increase in clutter can be observed at this level, but the point spread function is preserved. Beyond this, large angular side lobes are observed around the point target. These correspond to sparse sampling of K-space, where individual lobes can be seen rather than a solid region of interrogation. These artifacts would be unacceptable for clinical imaging and represent a lower bound on angular sampling.

While redundant interrogations of k-space improve the resulting signal-to-noise ratio of the data, it may be desirable to minimize this redundancy in order to achieve a faster sweep based on the expected tissue motion. For example, if a real-time implementation of the imaging system can acquire and process data at a rate of 3 kHz and samples can be acquired at a rate of 0.4 samples per degree as above, after dividing by 12 to fully sample the elevation dimension the minimum sweep time would be 50 ms, limiting maximum tissue motion to around 50 microns over the full extent of the scan. If the system can acquire data faster, additional angular k-space interrogations can be made to provide redundant frequency information through varying clutter.

Figures 18A, 18B:
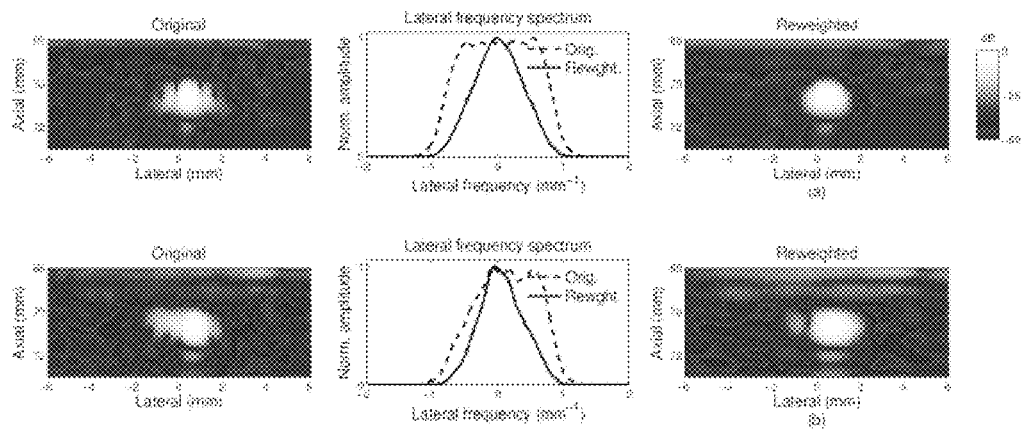
FIG. 18A shows the effect of aperture weighting for a point target without an abdominal tissue layer.
FIG. 18B shows the effect of aperture weighting for a point target with an abdominal tissue layer.

The point targets formed by the swept aperture method more strongly emphasize high spatial frequencies compared to conventional imaging techniques, as shown in FIGS. 18A and 18B. FIG. 18A shows the effect of aperture weighting for a point target without an abdominal tissue layer, and FIG. 18B shows the effect of aperture weighting for a point target with an abdominal tissue layer. A conventional rectangular aperture with equal-sized transmit and receive apertures produce a lateral frequency profile shaped like a triangle, the convolution of the transmit and receive apodizations. In the single aperture case in this paper, with a large transmit aperture and small receive aperture, the expected shape is a trapezoid.

In the swept case, each aperture produces this trapezoid rotated about the origin, summing overlapping trapezoids into a similar trapezoid shape that covers a wider lateral region of k-space. This trapezoid shape is shown in the lateral profiles in FIGS. 18A and 18B. When the data are reweighted to emphasize lower spatial frequencies, increasing the weight of transmit events in the center of the sweep, the conventional triangular shape can be recovered. The resulting point targets show less significant side lobes and a broader main lobe. Whether this shape is more or less desirable is a decision to be made by clinicians based on the resulting texture of speckle and structures in the image.

Figures 19A, 19B, 19C:
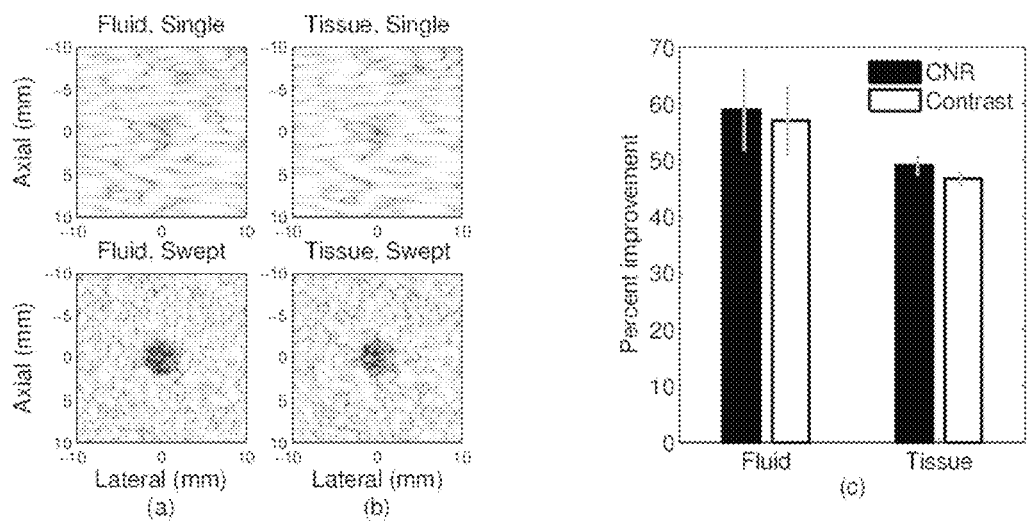
FIG. 19A shows a lesion simulation from the point spread function without an abdominal tissue layer.
FIG. 19B shows a lesion simulation from the point spread function with an abdominal tissue layer.
FIG. 19C shows CNR and contrast percent improvement (paired comparisons between the swept and single apertures) for the fluid and tissue cases, shown with error bars representing one standard error.

The results of lesion simulations (N=1000) using experimental point spread functions (PSFs) convolved with sub-wavelength scatterers and a 5 mm-diameter anechoic lesion are shown in FIGS. 19A-19C. A 50 dB dynamic range is displayed for the lesion images. FIG. 19A shows a simulation from the point spread function without an abdominal tissue layer. FIG. 19B shows a simulation from the point spread function with an abdominal tissue layer. Side-lobes and off-axis clutter would appear as write-in to the lesion. FIG. 19C shows CNR and contrast percent improvement (paired comparisons between the swept and single apertures) for the fluid and tissue cases, shown with error bars representing one standard error. The lesion simulation demonstrates two main points about the swept synthetic aperture. First, the difference between the single and swept apertures in both cases is primarily a result of the resolution improvement. The lesion cannot be resolved in the single aperture case due to the poor main lobe resolution and significant off-axis scattering due to the side lobes, producing extremely low contrast and CNR values. When the resolution is increased, the edges of the lesion are clearly resolved and there is little write-in to the lesion due to off-axis scattering. The percent improvement measured for the two image metrics is directly tied to the relationship between resolution and lesion size. In a larger lesion, the anechoic region could be resolved even at the lower resolution and the improvement observed would be significantly less, although some will be seen regardless due to the improvement in edge resolution.

The second takeaway from the lesion simulation is that even in the presence of the aberrating layer, off-axis scattering and additional clutter do not significantly obscure the lesion. Despite a slight reduction in the mean improvement, roughly the same contrast and CNR improvements are made in the tissue case as in control case. The raised and asymmetric side lobes in the synthesized point spread function do not appear to impact the resulting image quality based on the convolution simulations.

Although only a single 2D image plane was analyzed out of the acquired volume, a matrix transducer could be used rather than a linear transducer. With volumetric data, targets can be imaged outside of the axial-lateral plane, simplifying the need to identify the ideal imaging plane before acquisition. Motion out of the axial-lateral imaging plane could also be tolerated with a matrix transducer, even if only a one-dimensional sweep is desired.

The techniques and system described herein can serve as an investigational tool for large aperture studies. The ability to create apertures of arbitrary shape and extent would be valuable in studying aberration and sources of clutter without the cost of high channel count systems and arrays.

Example 3—Swept Synthetic Aperture Imaging: Ex Vivo Demonstration of Resolution Improvement Ultrasound image quality is inherently limited by the dimensions of the imaging transducer. We describe an adaptively beamformed imaging system designed to image in vivo targets using free-hand motion of the transducer and analyze the potential benefits of such a system. Coherent summation of the recorded echo signals may be limited by clutter induced by aberration and reverberation from tissue layers overlying the target. We demonstrate the feasibility of the swept sensor imaging technique in the presence of these effects by imaging a point target through ex vivo abdominal tissue layers. Using an aperture synthesized from five lateral positions with half-aperture overlap without aberration correction, resolution was improved by 66% and the contrast-to-noise ratio of an anechoic lesion simulated using the experimentally-measured point spread function was increased by 18%. We conclude that the system is valuable for performing both investigational studies requiring large apertures and clinical imaging in challenging imaging environments.

A fundamentally limiting factor in the quality and field of view (FOV) of an ultrasound image is the extent of the transmitting and receiving apertures. Moving the active aperture, either electronically or mechanically, can overcome this limitation given a precise knowledge of the aperture positions.

Decades ago, the first B-mode ultrasound images were formed using a single focused element connected to a moving stage or an articulating arm that swept the probe over the scanning area to form an image, enlarging the FOV from a single scan line to a scan plane [1]. For a phased array scanner that electronically steers the transmit beam, the FOV is determined by the angular sensitivity of the transducer elements, each of which is roughly modeled as a point source radiating a beam within a given opening angle in front of the transducer. While a mechanical arm could extend the FOV for a phased array as well, it is possible to register the overlap between subsequent images from a swept array and stitch them together as a panoramic view of the target area without the use of an external positioning device [2]. Linear arrays electronically sweep an active aperture across the available elements to form an image, providing precise knowledge of the active aperture position relative to the rest of the array. By performing a phased array scan at each of these aperture positions, images with overlapping FOVs can be created and incoherently summed together to reduce speckle variance, a technique known as spatial compounding [3].

Motion can be used to extend the ultrasound image into the elevation dimension as well by translating or rocking the array, each 2-D axial-lateral image plane forming one slice of the final image. Sparse aperture techniques increase the frame-rate of such a scan so that full 3-D images can be acquired in real-time [4]. In addition to pulse-echo imaging schemes, motion has been used to compute tomographic images using an array of transducers swept around a target, producing transmission projections at each aperture position that can be reconstructed into a volume image [5].

In contrast to stacking image planes to extend FOVs or incoherently compounding overlapping regions to reduce speckle, synthetic aperture techniques employ the coherent summation of recorded RF signals in post-processing. Common to all synthetic aperture techniques is the formation of subimages from each transmit/receive event that can be combined into a high-resolution image that is both transmit- and receive-focused throughout the FOV. Each single element across the array can transmit individually, the back-scattered echoes recorded and focused to produce arbitrary transmit and receive foci in post-processing [6]. Multiple elements can be used to transmit a defocused wave and processed in the same way as the single-element case as if the point source were behind the array, increasing the signal-to-noise ratio of the recorded signals [7]. A synthetic aperture can also be formed by treating the focal point of the transducer as a "virtual source", emitting spherically-diverging waves within an angular extent corresponding to the transducer geometry. The recorded echo signals can be refocused in post-processing relative to the virtual source for each transmit event and combined in the areas of overlap [8].

While the axial resolution of the image is determined by the transmitted pulse length, the transverse resolution is determined by the extent of the transmit and receive apertures. The imaging system is described as a spatial bandpass filter and the filter response viewed in the frequency domain, or "k-space" [9]. This framework can be used to predict the response of the imaging system to operations such as translation and rotation for arbitrary array configurations. K-space theory is therefore useful in designing synthetic aperture configurations and will be used in this paper to describe the synthesized aperture.

The "co-array", the 1-D equivalent to the k-space description, has been used to implement a synthetic aperture scan with the same resolution as a full-aperture phased array scan but using a reduced channel count. By strategically choosing transmit and receive sub-apertures electronically translated across the array and re-weighting the final contributions from each, the same k-space coverage and therefore resolution and speckle texture can be attained [10]. Translating and rotating the array allows new regions of k-space to be sampled, increasing the resolution of the system. High-resolution 3-D images have been formed by mechanically sweeping [11] or rocking [12] a linear array through the elevation dimension and combining a volume formed by each using a virtual source in elevation. Volumetric images can also be formed by rotating a linear array using diverging transmit beams [13] or using a helical scan geometry with a single focused element and virtual sources in both the lateral and elevation dimensions [14].

Previous work has studied image quality metrics as a function of aperture size and concluded that using large apertures in vivo can result in improved contrast and resolution even in the presence of clutter [15]. We further improve image quality by using synthetic aperture methods with a matrix transducer and a free-hand scanning technique tracked by an external device, allowing arbitrary interrogation of k-space to form large, coherent 3-D apertures. This method of performing synthetic aperture imaging is similar to the methods employed in sonar and radar [16].

The swept synthetic aperture imaging system according to some embodiments of the invention is detailed in FIG. 9. A matrix array transducer, capable of transmit and receive focusing in both the lateral and elevation dimensions, is mechanically swept over the target and tracked by an external device. An electromagnetic, optical or mechanical tracking device precisely records the 3-D position and 3-axis orientation of the transducer and is calibrated to convert the tracking frame position into array element positions. This information is provided to both the transmit and receive beamforming systems.

The matrix array can use any conventional synthetic aperture scheme to form volume images of the target region of interest. For example, using diverging transmit waves, the receive channel data from each transmit event is recorded and processed by the receive beamformer to produce a single-position radio frequency (RF) subimage of the target. Alternatively, focused transmit beams can be used to improve the receive echo signal-to-noise ratio. The transmit beams are adaptively steered toward the target regardless of probe orientation (within angular sensitivity limits) using the relative position provided by the external sensor. As before, the receive channel data is passed to the receive beamformer and a virtual source synthetic aperture method can be used to reconstruct an RF subimage. A method such as synthetic aperture sequential beamforming [17] could be used to perform two-stage beamforming and remove the need to provide full channel data to the receive beamformer.

Figures 20A, 20B:
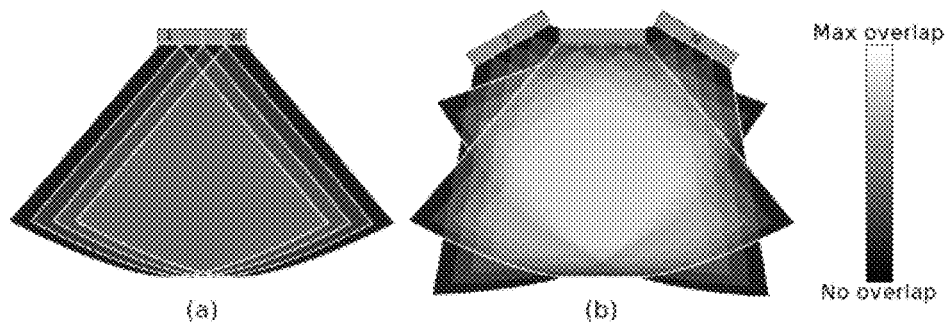
FIG. 20A is a two-dimensional demonstration of scan geometry and synthesized image plane, wherein a synthetic aperture scan is performed to create image planes with overlapping FOVs based on the angular sensitivity of the virtual source (single elements from 1 to M in this example)
FIG. 20B is a two-dimensional demonstration of scan geometry and synthesized image plane, wherein the transducer is translated and rotated through positions 1 to N, acquiring a synthetic aperture subimage at each, to create further overlap in the region of interest.

Given precise knowledge of the position of the transmit and receive elements, the RF subimage created covers the same FOV while the transducer is mechanically scanned to produce different angular interrogations of the target. The RF subimage can be coherently summed with the accumulated RF image from previous transducer positions to produce a high-resolution output image. FIGS. 20A and 20B demonstrate how the scan geometry affects the overlap between the subimages formed from each transmit event and aperture position. FIG. 20A shows a diverging wave synthetic aperture scheme for a single aperture position, transmitting from individual elements 1 to M. Each element has a limited angular sensitivity, creating a fan-beam shape in front of the element that partially overlaps with the reconstructions from the other array elements. FIG. 20B shows the overlap between images from three aperture positions. The transducer is translated and rotated through positions 1 to N, acquiring a synthetic aperture subimage at each, to create further overlap in the region of interest. Depending on the positions chosen, the reconstructed subimages that coincide in space can provide both unique and redundant interrogations. An image reconstructed from all the available data will have varying overlap throughout the FOV and should be compensated appropriately.

Figures 21A, 21B:
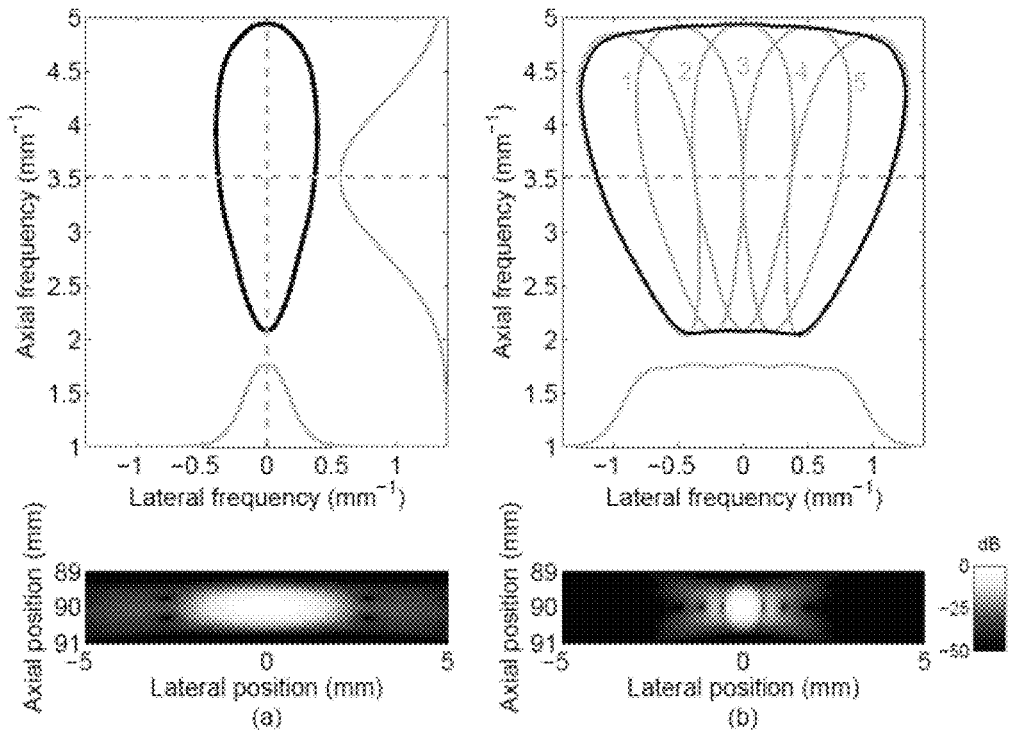
FIG. 21A shows a simulated 2-D point spread function (PSF) and k-space description (−20 dB contour) for a single aperture position.
FIG. 21B shows a simulated PSF and k-space description (individual in gray and summed in black) for five aperture positions, wherein the transducer is rotated about the target point with overlap.

While more overlap is desirable, the overlap between reconstructed subimages from the different aperture positions does not adequately describe the image quality improvement. It is necessary to examine the k-space description of the proposed synthetic aperture to predict the improvement in both resolution and signal-to-noise ratio. FIG. 21A shows a Field II simulation [18] [19] of a point target located at 9 cm depth imaged with a matrix array similar to the Siemens 4Z1c volumetric transducer (Siemens Medical Solutions USA, Inc., Mountain View, Calif.) at 2.8 MHz. The top image shows the −20 dB contour of the k-space calculated using the two-dimensional Fourier transform of the point spread function (PSF). Slices from axial and lateral k-space are shown in gray. The bottom image shows the envelope-detected point target image. The PSF is approximately separable in the axial and lateral dimensions, with the shape of the Gaussian-weighted sinusoid transmit pulse in the axial dimension and a $sinc_2$ shape in the lateral dimension corresponding to the product of the Fourier transforms of the rectangular transmit and receive apertures. Looking only in the positive temporal frequency half-plane, the k-space is therefore Gaussian in the axial frequency dimension and approximately triangular in the lateral frequency dimension, shown by the profiles in gray. The product of these two shapes gives a "teardrop" shape that describes the axial and lateral spatial frequencies imaged by the system.

As the transducer moves relative to a target, the k-space region covered by the imaging system rotates about the origin accordingly. FIG. 21B shows the k-space description (individual in gray and summed in black) for five aperture positions as the transducer is rotated about the point target with angles of [−12, −6, 0, 6, 12] degrees at a fixed radius. This roughly corresponds to a shift of half the aperture length, creating significant overlap between consecutive imaging positions. Due to the Fourier transform relationship, a rotation of the imaging frame corresponds to a rotation of k-space, represented by the five numbered teardrop shapes outlined in gray. The linearity of the imaging system means that the sum of these individual shapes gives the total k-space representation, shown in black, covering a larger lateral spatial frequency extent than a single position. This total extent determines the highest spatial frequencies present in the image and therefore dictates resolution, as shown by the simulated point target.

The focused backscattered echoes can be adaptively weighted in various ways to improve image quality. For each transmit event, data can be weighted on the level of each receiving element or on all elements together. An assumed k-space profile based on transmit pulse frequency and bandwidth and the spatial extent of the element can be formed for each transmit event (likely a trapezoidal shape laterally and Gaussian axially). This profile can be transformed based on the measured probe movement relative to the imaging target and summed with the profiles from all imaging positions to predict the resulting k-space magnitude profile for the image. This profile can be used to form an inverse filter in order to reweight the recorded echoes to produce an arbitrary k-space profile (e.g. the conventional triangular shape, a flat profile or a transverse oscillation profile), directly corresponding to the point spread function of the imaging system. Properties of the point spread function such as side lobe characteristics and symmetry can be controlled using this manner of apodization.

Redundancy in k-space between multiple tracked acquisitions can be used to overcome issues of data quality. Overlapping regions in k-space can be adaptively combined using image quality metrics such as signal-to-noise ratio, correlation coefficient, signal amplitude or spatial coherence. Weighting of the data can be performed either in the time domain or the frequency domain, meaning the weightings can vary spatially and with frequency. Spatially varying filters can be applied to discard data corresponding to shadowed or clutter-filled regions that are more clearly viewed from other imaging positions. Data can be acquired in such a way as to maximize redundancy in k-space through different acoustic windows, steering plane waves or focused transmit events to sample different angular regions of k-space from each position in physical space the probe is moved to. Data that cannot be used to improve the synthetic aperture image can be discarded or used to produce images for incoherent compounding, taking advantage of the decorrelation rate of speckle relative to the swept aperture positions.

The relative amplitudes of the spatial frequencies present, and the topography of k-space, determine the texture of imaged targets. For example, a system with only high-lateral-frequency components would represent a point target as a sinusoidal oscillation rather than a sharp point. It is also possible to weight the data from individual aperture or element positions to reshape k-space, for example weighting the apertures numbered 1 through 5 with the vector [1, 2, 3, 2, 1] to emphasize low lateral spatial frequencies and create a more conventional lateral transfer function with a triangular shape rather than the trapezoid shown in gray in FIG. 21B. While it is theoretically possible to completely sample a region of k-space with non-overlapping apertures, redundant interrogations from overlapping apertures increase the signal-to-noise ratio at each spatial frequency. Regions that overlap in space in FIG. 20B may either represent new spatial frequency information, producing improved resolution, or redundant interrogations, improving signal-to-noise ratio. With the synthetic aperture data set, it is also possible to selectively perform spatial compounding (i.e. echo summation after detection) using data that do not overlap in k-space to smooth speckle regions while coherently compounding data (i.e. summing RF signals before detection) from all regions of k-space for targets where high-resolution imaging is desired [20] [21].

While the example presented in this paper rotates the array only in the axial-lateral plane, motion in the elevation dimension may also be desirable to increase the corresponding elevation resolution. Using the sparse aperture ideas presented in [4], a scan that samples both the lateral and elevation frequency spaces could be constructed without an excessively long scan time.

Data were collected ex vivo to evaluate the effectiveness of synthesizing large apertures using the method in the presence of clutter from aberration and reverberation. The Siemens ACUSON SC2000 ultrasound system (Siemens Medical Solutions USA, Inc., Mountain View, Calif.) and 4Z1c volumetric transducer were used with a custom sequence to collect individual receive channel I/Q data for transmit events on 3×3 element sub-apertures across the lateral and elevation extents of the array. Acquired data were stored with corresponding transducer positions for offline processing.

Imaging was performed in a tank filled with a solution of 1-propanol and water to produce a fluid with a sound speed of approximately 1540 m/s at room temperature (approximately 23 C) [22]. The imaging target was a custom agar phantom with a 0.25 mm diameter sapphire embedded inside, located approximately 8.9 cm from the transducer face. The desired motion of the transducer was a lateral translation of half the length of the aperture followed by a rotation to point the array at the point target, producing a total of five aperture positions as in FIG. 21B. The transducer was mounted on a rotation stage coupled to a three-axis translation stage and controlled by a Newport MM3000 motor controller (Newport Corporation, Irvine, Calif.), allowing precise position and orientation control of the transducer. This motion was implemented with a lateral-axial correction using the translation stage to account for the estimated distance between the center of rotation (the mounting point on the rotation stage) and the face of the array.

Immediately after the point target control acquisition and without moving the target fixture, the same sequence was repeated with the addition of ex vivo tissue directly in front of the transducer. Approximately 10 cm×20 cm of canine anterior abdominal wall was harvested, consisting of skin (hair removed), subcutaneous fat, fascia, abdominal muscle (including rectus abdominus and transverse abdominus) and peritoneum. Adipose tissue underlying the peritoneum was removed. The overall thickness, approximately 2 cm, and elasticity were conserved by mounting the tissue immediately following excision onto a plastic frame and submerging the structure in the tank. The frame was designed with a curve to match the arc swept by the transducer in order to maintain contact between the array and the tissue, but a separation on the order of 1 mm may be present at certain scan locations due to variations in the tissue height. The depth of the point target relative to the transducer remained the same as in the fluid path experiment. A second set of both control and ex vivo data was acquired using the same point target at a depth of approximately 7.3 cm with a different sample of excised canine tissue.

Synthetic aperture beamforming was used to produce volumetric RF data for each array position on a common Cartesian grid centered on the point target. To compensate for error in the lateral-axial correction step of the scan described above on the order of 1 mm, image volumes were shifted to align the peak of the point target in each control (fluid path) image. The same correction factor was applied to the ex vivo tissue data so that any remaining alignment error was attributable to aberration, sound speed error or refraction through the tissue layer.

An axial-lateral plane for 2-D PSF analysis was chosen by finding the location of the peak value in the elevation dimension from the envelope-detected data. Axial-lateral RF PSFs were extracted from the beamformed data sets in this plane using a 5 mm axial×11 mm lateral window. K-space content was calculated using a two-dimensional Fourier transform of the extracted RF PSF. Lateral PSF profiles were taken from the center of the point target both axially and in elevation and were normalized to the peak brightness value. The full-width at half-maximum (FWHM) was measured as the distance between the −6 dB points of the lateral profile.

The effects of aberration were analyzed both between receive channels on the array and between aperture positions. Cross-correlations between receive channel echo pairs were analyzed for the center single-aperture position. Arrival time differences across the aperture were calculated using an anchored cross-correlation between the point target signals received on each channel and a reference channel. In order to prevent discontinuities in the measured aberration profile due to distorted receive waveforms [23], a Gaussian weighting with a FWHM of one wavelength was applied to the cross-correlation values. This operation was performed for the control and ex vivo cases for both trials.

The peak-finding technique used to calibrate the control cases was used to analyze the misalignment between aperture positions caused by the tissue layer. The peak of the 3-D envelope-detected signal was found for each aperture position and all volumes were aligned by translation. This operation is an approximation to a true aberration correction that would involve refocusing using a bulk delay and a steering delay. For small errors, the effects of refocusing and rotation are negligible compared to the gains made by translation in coherently aligning the received signals.

To investigate the improvements made by using the synthesized PSF on clinically relevant imaging targets, the experimentally measured axial-lateral PSF was convolved with randomly positioned sub-wavelength scatterers of varying scattering amplitudes and an anechoic region of 5 mm diameter was placed in the center. Values for contrast-to-noise ratio (CNR) were averaged over 1000 speckle realizations using the same experimental point spread functions. Contrast-to-noise ratio is given by $$CNR = \frac{|\mu_o - \mu_i|}{\sqrt{\sigma_o^2 + \sigma_i^2}} \quad (3.1)$$

where $\mu_o$ and $\mu_i$ are the mean values and $\sigma_o$ and $\sigma_i$ are the standard deviations inside and outside the region of interest. The region of interest was the 5 mm circular region where no scatterers were specified. The region outside the lesion used as a background measurement was a 5 mm circle at the same depth, offset laterally 1 mm from the lesion. Contrast-to-noise ratio is reported as percent change from a single aperture position for a given imaging target, post-processing method and trial for each speckle realization.

Figure 22:
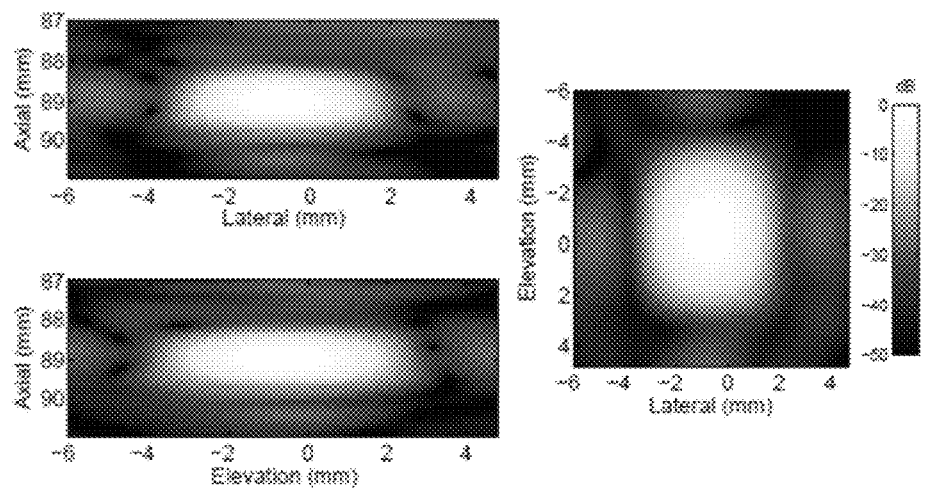
FIG. 22 shows image slices for three orthogonal planes through the center of an experimental point target in control setup.

A sample single-position image from the control experiment is shown in FIG. 22 as slices through the center of the point target in each plane of 3-D space. The main lobe and side lobes in the lateral and elevation dimensions are visible within the reconstructed volume. Resolution in the lateral and elevation dimensions is approximately the same, while resolution is higher in the axial dimension. Background clutter is generated from the interface of the agar phantom that the point target is embedded in and for the following analysis is considered part of the PSF.

Figure 23:
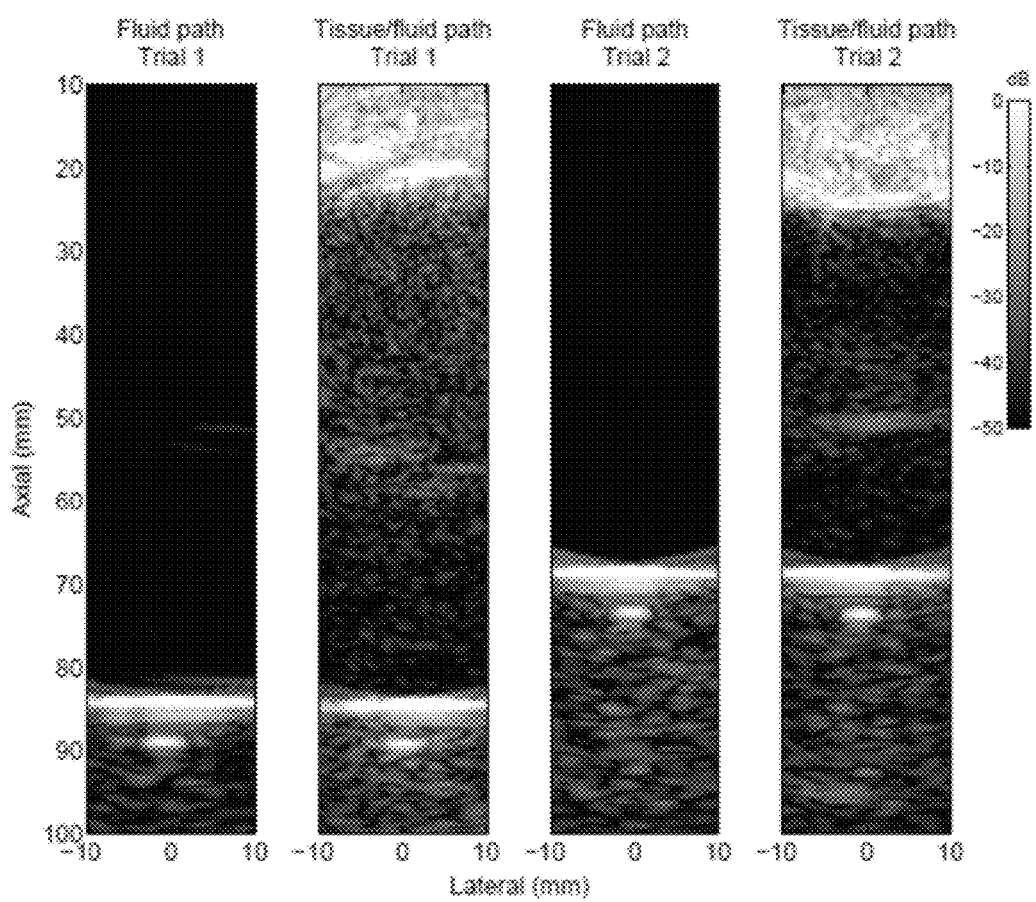
FIG. 23 shows B-mode images in the axial-lateral plane for the control (fluid path) and experiment (tissue/fluid path) setups for both trials.

The axial-lateral plane for a single position in the control and tissue experiments is shown in FIG. 23 with all values normalized to the point target brightness. FIG. 23 shows B-mode images in the axial-lateral plane for the control (fluid path) and experiment (tissue/fluid path) setups for both trials. Ex vivo tissue extends to around 2 cm depth and generates clutter through the remaining fluid path. The distance from the transducer to the target is 89 mm in trial 1 and 73 mm in trial 2. The top of the image shows the location of the tissue (if present), followed by a fluid path without scatterers. The top layer of the agar phantom is visible as a strong horizontal specular reflector (above the displayed threshold), followed by the comparably weaker point target underneath. The top agar interface produces reverberation clutter on the order of −30 dB with respect to the point target.

The ex vivo tissue layer placed between the transducer and the point target serves as clutter-generating media to produce reverberation, attenuation and aberration that will degrade the resulting image quality. In the cases with the tissue layer, reverberation clutter created by the tissue structure is visible throughout the image but the amplitude is below −30 dB at the target depth. In the experimental case for both trials, there is a strong coherent reverberation artifact observed in the fluid path corresponding to particularly bright layers in the tissue.

Figure 24A:
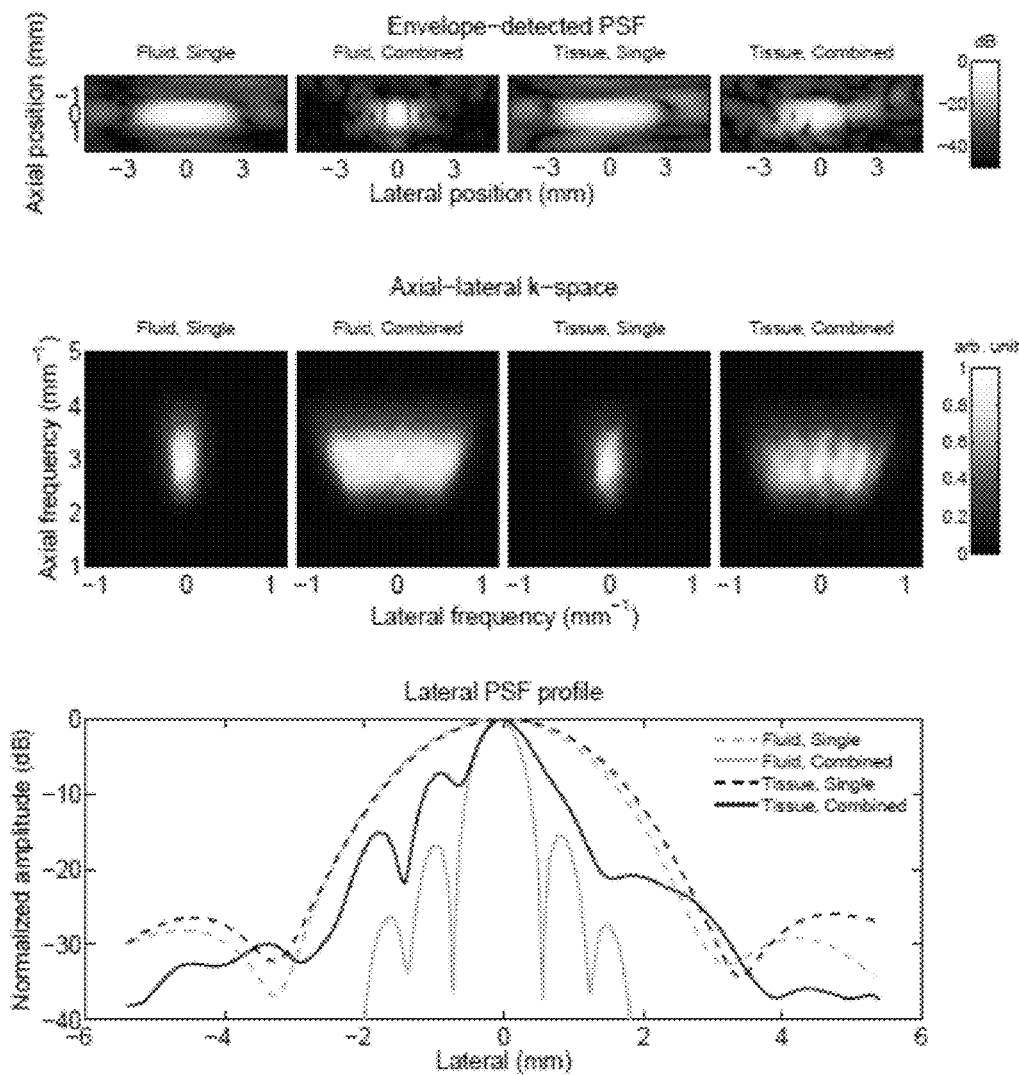
FIG. 24A shows the envelope-detected PSF, the k-space measured by the two-dimensional Fourier transform, and lateral profiles from the control and ex vivo tissue cases using a single aperture and the synthesized aperture for trail 1.
Figure 24B:
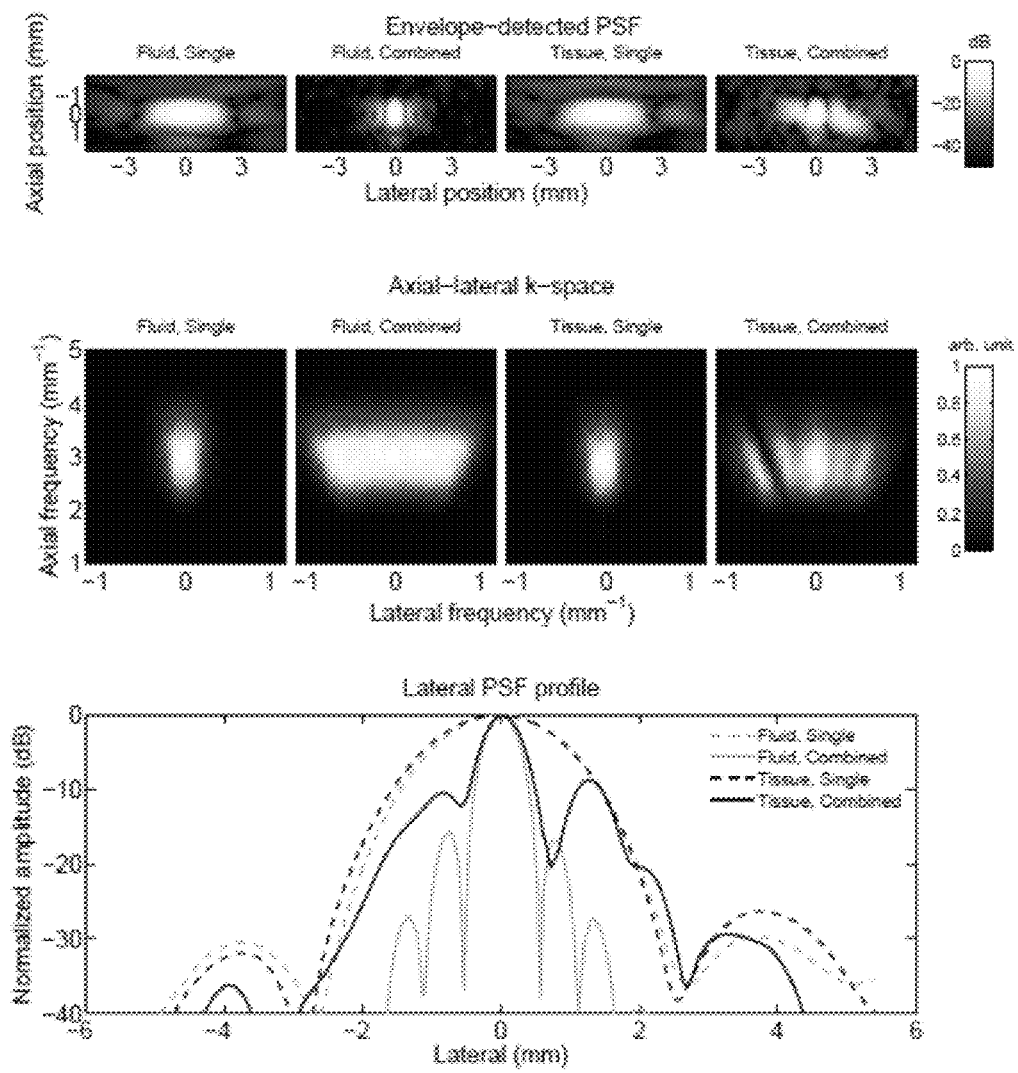
FIG. 24B shows the envelope-detected PSF, the k-space measured by the two-dimensional Fourier transform, and lateral profiles from the control and ex vivo tissue cases using a single aperture and the synthesized aperture for trail 2.

For both the control and the ex vivo tissue case in each trial, the axial-lateral PSF was extracted from the center single-position image and the synthesized image. The synthesized image was made up of the five positions, creating an effective aperture of roughly three times the lateral length. The elevation dimension was excluded from analysis because the translation and rotation of the transducer was limited to the axial-lateral plane. FIGS. 24A and 24B show the envelope-detected PSF, the k-space measured by the two-dimensional Fourier transform, and lateral profiles from the control and ex vivo tissue cases using a single aperture and the synthesized aperture for both trials. The top row shows the envelope-detected PSF for the control (fluid path) and tissue-layer experiment (tissue and fluid path) for a single aperture position and combined aperture positions. The middle row shows k-space plots corresponding to the analytic RF signal for each of the PSFs. The bottom row shows the lateral PSF measured through the center of the target and normalized to the peak amplitude.

The synthesized PSF in the control case closely matches the simulated PSF of FIG. 21, demonstrating a 74% and 72% improvement in the measured FWHM of the PSF in trials 1 and 2 respectively. The synthesized PSF in the experimental case demonstrates a similar resolution improvement, showing a 66% and 68% decrease in the FWHM in trials 1 and 2 respectively. However, below the −6 dB threshold, the ex vivo tissue PSF shows effects of aberration that distort the expected lateral profile and raise side-lobe levels. K-space reveals that the frequency content from each acquisition is only partially coherent, resulting in destructive interference when the RF signals corresponding to overlapping regions are summed. The increase in resolution corresponds to the total k-space width, which is preserved despite aberration, while the increased side lobe levels and distortion correspond to the dynamics of the frequency spectrum, which have suffered from destructive interference between individual aperture positions due to the aberrating tissue layer.

Figure 25:
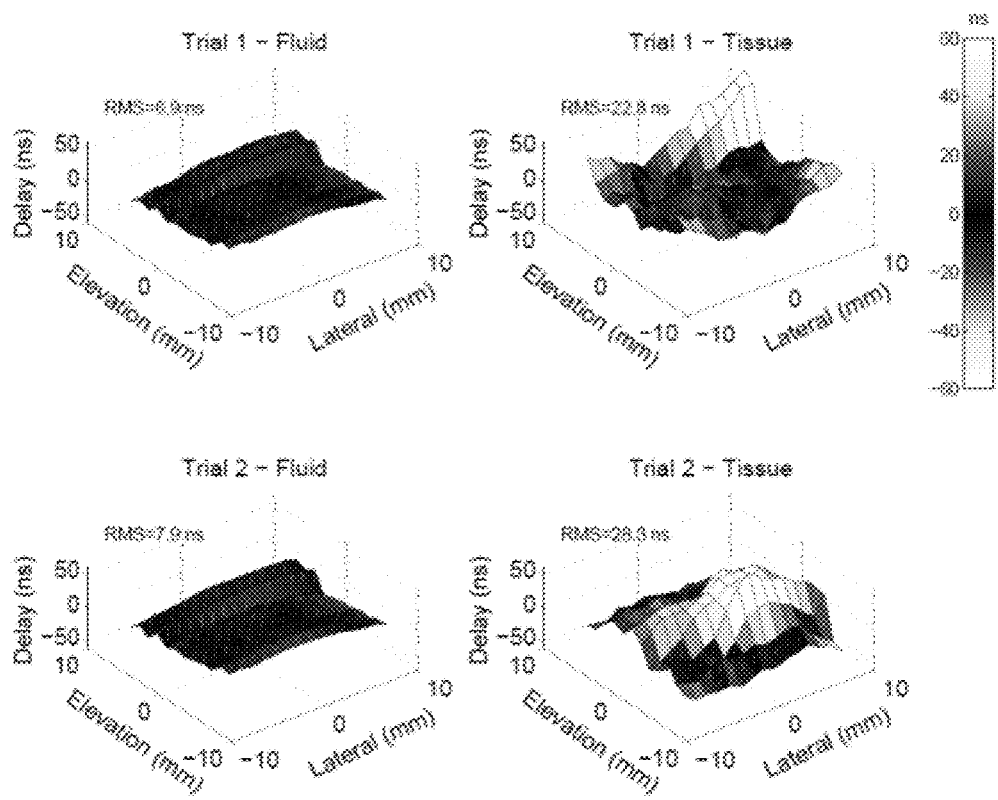
FIG. 25 shows the aberration profile in two dimensions with the median value subtracted off to leave only variations in arrival time.

Aberration causes misalignment in the arrival times of the backscattered echoes and prevents the coherent summation necessary for improved image quality. FIG. 25 shows the aberration profile in two dimensions with the median value subtracted off to leave only variations in arrival time. Arrival time deviation is shown for the center-position single aperture, and the root-mean-square (RMS) value in nanoseconds is reported for each case. The left-hand side plots are for the control case, showing low-magnitude arrival time errors. The right-hand side plots are for the experimental case, demonstrating phase errors across the 2-D aperture created by the tissue layer. The control case in both trials shows small arrival times differences across the array, with root-mean-square (RMS) values of 6.9 ns and 7.9 ns. In the presence of the aberrating tissue layer, RMS error increases to 22.8 ns and 28.3 ns.

Figures 26A, 26B:
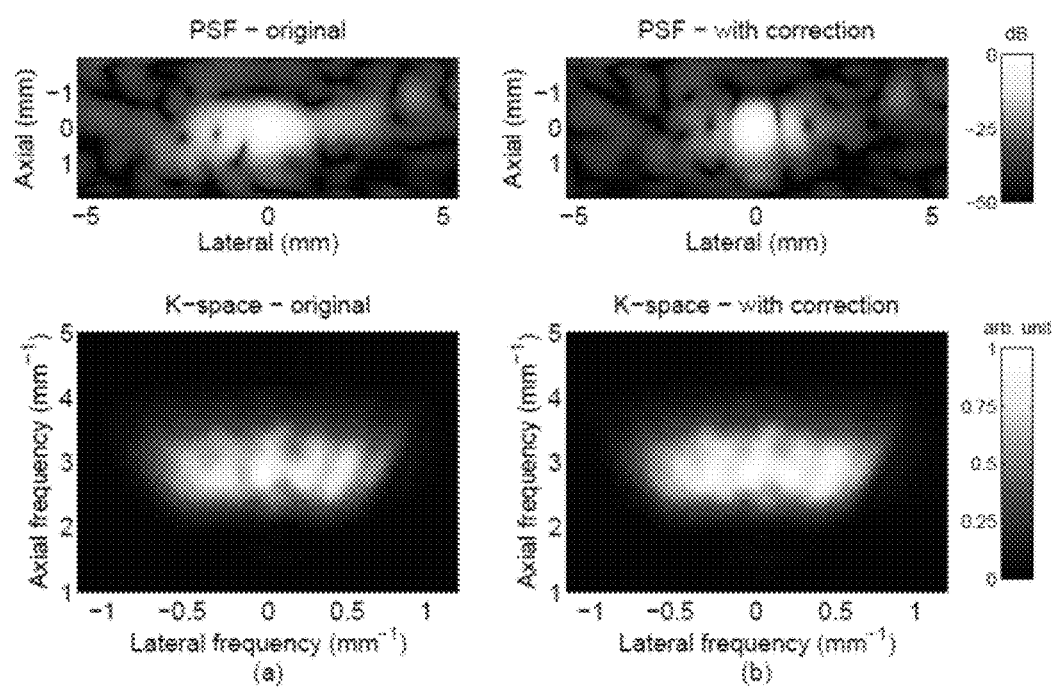
FIG. 26A shows the PSF and k-space description for the experimental case from trial 1, demonstrating the effects of aberration between aperture positions.
FIG. 26B shows the PSF and k-space description for the experimental case from trial 1 after performing a translation of each subimage to coherently align the point target, reducing the interference and lowering the side lobe levels of PSF.

FIG. 26A shows the PSF and k-space description for the experimental case from trial 1, demonstrating the effects of aberration between aperture positions. The combined k-space profile shows gaps between the lobes corresponding to each aperture position, indicating that aberration has distorted the phase and caused destructive interference. FIG. 26B shows the same data after performing a translation of each subimage to coherently align the point target, reducing the interference and lowering the side lobe levels of PSF.

Figures 27A, 27B:
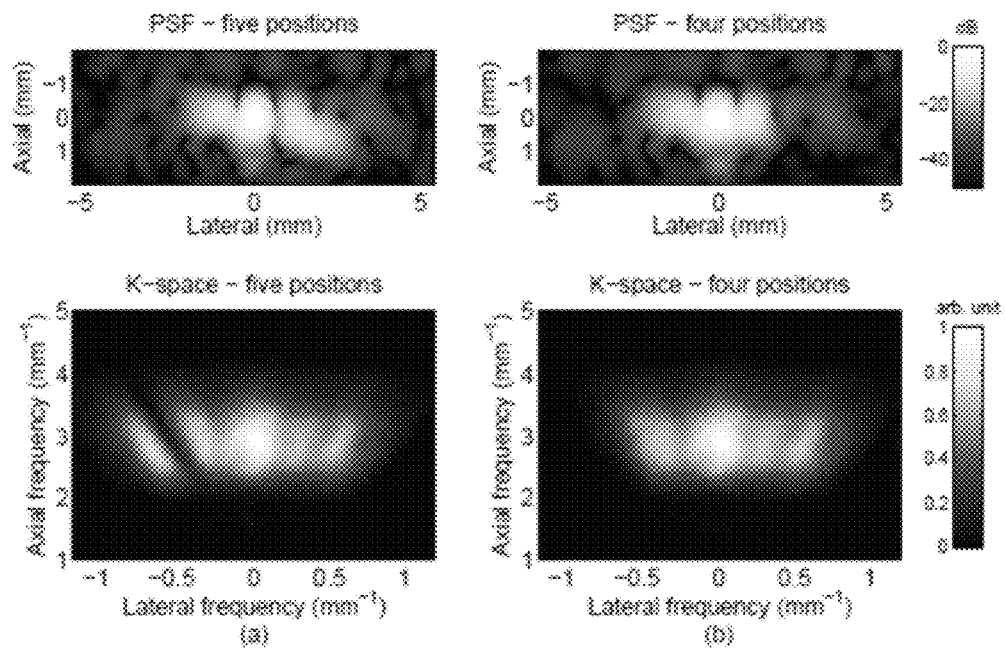
FIG. 27A shows the PSF and k-space description for the experimental case from trial 2, with observed misalignment in one aperture position.
FIG. 27B shows the synthesized aperture from four positions, with the errant aperture position omitted.

In trial 2, one of the five aperture positions creates a subimage that is misaligned and destructively combines with the others to create a strong side lobe in the PSF shown in FIG. 27A. The effect is clearly visible in k-space, creating a gap between the main spectrum and the misaligned aperture where destructive interference has occurred. It is important to note that the isolated region of the spectrum is not merely shifted, but its extent has been reduced by the destructive interference. In lieu of performing aberration correction to realign the data, interference can be avoided by omitting the problematic aperture position. FIG. 27B shows the synthesized aperture from four positions, with the errant aperture position omitted. The total extent of k-space (resolution) and side lobe levels are both reduced. While the observed resolution may be slightly higher in the five-position case because half an aperture of lateral extent has been added, the image quality is improved in the four-position case and the large side lobes are no longer present.

Figures 28A, 28B:
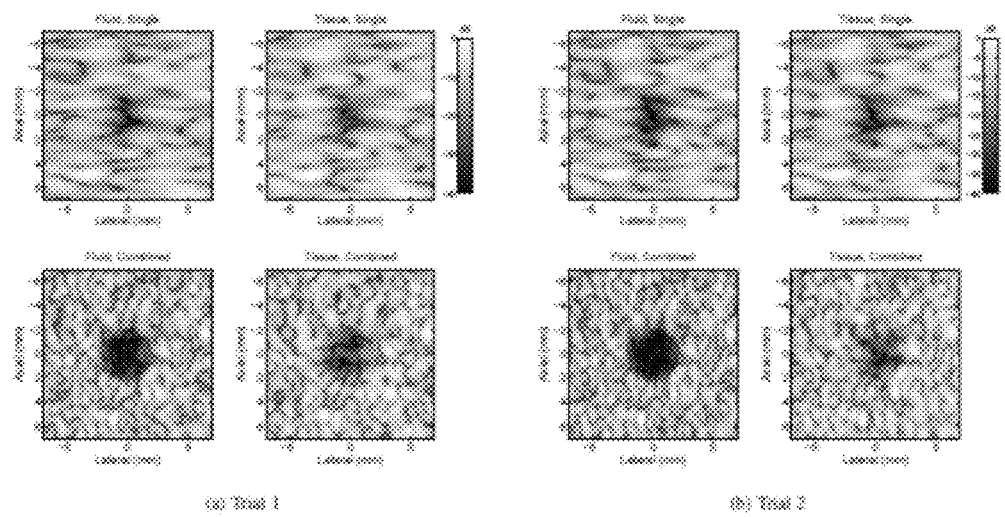
FIG. 28A shows sample images from a single speckle realization for the single aperture and combined aperture in the control and ex vivo tissue cases in trial 1.
FIG. 28B shows sample images from a single speckle realization for the single aperture and combined aperture in the control and ex vivo tissue cases in trial 2.

Sample images from a single speckle realization are shown in FIGS. 28A and 28B for the single aperture and combined aperture in the control and ex vivo tissue cases. The figures show example simulated 5 mm-diameter anechoic lesion targets using experimentally measured PSFs from trial 1 (FIG. 28A) and trial 2 (FIG. 28B). The top row shows a lesion simulated with control and ex vivo tissue PSFs for a single aperture position. The bottom row shows the lesion simulated with control and ex vivo tissue PSFs for a combined aperture, showing the effect of improved resolution on target visibility. In both the control and tissue cases, the anechoic lesion is poorly visualized using a single aperture position due to the lateral resolution of the imaging system. Using the combined aperture increases the visibility of the lesion, even in the case of an aberrated PSF where additional off-axis clutter is written into the anechoic region. A signal-to-noise ratio (SNR) for lesion detectability is proposed in [24] that accounts for the importance of resolution on the visibility of a target, multiplying (3.1) by the number of resolution cells within the region of interest. Even without an increase in CNR, this SNR metric predicts significantly improved visibility in the combined aperture case due to the increased resolution. This is particularly evident in FIG. 28B where even though the measured CNR is roughly the same for both apertures, the decrease in speckle texture size with the synthesized aperture makes the lesion more easily distinguished from a dark speckle region.

Figures 29A, 29B:
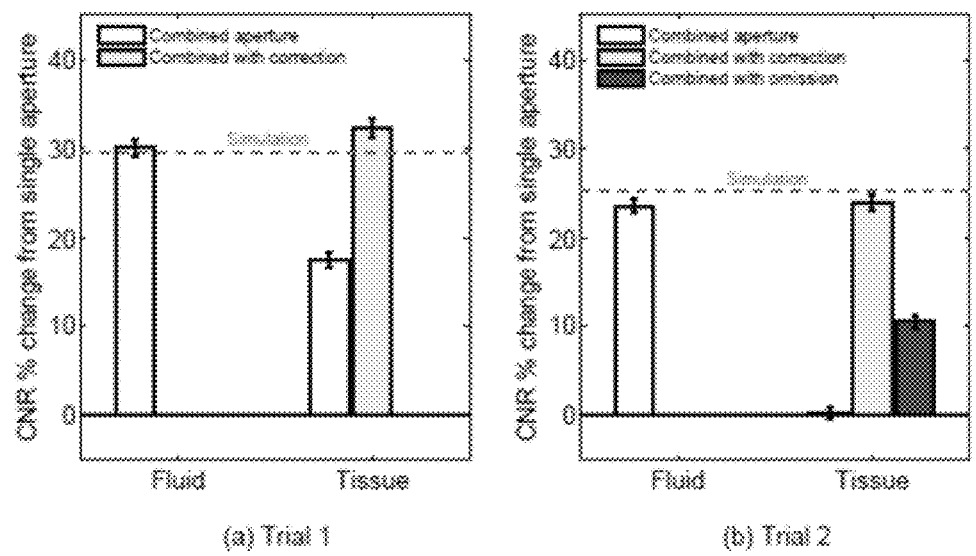
FIG. 29A shows the results of the lesion simulation for each tested PSF for trial 1.
FIG. 29B shows the results of the lesion simulation for each tested PSF for trial 2.

FIGS. 29A and 29B show the results of the lesion simulation for each tested PSF, grouped by trial and target. The figures show the percent change in contrast-to-noise ratio relative to a single aperture position for simulated 5 mm anechoic lesions using experimentally measured point spread functions, N=1000 speckle realizations. Bars are plotted with error bars representing plus or minus one standard error. Optimal alignment of the point target from the five aperture positions was performed in the tissue case to correct for aberration and refraction (second bar). In trial 2, one misaligned aperture position was omitted from the sum without further correction (third bar). Matched simulation results are shown as a dashed line on each plot for reference. A matched point target simulation was performed as in FIGS. 21A and 21B and the same lesion simulation procedure was followed to give an ideal CNR improvement, marked with a dashed line on the graph. A 30% and 24% improvement in CNR are measured for the control case in trials 1 and 2 respectively, in good agreement with the simulation results. With the tissue layer in the imaging path, an 18% improvement in CNR is observed in trial 1, but no improvement is observed in trial 2. In this case, where the subimage from the misaligned aperture position destructively interferes with the other subimages, simply omitting this position improves the measured CNR without further aberration correction. The best results in the ex vivo tissue cases are achieved by coherently aligning the subimage produced by each aperture, as if performing aberration correction, producing results that are similar to the control cases.

Aberration correction can be performed by treating the tissue layer as a phase screen in front of each element of the array, adjusting the focal delays for each aperture position on transmit and receive using cross-correlation across the array [25] or optimizing a quality factor such as point target size or speckle brightness [26]. As the effective aperture size grows, the magnitude of and the degradation caused by the aberration are expected to increase [27], [28]. However, a larger aperture can capture a wider extent of the returning wavefront and enable more accurate aberration correction [23], [29]. Where aberration correction is not possible, perhaps due to computational complexity or inadequate channel signal-to-noise ratio, using a large aperture allows the omission of apertures that are not coherent with the accumulated image or the use of a combination of coherent and incoherent compounding in order to take advantage of all acquired data [21].

In both trials, each aperture position is individually corrupted by aberration that causes degradation within each subimage. Because the relative arrival time error is only a small fraction of the wavelength, only a small amount of blurring and distortion are seen in the subimage. The effect of a constant delay across the aperture caused by a sound speed error or an effective steering caused by refraction results in only a small focusing error and has little effect on the reconstructed subimage. A more significant image degradation is seen when coherently combining the subimages to create a high resolution image. Due to the rotation of the aperture position, a small axial misalignment in a subimage due to a constant delay or refraction becomes a lateral error that distorts the lateral PSF. The destructive interference seen in k-space in trial 2 is the result of this type of error and severely impedes the gains made with the synthesized aperture. Because aberration correction is not always possible due to low signal strength and high clutter levels, it is important to note that gains in image quality can be made using the swept aperture system both with and without compensation.

The presented results also motivate the need for precise position and orientation sensing as part of the swept sensor imaging system. Just as in the case of aberration, a single misaligned aperture can destructively interfere with the other acquired signals and cause degradation in the resulting image. The sensitivity of the system to motion error is related to the resolution in each dimension, making the system more tolerant to lateral and elevation error than axial error. An additional challenge in positioning is the registration from the face of the array, the acquired signal frame, to the positioning device coordinate system. Without proper calibration, the reconstructed imaging frame will suffer from focusing errors due to the distorted geometry.

A scanning scenario according to some embodiments of the invention involves sweeping the probe in the axial-lateral plane, as in this paper, over a 5 cm arc to image an abdominal target at a depth of around 9 cm, increasing the angular interrogation from 11.4 degrees for a single aperture to 31.8 degrees for the synthesized aperture. Assuming the operator can move the transducer at a rate of 50 cm/s, the total scan duration is 0.1 s. The maximum pulse repetition frequency for this imaging depth is 8.5 kHz. In contrast to the experiment presented herein in which the full aperture was sampled at each position, a single transmit event occurs at every position during the continuous sweeping motion. This transmit event could be from a single element, small defocused subaperture, plane wave, or the full focused aperture (steered toward the target). The region of k-space interrogated with each transmit and receive event varies depending on the implementation scheme, but the total extent of k-space is determined by the motion of the transducer as described above. The element pitch on the array is approximately 375 µm, meaning that in the 117 µs that the echoes for a single transmit event take to return, the array has only moved 58.5 µm and there will not be significant motion artifacts. To create a synthetic transmit aperture with the same 375 µm pitch at this sweep rate, the required pulse repetition frequency is 1.3 kHz for a total of 133 transmit events. Increasing the sampling rate would provide more redundant interrogations and increase the electronic signal-to-noise ratio in the synthesized image.

The axial dimension is most sensitive to tissue motion artifacts due to the high-frequency pulse. Assuming axial tissue motion of around 1 mm/s, a relatively high estimate for cardiac-induced motion in the abdomen during a breath hold [30], and the scan described above, the timing error throughout the duration of the scan is approximately 132 ns, less than one-third of the period of the transmitted pulse. This assumes a monotonic displacement is an upper bound on the expected motion error, and the effects could be mitigated by using a lower-frequency transmit pulse. In most cases, the motion error is expected to be small enough that it does not require compensation. The effect of motion in the lateral and elevation dimensions depends on the PSF width and therefore the effective aperture size [31]. For the proposed scan, a total lateral motion of 0.1 mm, assuming the same 1 mm/s rate, is insignificant compared to the synthesized 1 mm lateral PSF and likely does not require motion correction.

The swept aperture system is also a powerful tool for investigational work requiring unconventional array sizes or shapes. As in [15], data could be processed with varying apodizations to study the effect of aperture size and weighting with matched in vivo data sets. The large spatial extent of the data sets, including interrogations from numerous angles, could provide insight into clutter and serve as a platform to test new adaptive algorithms to remove it. The technology gives new capabilities to track motion from multiple angles and to compensate the resulting images for both target and transducer motion. The ability to create arbitrary array patterns and to collect full synthetic aperture data sets allows great flexibility in asking fundamental questions about acoustics and image quality that could otherwise only be studied by constructing these arrays at great expense or in simulation.

Example 4—Synthetic Tracked Aperture Imaging Utilizing Multiple Ultrasound Probes The aperture size of ultrasound beamforming is an important factor to determine the image quality of ultrasound imaging, and the bigger the aperture size, the higher the image resolution that can be expected. In sequential beamforming, specific aperture size is used in transmit and receive beamforming. Synthetic aperture is a technique which synthesizes multiple sub-apertures to finally reconstruct a high resolution image. However, when a single ultrasound array probe is used, the maximum available aperture size is limited by the physical size of the ultrasound probe. A large aperture is desired when the region of interest is located in the deep region. Therefore, when the physician needs to scan a thick target such as an obese patient, the technique described herein can uniquely provide a high resolution ultrasound image, which cannot be achieved with a conventional system.

Therefore, according to some embodiments of the invention, multiple ultrasound probes are used, and the sub apertures from the probes are synthesized into a wider aperture, which can generate a high resolution ultrasound image. Multiple probes are placed on the subject's surface, and the positions of the probes are tracked using various tracking systems. As a particular example, a robot arm can be considered as a mechanical tracker, which also can provide a motion to the probe to expand the aperture further. When synthetic aperture beamforming is applied, sub-apertures from each pose can be synthesized while the tracking information is used to identify each ultrasound image coordinate system.

Figure 30:
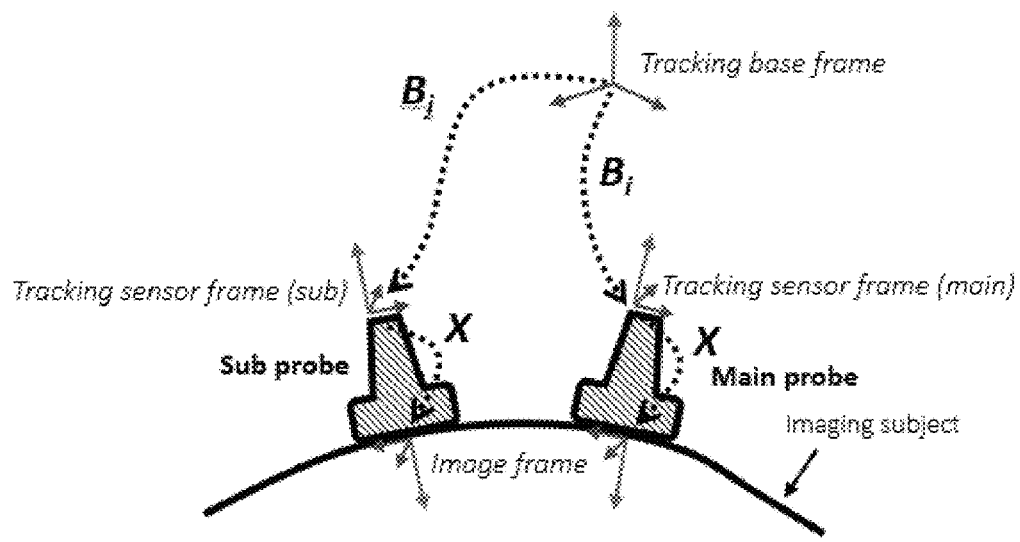
FIG. 30 illustrates synthetic tracked aperture imaging utilizing multiple ultrasound probes, wherein a single tracking base is used for multiple tracking sensors.
Figure 31:
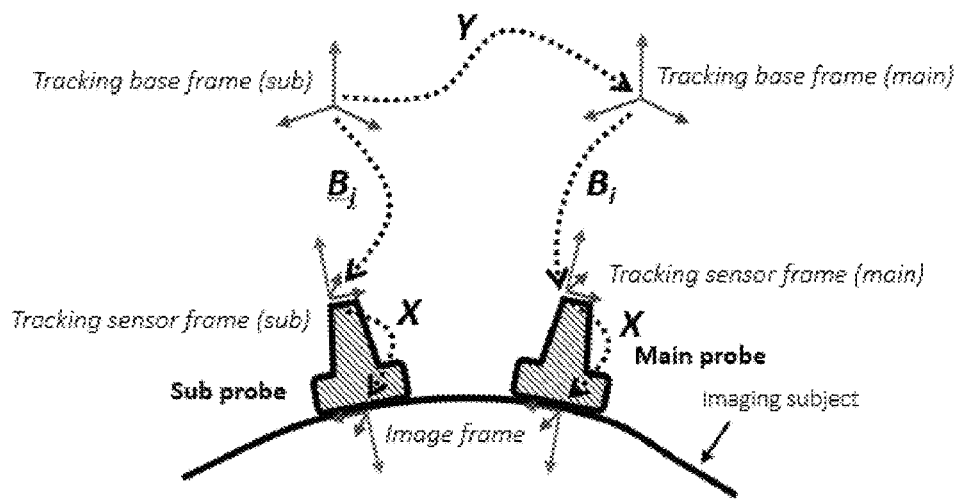
FIG. 31 illustrates synthetic tracked aperture imaging utilizing multiple ultrasound probes, wherein each tracking sensor has its own tracking base.

As the general concept, two tracking configurations can be considered. The first configuration is that two probes are tracked from a single tracking base. This is illustrated in FIG. 30. Each probe has its unique rigid-body transformation $B_i$ and $B_j$ from a single base, while the transformation between tracking sensor frame and ultrasound image frame X is a constant matrix. Thus, the ultrasound image frame of each pose can be expressed as $B_iX$ and $B_jX$. In the beamforming process, these ultrasound image frames will be transformed into a single image frame, and this image frame will be regarded as beamforming geometry. The second configuration is a case that each tracking sensor has its own tracking base, as shown in FIG. 31. Since the tracking bases are separated, in addition to the relationships described for the single tracking base configuration, an additional transformation between two tracking base frames Y will be introduced. Y can be calculated, and its calibration stream is described in [1].

Figures 32A, 32B:
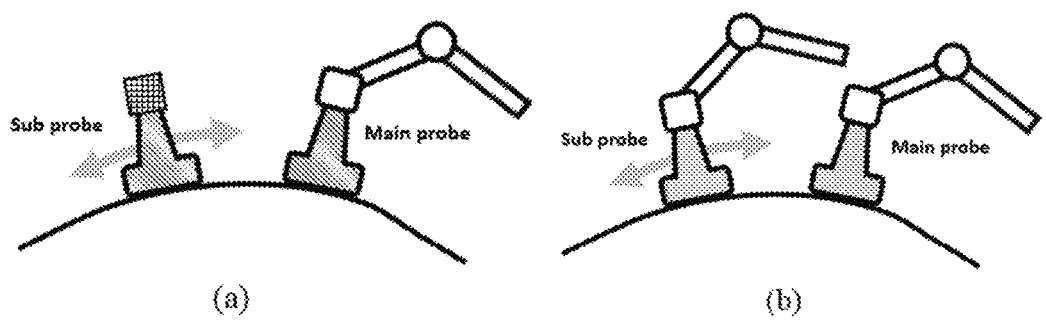
FIG. 32A shows synthetic tracked aperture imaging utilizing dual ultrasound probes, wherein the main probe is fixed, and the sub-probe can be swept freehand.
FIG. 32B shows synthetic tracked aperture imaging utilizing dual ultrasound probes, wherein two robot arms are used.

Here, the scanning using two ultrasound probes is discussed (FIG. 6). The most basic configuration is simply placing two probes, a sub probe and a main probe, in contact with a region of interest and processing data without moving the probes. In this case, the relative position of two position becomes very important for the image quality. Moreover, the sub probe can be swept to extend the aperture size more. Both freehand tracking and autonomous robotic tracking can be used to move the sub probe. At that time, the main probe with a tracker can be fixed using a passive arm. FIG. 32A illustrates a co-robotic freehand configuration for synthetic tracked aperture imaging utilizing dual ultrasound probes, and FIG. 32B illustrates an autonomous configuration employing two robot arms. The trajectory of motion can be more easily controlled using the autonomous configuration.

Figures 33A, 33B, 33C:
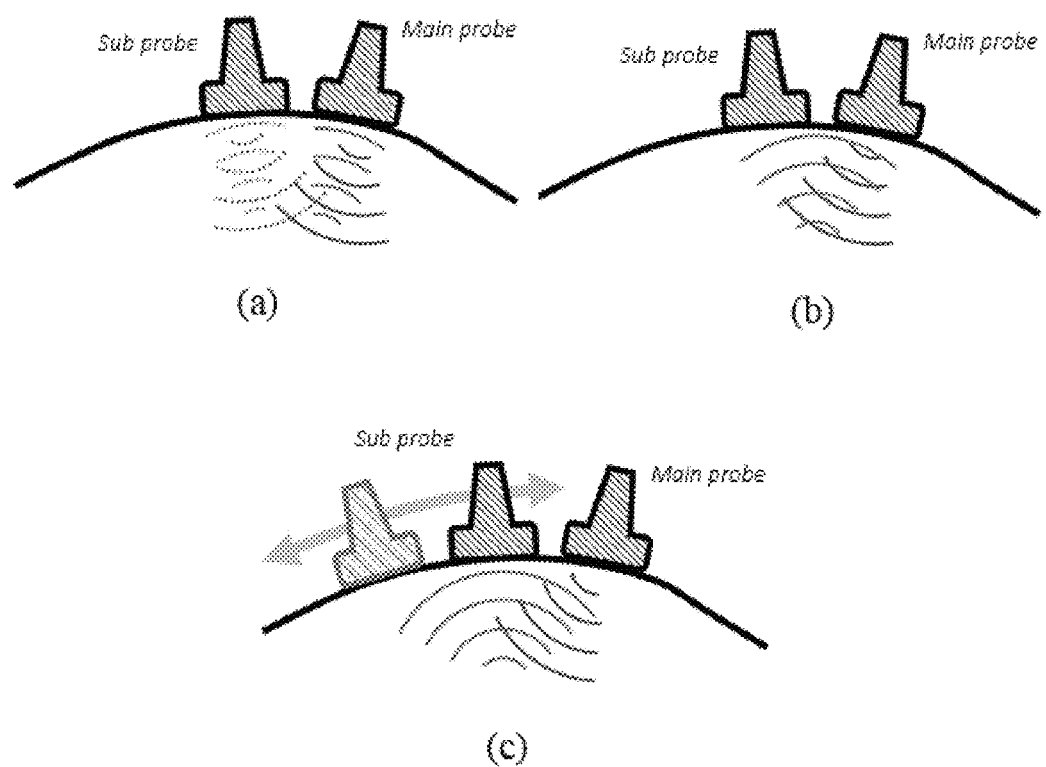
FIG. 33A shows synthetic tracked aperture imaging utilizing dual ultrasound probes, wherein transmit and receive are done in each probe independently.
FIG. 33B shows synthetic tracked aperture imaging utilizing dual ultrasound probes, wherein the transmission is from the main probe, and the reflected acoustic signals can be received by all probes.
FIG. 33C shows synthetic tracked aperture imaging utilizing dual ultrasound probes, wherein a receiving probe is swept.

For data acquisition, transmit and receive schemes can be arranged in different. As in single probe synthetic tracked aperture ultrasound imaging, transmit and receive can be done in each probe independently, and all data can be synthesized. This scheme is shown in FIG. 33A. In addition, transmit wave from the main probe can be received by both main and sub probes. In this case, the wider receive aperture can be kept, and the improvement of contract and signal-to-noise ratio can be expected. This scheme is shown in FIG. 33B. According to some embodiments of the invention, one of the probes can be swept to receive additional coherent signals. This scheme is shown in FIG. 33C.

Example 5—Synthetic Tracked Aperture Ultrasound Imaging Based on Fiducials Tracking The relative transformation between multiple poses is the information required to synthesize multiple sub-apertures. In previous sections, approaches based on an external tracker are introduced. However, in principle, the use of tracker is not mandatory as long as there is a way to know the relative transformation. Therefore, we describe herein fiducials tracking based synthetic tracked aperture ultrasound imaging. (FIG. 8). A three dimensional structure such as multiple points has its unique orientation and location, so the coordinate system of the structure can be used as a reference frame to know the relative transformation between multiple poses. For example, when point fiducials are used, the transformation between the ultrasound image frame and the fiducials frame A can be estimated through point cloud registration using the reference point location and segmented point location [1].

Figure 34A:
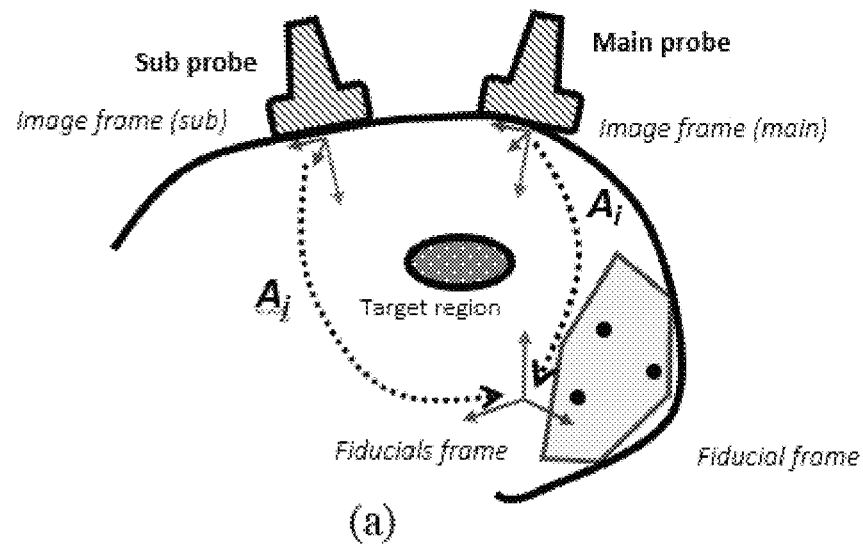
FIG. 34A illustrates synthetic tracked aperture imaging based on active fiducials tracking, wherein fiducial markers are attached outside of the body.
Figure 34B:
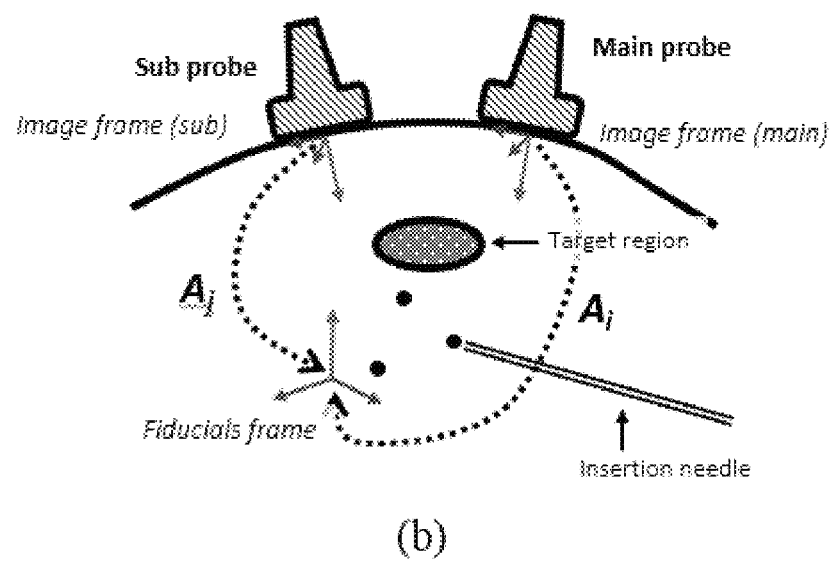
FIG. 34B illustrates synthetic tracked aperture imaging based on active fiducials tracking, wherein fiducial markers are inserted into the body.

The fiducials can be placed inside and outside of the patient's body. As an outside configuration, a patch with multiple active points can be attached to the patient, as illustrated in FIG. 34A. An ultrasound signal can be generated through a tiny piezo element or a photoacoustic effect can be generated using laser excitation. The locational relationships of point fiducials can be designed, and that will be used for the reference. While the location of the patch is fixed, the probe position can be moved, so that extended aperture through multiple poses can be generated. As an inside configuration, illustrated in FIG. 34B, the multiple contrast agents can be inserted interventionally. The reference fiducials location can be known by a pre-operative CT scan or a reconstructing 3D volume based on 3D ultrasound scanning. The rest of the process can be similar to the outside configuration.

Figure 35A:
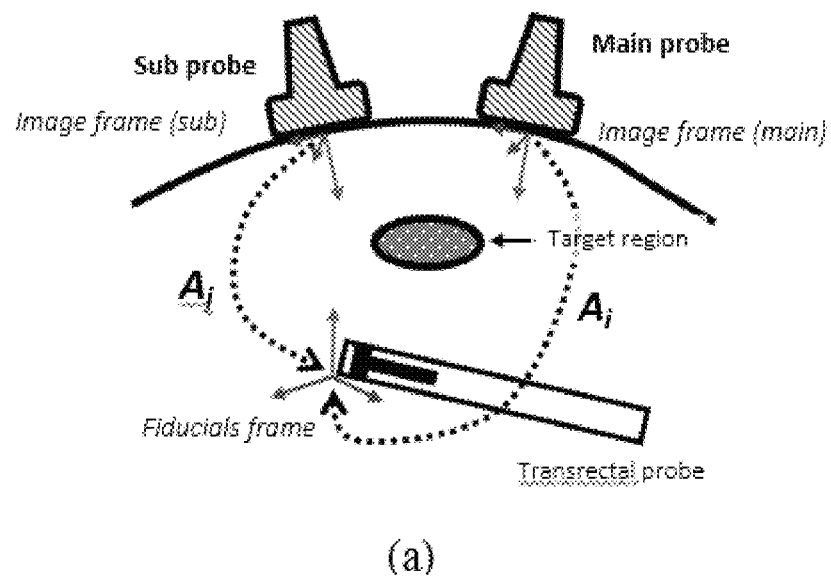
FIG. 35A shows synthetic tracked aperture imaging based on transrectal probe tracking, wherein two probes used and tracked for STrAtUS imaging.
Figure 35B:
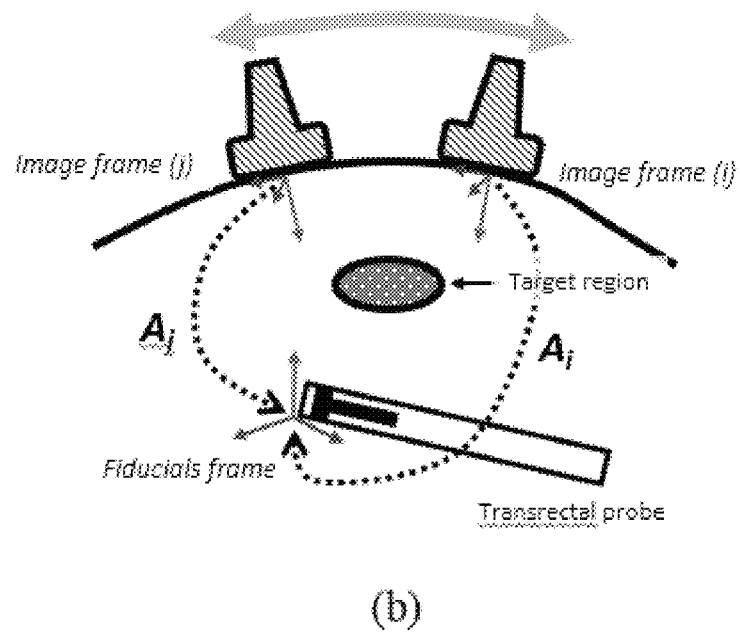
FIG. 35B shows synthetic tracked aperture imaging based on transrectal probe tracking, wherein a single probe is tracked while motion is provided.

Example 6—Synthetic Tracked Aperture Ultrasound Imaging Based on Transrectal Probe Tracking The basic idea is similar to synthetic tracked aperture ultrasound imaging based on fiducials tracking. Instead of placing fiducials, when a transrectal probe is used, it can be regarded as the multiple point fiducial markers. Tracking can be done by recovering the transformation between the ultrasound frame and the fiducial frame which is the transrectal probe's frame. We can use dual arm configuration, as shown in FIG. 35A, and can also move a single probe to construct synthetic tracked aperture imaging, as shown in FIG. 35B.

Example 7—Interventional Synthetic Tracked Aperture Imaging

Figures 36A, 36B, 36C:
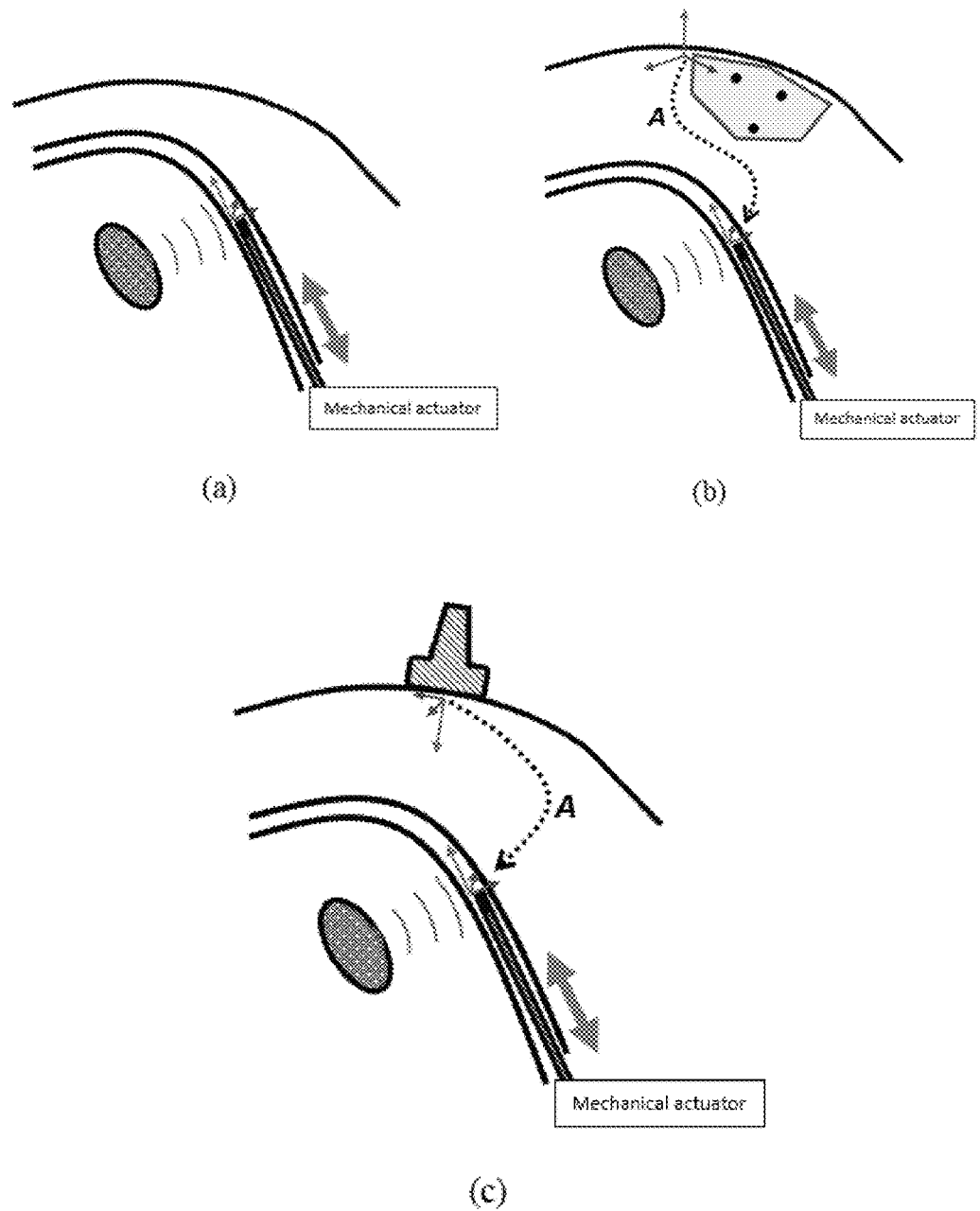
FIG. 36A illustrates interventional synthetic tracked aperture imaging, wherein the motion of a small ultrasound probe can be controlled through a mechanical actuator and signals can be processed using the synthetic aperture algorithm.
FIG. 36B illustrates interventional synthetic tracked aperture imaging, wherein an active fiducials structure can be used to track a small ultrasound probe externally.
FIG. 36C illustrates interventional synthetic tracked aperture imaging, wherein an ultrasound array transducer can also be used to track the small ultrasound probe.

Synthetic tracked aperture ultrasound imaging can not only be used outside of the body using an array transducer. Synthetic tracked aperture ultrasound imaging technique can also be used in interventional procedures. Since it may be difficult to form a large aperture size array, a transducer with a single element or a small number of elements can be tracked, and a synthesized image can be formed. The inserted small probe can be moved by motorized actuator, as shown in FIG. 36A. A synthetic aperture focusing algorithm can be used to beamform the received data at each pose [1]. When the motion from the mechanical actuator is stable, a relative transformation of multiple motion can be estimated from the input from the mechanical actuator. To more precisely know the accurate location of the ultrasound probe, piezo element fiducials phantom or ultrasound probe can be used, as illustrated in FIGS. 36B and 36C. The acoustic signal transmitted from interventional ultrasound probe can be received by external piezo element fiducials or an ultrasound probe, and the time-of-flight can be used to recover the relative transformation A through trilateration or multilateration. The opposite direction using the interventional ultrasound probe as a receiver can also be considered with the same algorithm.

Example 8—Synthetic Tracked Aperture Photoacoustic Imaging

Photoacoustic imaging is based on acoustic signals generated from laser excitation. The resolution of photoacoustic imaging is determined by both optical focusing and acoustic focusing, but when the region of interest is deep, only acoustic focusing is available due to optical scattering. In this sense, ultrasound receive beamforming strategy can be applied to photoacoustic imaging. The aperture size is a main factor determining the ultrasound image resolution, but it is limited by the size of the ultrasound receiver. A clinical ultrasound receiver can be used to receive photoacoustic data, and this configuration eases image registration between the photoacoustic image and the ultrasound image. When a clinical array ultrasound receiver is used, the size of the array limits the maximum achievable aperture size.

Figure 37:
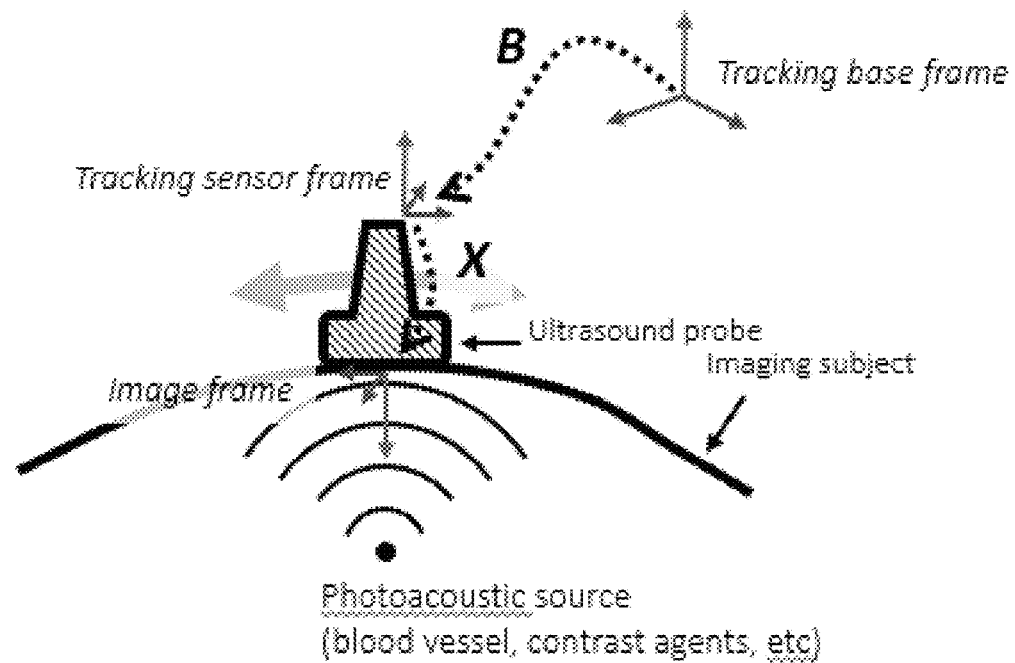
FIG. 37 shows synthetic tracked aperture photoacoustic imaging concepts and coordinate systems.

According to some embodiments of the invention, an array transducer is moved while its orientation and rotation are tracked. FIG. 37 illustrates the general concept and coordinate systems of synthetic tracked aperture photoacoustic imaging according to some embodiments of the invention. Photoacoustic data are received at each pose during a series of movements, and the data are regarded as sub-aperture information for synthetic aperture beamforming. Therefore, the final synthesized photoacoustic image has higher resolution compared to that of the single pose case.

Figure 38A:
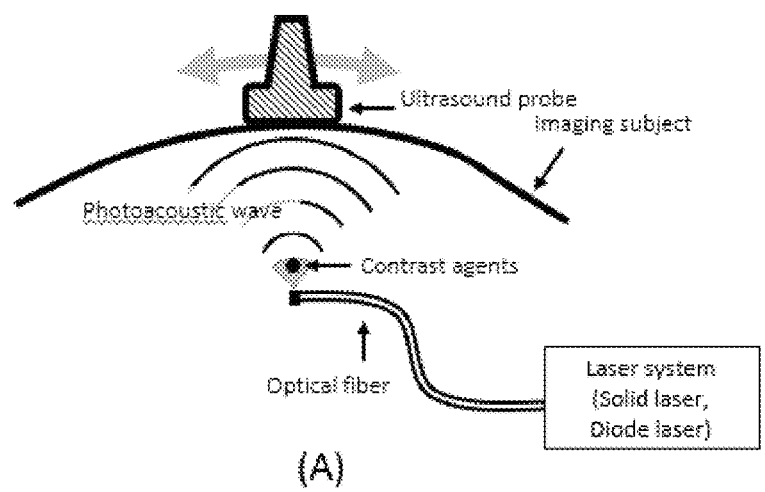
FIG. 38A illustrates synthetic tracked aperture photoacoustic imaging, wherein a laser source can be delivered internally to illuminate the contrast agents.
Figure 38B:
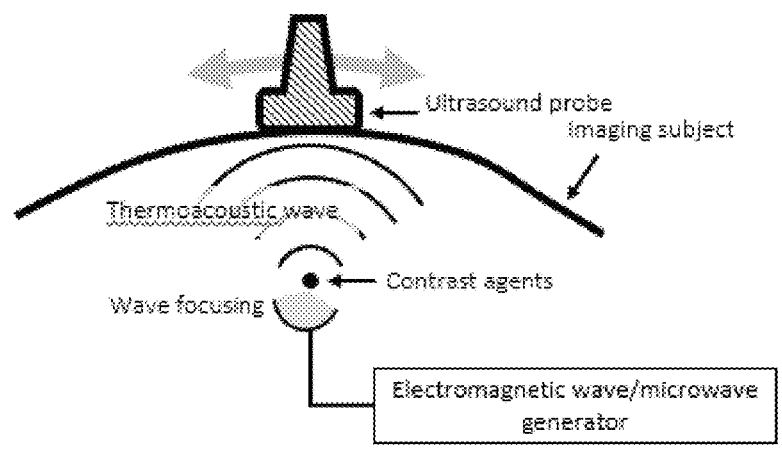
FIG. 38B illustrates synthetic tracked aperture photoacoustic imaging utilizing internal thermoacoustic source delivery.
Figure 38C:
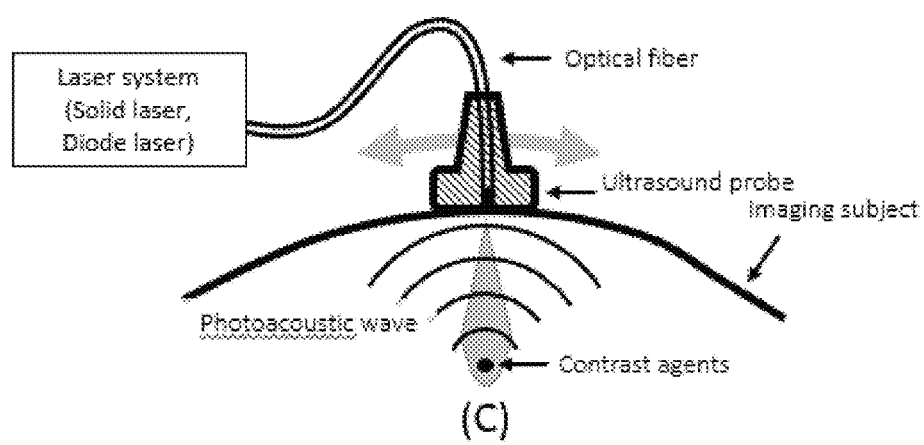
FIG. 38C illustrates synthetic tracked aperture photoacoustic imaging utilizing external photoacoustic source delivery.
Figure 38D:
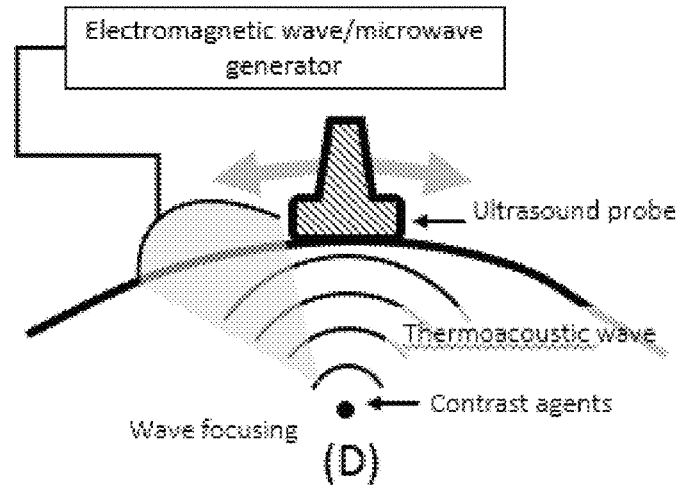
FIG. 38D illustrates synthetic tracked aperture photoacoustic imaging utilizing external thermoacoustic source delivery.
Figure 39A:
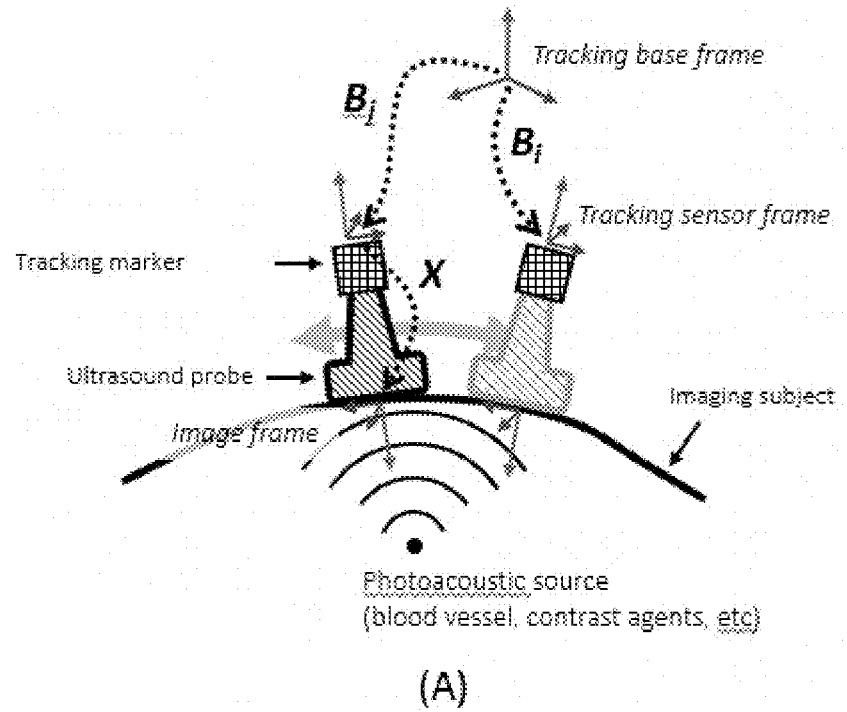
FIG. 39A shows synthetic tracked aperture photoacoustic imaging with an optical tracking system and a free hand configuration.
Figure 39B:
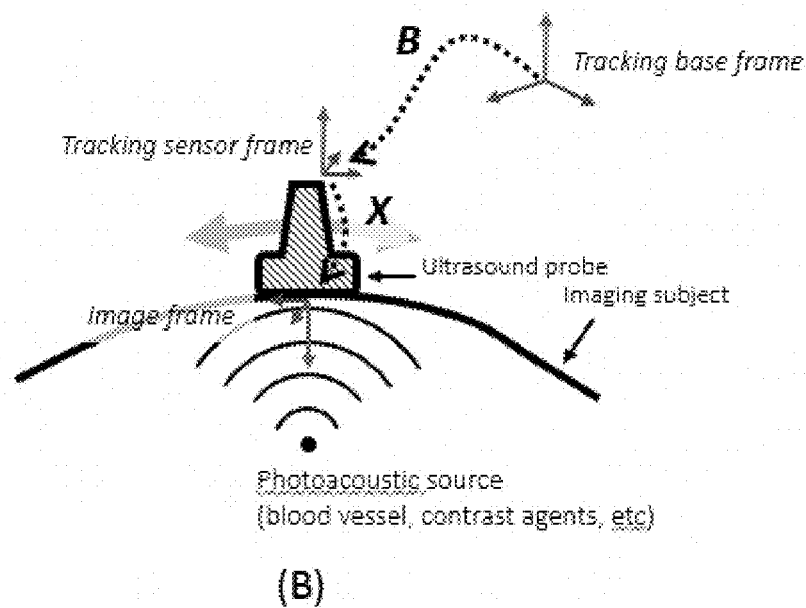
FIG. 39B shows synthetic tracked aperture photoacoustic imaging with robotic tracking and control.

The same tracking approaches used in synthetic tracked aperture ultrasound imaging can also be used for photoacoustic imaging. Similarly, the synthetic tracked aperture technique can be applied to thermoacoustic imaging which is based on electromagnetic/microwave emission. Various approaches for signals generation are shown in FIGS. 38A-38D. As shown in FIG. 38A, a laser source can be delivered internally to illuminate the contrast agents. FIG. 38B illustrates internal thermoacoustic source delivery. FIG. 38C shows external photoacoustic source delivery. FIG. 38D shows external thermoacoustic source delivery. FIGS. 39A and 39B show tracking systems for synthetic tracked aperture photoacoustic imaging according to some embodiments of the invention. FIG. 39A shows an optical tracking system and free hand configuration, and FIG. 39B shows robotic tracking and control.

Example 9—Multiple Active Points Phantom for Ultrasound Calibration

Ultrasound calibration is a process for determining the rigid-body transformation between the tracker sensor frame and the ultrasound image frame. Usually, a fiducial marker is imaged by the ultrasound probe from different angles and the corresponding pose orientations and positions of the tracked sensor are measured. These two data sets are used as the input to compute the unknown transformation. A single point can be used as the fiducial, or a line, several points, or more complicated calibration phantoms consisting of multiple points, lines, or planes. An extensive summary and comparison of different ultrasound calibration methods is provided in reference [1].

Figure 40:
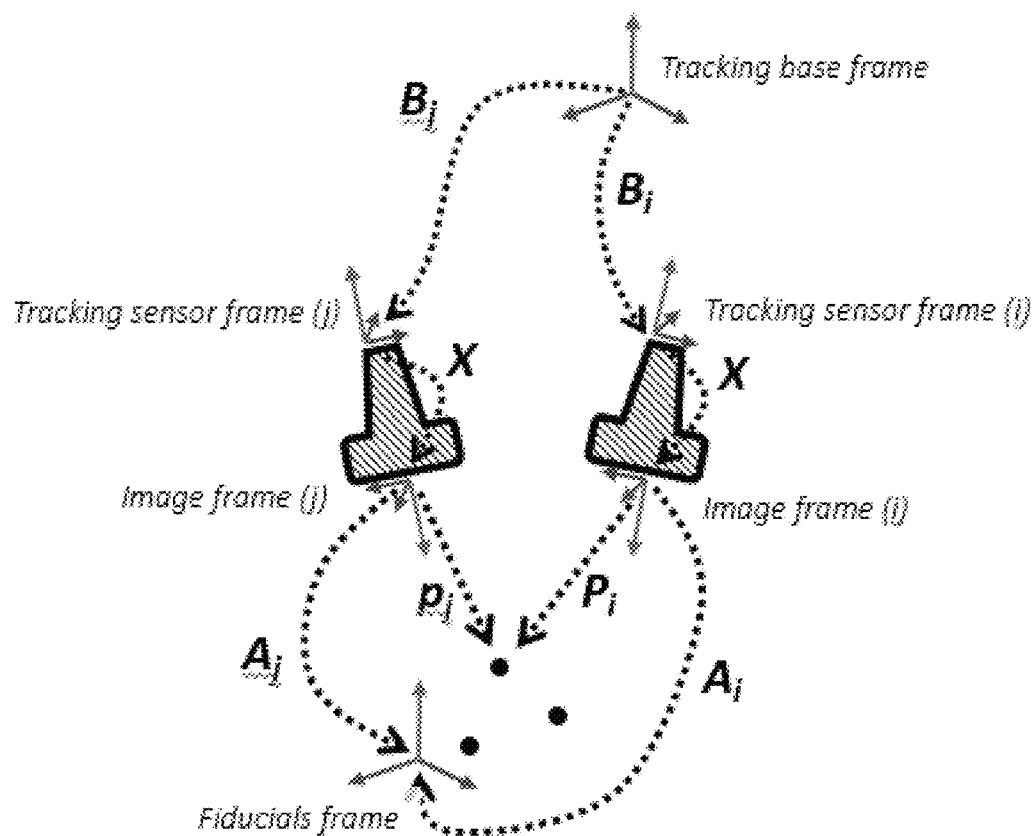
FIG. 40 shows the coordinate systems involved in ultrasound calibration using a multiple active point fiducials phantom.
Figure 41:
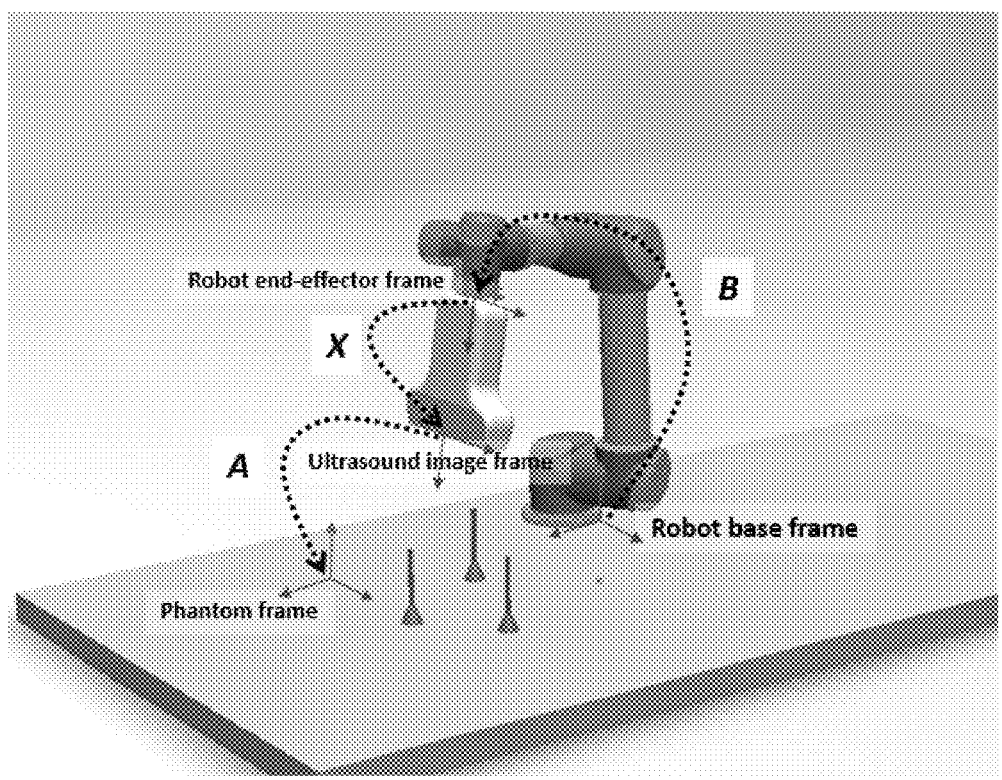
FIG. 41 shows a configuration of an active points phantom using a robot arm as a mechanical tracker.

According to some embodiments of the invention, an active phantom fabricated by a piezo element is used as the point fiducial. This active phantom transmits an ultrasound wave, and it is synchronized to ultrasound signal receiving. The design and implementation example of the phantom is shown in reference [2]. The problem of the previously proposed system is that it is difficult and time-consuming to align the mid-plane of the array probe to the phantom, which is necessary because otherwise error in the elevational direction will be induced in the computation. Here, a multiple active points phantom is proposed as a upgraded ultrasound calibration phantom. FIG. 40 illustrates the coordinate systems involved in ultrasound calibration using multiple active point fiducials phantom according to some embodiments of the invention. FIG. 41 shows a configuration of an active points phantom using a robot arm as a mechanical tracker. Since the geometrical relationship between the multiple point fiducials is known, the transformation between the phantom frame and ultrasound image frame can be estimated, and it is possible to recover three dimension locational information from segmented points in the ultrasound image. Therefore, it is not necessary to align the ultrasound pose to be in-plane with the point phantom, and a more accurate transformation can be estimated by minimizing the error in elevational direction. The time for the calibration procedure can also be shortened.

In addition, a multiple active point phantom is better than a single active point phantom in the algorithm point of view. In the single active point phantom case, a typical form of BXp US calibration is used [3-6]. In this equation p is the fiducial point in the sensor coordinate, B is the transformation measured by the tracking system, and X is the unknown desired homogeneous transformation. Since all $(B_i, B_j)$ pairs are measured for the same physical point, the relationship $B_i X p_i = B_j X p_j$ holds for all combinations of i and j. The limitation of the BXp formulation is that since only one locational component is known from a single point, it is not possible to fully obtain the rigid body transformation from the image frame to the phantom frame. However, in the case of a multiple active point phantom, since the relative positions of the multiple points is known, it is possible to recover the transformation A for each pose. This property indicates that the closed loop enables one to solve X through an AX=XB formulation [8], so that more rich information can be utilized for each pose.

REFERENCES

[1] K. Mustafa, P-C Li, M. O'Donnell, "Synthetic aperture imaging for small scale systems", IEEE Trans. Ultrason., Ferroelect., Freq. Cont., vol. 42, pp. 429-442, May 1995
[2] J. A. Jensen, S. I. Nikolov, K. L. Gammelmark, M. H. Pedersen, "Synthetic aperture ultrasound imaging", Ultrasonics, vol. 44, pp e5-e15, 2006
[3] G. E. Trahey, L. F. Nock, "Synthetic receive aperture imaging with phase correction for motion and for tissue inhomogeneities. II. Effects of and correction for motion", IEEE Trans. Ultrason., Ferroelect., Freq. Cont., vol. 39, pp. 496-501, 1992

References—Example 1

[1] Alexis Cheng et al., "Design and development of an ultrasound calibration phantom and system", Proc. SPIE Medical Imaging, 9036-76, 2014
[2] X. Guo, B. Tavakoli, H-J Kang, J. Kang, R. Etienne-Cummings, E. M. Boctor, "Photoacoustic Active Ultrasound Element for Catheter Tracking", Proc. SPIE Photonics West, BiOS, pp. 89435M, 2014
[3] Ackerman M. K., Cheng A., Boctor E., and Chirikjian G. S., "Online Ultrasound Sensor Calibration Using Gradient Descent on the Euclidean Group," Accepted to International Conference on Robotics and Automation, 2014.
[4] Treece G. M., Gee A. H., Prager R. W., Cash C. J. C., and Berman L. H., "High-definition freehand 3-D ultrasound", Ultrasound in Medicine and Biology, 29(4), pp. 529-546, 2003.

References—Example 2

[1] Holmes, J., Howry, D., Posakony G J, and Cushman, C., "The ultrasonic visualization of soft tissue structures in the human body," Transactions of the American Clinical and Climatological Association 66, 208-225 (1955).
[2] Weng, L., Tirumalai, A., and Lowery, C., "US extended-field-of-view imaging technology," Radiology 203(3), 877-880 (1997).
[3] Shattuck, D. and von Ramm, O., "Compound scanning with a phased array," Ultrasonic Imaging 4, 93-107 (1982).
[4] Corl, P., Grant, P., and Kino, G., "A Digital Synthetic Focus Acoustic Imaging System for NDE," 1978 Ultrasonics Symposium, 263-268 (1978).
[5] Walker, W. F. and Trahey, G. E., "The application of k-space in pulse echo ultrasound," IEEE Transactions on Ultrasonics, Ferroelectrics and Frequency Control 45(3), 541-558 (1998).
[6] Hansen, R. E., "Introduction to Synthetic Aperture Sonar," in [Sonar Systems], Kolev, P. N., ed., ch. 1, 3-29, InTech (2011).
[7] Karaman, M., Li, P.-C., and O'Donnell, M., "Synthetic Aperture Imaging for Small Scale Systems," IEEE Transactions on Ultrasonics, Ferroelectrics and Frequency Control 42(3), 429-442 (1995).

[8] Frazier, C. H. and O'Brien Jr., W. D., "Synthetic Aperture Techniques with a Virtual Source Element," IEEE Transactions on Ultrasonics, Ferroelectrics and Frequency Control 45(1), 196-207 (1998).

[9] Madsen, E. L., Zagzebski, J. A., Banjavic, R. A., and Burlew, M. M., "Phantom material and method," (1981).

[10] Jensen, J. A. and Svendsen, N. B., "Calculation of pressure fields from arbitrarily shaped, apodized, and excited ultrasound transducers," IEEE Transactions on Ultrasonics, Ferroelectrics, and Frequency Control 39(2), 262-267 (1992).

[11] Jensen, J. A., "Field: A Program for Simulating Ultrasound Systems," Medical & Biological Engineering & Computing 34 (Supplement 1, Part 1), pp. 351-353 (1996).

[12] Moshfeghi, M. and Waag, R., "In vivo and in vitro ultrasound beam distortion measurements of a large aperture and a conventional aperture focussed transducer," Ultrasound in Medicine & Biology 14(5), 415-428 (1988).

[13] Liu, D. D. and Waag, R. C., "Estimation and correction of ultrasonic wavefront distortion using pulse-echo data received in a two-dimensional aperture," IEEE transactions on ultrasonics, ferroelectrics, and frequency control 45(2), 473-90 (1998).

[14] Bottenus, N., Byram, B. C., and Trahey, G. E., "A synthetic aperture study of aperture size in the presence of noise and in vivo clutter," Proceedings of SPIE 8675, 1-10 (2013).

[15] Nock, L., Trahey, G. E., and Smith, S. W., "Phase aberration correction in medical ultrasound using speckle brightness as a quality factor," The Journal of the Acoustical Society of America 85(5), 1819-33 (1989).

[16] Kortbek, J., Jensen, J. A., and Gammelmark, K. L. k., "Sequential beamforming for synthetic aperture imaging," Ultrasonics 53(1), 1-16 (2013).

References—Example 3

[1] J. Holmes, D. Howry, Posakony G J, and C. Cushman, "The ultrasonic visualization of soft tissue structures in the human body," Transactions of the American Clinical and Climatological Association, vol. 66, pp. 208-225, 1955.

[2] L. Weng, A. Tirumalai, and C. Lowery, "US extended-field-of-view imaging technology." Radiology, vol. 203, no. 3, pp. 877-880, 1997.

[3] D. Shattuck and O. von Ramm, "Compound scanning with a phased array," Ultrasonic Imaging, vol. 4, pp. 93-107, 1982.

[4] G. R. Lockwood, J. R. Talman, and S. S. Brunke, "Real-time 3-D ultrasound imaging using sparse synthetic aperture beamforming." IEEE Transactions on Ultrasonics, Ferroelectrics and Frequency Control, vol. 45, no. 4, pp. 980-988, January 1998.

[5] J. Greenleaf, S. Johnson, S. Lee, and E. Woo, "Algebraic reconstruction of spatial distributions of acoustic absorption within tissue from their two-dimensional acoustic projections," Acoustical Holography, vol. 5, pp. 591-603, 1974.

[6] P. Corl, P. Grant, and G. Kino, "A Digital Synthetic Focus Acoustic Imaging System for NDE," 1978 Ultrasonics Symposium, pp. 263-268, 1978.

[7] M. Karaman, P.-C. Li, and M. O'Donnell, "Synthetic Aperture Imaging for Small Scale Systems," IEEE Transactions on Ultrasonics, Ferroelectrics and Frequency Control, vol. 42, no. 3, pp. 429-442, 1995.

[8] C. H. Frazier and W. D. O'Brien Jr., "Synthetic Aperture Techniques with a Virtual Source Element," IEEE Transactions on Ultrasonics, Ferroelectrics and Frequency Control, vol. 45, no. 1, pp. 196-207, 1998.

[9] W. F. Walker and G. E. Trahey, "The application of k-space in pulse echo ultrasound." IEEE Transactions on Ultrasonics, Ferroelectrics and Frequency Control, vol. 45, no. 3, pp. 541-558, January 1998.

[10] J. A. Johnson, M. Karaman, and B. T. Khuri-Yakub, "Coherent-array imaging using phased subarrays. Part I: basic principles." IEEE Transactions on Ultrasonics, Ferroelectrics and Frequency Control, vol. 52, no. 1, pp. 37-50, January 2005.

[11] S. Nikolov and J. Jensen, "Virtual ultrasound sources in high-resolution ultrasound imaging," Proceedings of SPIE, vol. 4687, pp. 395-405, 2002.

[12] H. Andresen, S. Nikolov, M. M. Pedersen, D. Buckton, and J. A. Jensen, "Three-dimensional synthetic aperture focusing using a rocking convex array transducer," IEEE Transactions on Ultrasonics Ferroelectrics and Frequency Control, vol. 57, no. 5, pp. 1051-1063, May 2010.

[13] S. Nikolov and J. Jensen, "Three-dimensional real-time synthetic aperture imaging using a rotating phased array transducer," 2002 IEEE Ultrasonics Symposium, pp. 1585-1588, 2002.

[14] H. Andresen, S. I. Nikolov, and J. A. Jensen, "Synthetic aperture focusing for a single-element transducer undergoing helical motion," IEEE Transactions on Ultrasonics Ferroelectrics and Frequency Control, vol. 58, no. 5, pp. 935-943, 2011.

[15] N. Bottenus, B. C. Byram, and G. E. Trahey, "A synthetic aperture study of aperture size in the presence of noise and in vivo clutter," Proceedings of SPIE, vol. 8675, pp. 1-10, March 2013.

[16] R. E. Hansen, "Introduction to Synthetic Aperture Sonar," in Sonar Systems, P. N. Kolev, Ed. InTech, 2011, ch. 1, pp. 3-29.

[17] J. Kortbek, J. A. Jensen, and K. L. Gammelmark, "Sequential beamforming for synthetic aperture imaging." Ultrasonics, vol. 53, no. 1, pp. 1-16, January 2013.

[18] J. A. Jensen and N. B. Svendsen, "Calculation of pressure fields from arbitrarily shaped, apodized, and excited ultrasound transducers," IEEE Transactions on Ultrasonics, Ferroelectrics, and Frequency Control, vol. 39, no. 2, pp. 262-267, 1992.

[19] J. A. Jensen, "Field: A Program for Simulating Ultrasound Systems," Medical & Biological Engineering & Computing, vol. 34, no. Supplement 1, Part 1, pp. 351-353, 1996.

[20] J. Hansen and J. Jensen, "Compounding in Synthetic Aperture Imaging," IEEE Transactions on Ultrasonics, Ferroelectrics, and Frequency Control, vol. 59, no. 9, pp. 2054-2065, 2012.

[21] K. Ustuner, M. Bolorforosh, and A. Gee, "Medical ultrasonic imaging with adaptive synthesis and compounding," U.S. Pat. No. 6,432,054, 2002.

[22] E. L. Madsen, J. A. Zagzebski, R. A. Banjavic, and M. M. Burlew, "Phantom material and method," 1981.

[23] D.-L. D. Liu and R. Waag, "Estimation and correction of ultrasonic wavefront distortion using pulse-echo data received in a two-dimensional aperture." IEEE Transactions on Ultrasonics, Ferroelectrics and Frequency Control, vol. 45, no. 2, pp. 473-90, January 1998.

[24] S. W. Smith, R. F. Wagner, J. M. F. Sandrik, and H. Lopez, "Low contrast detectability and contrast/detail analysis in medical ultrasound," IEEE Transactions on Sonics and Ultrasonics, vol. 3, no. 3, pp. 164-173, 1983.

[25] S. W. Flax and M. O'Donnell, "Phase-aberration correction using signals from point reflectors and diffuse scatterers: basic principles." IEEE Transactions on Ultrasonics, Ferroelectrics and Frequency Control, vol. 35, no. 6, pp. 758-67, January 1988.

[26] L. Nock, G. E. Trahey, and S. W. Smith, "Phase aberration correction in medical ultrasound using speckle brightness as a quality factor." The Journal of the Acoustical Society of America, vol. 85, no. 5, pp. 1819-1833, May 1989.

[27] M. Moshfeghi and R. Waag, "In vivo and in vitro ultrasound beam distortion measurements of a large aperture and a conventional aperture focussed transducer," Ultrasound in Medicine & Biology, vol. 14, no. 5, pp. 415-428, 1988.

[28] H. Durgin, P. Freiburger, D. Sullivan, and G. Trahey, "Large aperture phase error measurement and effects," 1992 Ultrasonics Symposium, pp. 623-628, 1992.

[29] D. Huang and J. Tsao, "Aperture size effect on ultrasonic wavefront distortion correction," IEEE Transactions on Ultrasonics, Ferroelectrics and Frequency Control, vol. 51, no. 5, 2004.

[30] E. J. Harris, N. R. Miller, J. C. Bamber, J. R. N. Symonds-Tayler, and P. M. Evans, "Speckle tracking in a phantom and feature-based tracking in liver in the presence of respiratory motion using 4D ultrasound." Physics in medicine and biology, vol. 55, no. 12, pp. 3363-3380, June 2010.

[31] K. Gammelmark and J. Jensen, "2-D tissue motion compensation of synthetic transmit aperture images," IEEE Transactions on Ultrasonics, Ferroelectrics and Frequency Control, vol. 61, no. 4, pp. 594-610, 2014.

References—Example 4

[1] F. Aalamifar, D. Jiang, H. K. Zhang, A Cheng, X Guo, R Khurana, I Iordachita, E. M. Boctor, "Co-robotic ultrasound tomography: dual arm setup and error analysis", SPIE Medical Imaging, 94190N-94190N-9

References—Example 5

[1] Mitra, Niloy J., et al. "Registration of point cloud data from a geometric optimization perspective." Proceedings of the 2004 Eurographics/ACM SIGGRAPH symposium on Geometry processing. ACM, 2004.

References—Example 7

[1] Stepinski, Tadeusz, and Fredrik Lingvall. "Synthetic aperture focusing techniques for ultrasonic imaging of solid objects." Synthetic Aperture Radar (EUSAR), 2010 8th European Conference on. VDE, 2010.

References—Example 9

[1] Mercier, L., et. al., "A review of calibration techniques for freehand 3-D ultrasound systems." Ultrasound in medicine & biology 31, no. 2, 143-165 (2005).

[2] X. Guo, A. Cheng, H. K. Zhang, H. Kang, R. Etienne-Cummings, E. M. Boctor, "Active echo: a new paradigm for ultrasound calibration," Medical Imaging Computing & Computer Assisted Interventions Conference (2014).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A synthetic aperture ultrasound system, comprising:
an ultrasound probe;
an ultrasound signal processor configured to communicate with the ultrasound probe to receive both phase and amplitude information from channel data or beamformed radio-frequency signals from a corresponding plurality of transmitted ultrasound pulses,
the ultrasound signal processor to determine a trajectory based upon scanning a plurality of poses; and
a tracker configured to:
detect movement of the ultrasound probe into the plurality of poses,
determine a first position of the ultrasound probe and a second position of the ultrasound probe,
the first position being associated with a first pose of the plurality of poses,
the second position being associated with a second pose of the plurality of poses,
the second position of the ultrasound probe being translated with respect to the first position of the ultrasound probe,
provide, to the ultrasound signal processor, the first position associated with the first pose of the plurality of poses and the second position associated with the second pose of the plurality of poses,
wherein the ultrasound signal processor is further configured to:
select the first pose of the plurality of poses associated with the first position and the second pose of the plurality of poses associated with the second position,
the first pose of the plurality of poses and the second pose of the plurality of poses being selected based on matching a reconstruction geometry of the trajectory, and
beamform the channel data or the beamformed radio-frequency signals, utilizing probe position information, where at least one of the channel data or beamformed radio-frequency signals while the ultrasound probe is in the first position with at least one of the channel data or beamformed radio-frequency signals while the ultrasound probe is in the second position to provide a synthetic aperture that is larger than a physical aperture of the ultrasound probe.

2. The synthetic aperture ultrasound system according to claim 1, wherein the probe position information has an accuracy in an axial direction towards a region of interest that is at least one-half a wavelength of ultrasound waves of the plurality of transmitted ultrasound pulses.

3. The synthetic aperture ultrasound system according to claim 1, wherein the ultrasound probe is a hand-operable ultrasound probe.

4. The synthetic aperture ultrasound system according to claim 1, wherein the tracker is a robotic system comprising a robotic arm attached to the ultrasound probe.

5. The synthetic aperture ultrasound system according to claim 4, wherein the probe position information is obtained from the robotic system.

6. The synthetic aperture ultrasound system according to claim 4, wherein the robotic system is configured to perform a pre-programmed sweep of the ultrasound probe.

7. The synthetic aperture ultrasound system according to claim 4, wherein the robotic system is configured to perform an adaptive sweep of the ultrasound probe based on the phase and amplitude information received by the ultrasound signal processor.

8. The synthetic aperture ultrasound system according to claim 1, wherein the ultrasound signal processor is configured to receive an indication when a velocity of the ultrasound probe is within a pre-determined range for synthetic aperture imaging, and
wherein the ultrasound signal processor is further configured to enter a synthetic aperture imaging mode upon receipt of the indication.

9. The synthetic aperture ultrasound system according to claim 1, wherein the ultrasound probe comprises a two-dimensional array.

10. The synthetic aperture ultrasound system according to claim 1, wherein the ultrasound probe is a photoacoustic ultrasound probe, and
wherein the ultrasound signal processor is configured to communicate with the photoacoustic ultrasound probe to receive both phase and amplitude information from a plurality of photoacoustic ultrasonic echo signals from a corresponding plurality of transmitted photoacoustic ultrasound pulses.

11. The synthetic aperture ultrasound system according to claim 1, wherein the first position of the ultrasound probe and the second position of the ultrasound probe are at a same distance from a region of interest, and
wherein the ultrasound probe is rotated to face the region of interest.

12. The synthetic aperture ultrasound system according to claim 1, further comprising:
a display system, and
a user interface,
wherein a user is able to select a region of interest on the display system using the user interface.

13. The synthetic aperture ultrasound system according to claim 1, further comprising:
a second ultrasound probe,
wherein the ultrasound probe is configured to receive ultrasonic echo signals from a corresponding plurality of ultrasound pulses transmitted by the second ultrasound probe.

14. A method for providing a synthetic aperture that is larger than a physical aperture of an ultrasound probe, comprising:
transmitting, by one or more devices, a plurality of ultrasound pulses;
receiving, by the one or more devices, both phase and amplitude information from channel data or beamformed radio-frequency signals corresponding to the plurality of ultrasound pulses;
determining, by the one or more devices, a trajectory based upon scanning a plurality of poses;
detecting, by the one or more devices, movement of the ultrasound probe into the plurality of poses;
determining, by the one or more devices a first transmission and reception position relative to a region of interest and a second transmission and reception position relative to the region of interest,
the first transmission and reception position being associated with a first pose of the plurality of poses,
the second transmission and reception position being associated with a second pose of the plurality of poses,
the second transmission and reception position being translated with respect to the first transmission and reception position;
providing, by the one or more devices, the first transmission and reception position associated with the first pose of the plurality of poses and the second transmission and reception position being associated with the second pose of the plurality of poses;
selecting, by the one or more devices, the first pose of the plurality of poses associated with the first transmission and reception position and the second pose of the plurality of poses associated with the second transmission and reception position,
the first pose of the plurality of poses and the second pose of the plurality of poses being selected based on matching a reconstruction geometry of the trajectory, and
beamforming, by the one or more devices, the channel data or the beamformed radio-frequency signals, utilizing position information, where at least one of said the channel data or the beamformed radio-frequency signals, received at the first transmission and reception position with at least one of said the channel data or the beamformed radio-frequency signals, received at second transmission and reception position to provide the synthetic aperture.

15. The method of claim 14, further comprising:
receiving an indication that a velocity of the ultrasound probe is within a pre-determined range for synthetic aperture imaging, and
entering a synthetic aperture imaging mode upon receiving the indication.

16. The synthetic aperture ultrasound system according to claim 1, wherein the tracker is at least one of:
a jointed mechanical arm;
an electromagnetic tracker, or
an optical positioning system.

17. A system, comprising:
an ultrasound probe;
a robotic arm attached to the ultrasound probe,
the robotic arm to move the ultrasound probe into a plurality of poses;
the robotic arm to determine probe position information associated with the plurality of poses; and
an ultrasound signal processor configured to:
receive, from the ultrasound probe, phase and amplitude information from channel data or beamformed radio-frequency signals associated with a plurality of transmitted ultrasound pulses;
receive, from the robotic arm, an initial position associated with the ultrasound probe;
determine a trajectory based upon scanning a plurality of poses; and
receive, from the robotic arm, information associated with a first position of the ultrasound probe and a second position of the ultrasound probe,
the first position being associated with a first pose of the plurality of poses,
the second position being associated with a second pose of the plurality of poses,
the second position of the ultrasound probe being translated with respect to the first position of the ultrasound probe;

select the first pose of the plurality of poses associated with the first position and the second pose of the plurality of poses associated with the second position,
the first pose of the plurality of poses and the second pose of the plurality of poses being selected based on matching a reconstruction geometry of the trajectory, and
beamform the channel data or the beamformed radio-frequency signals using probe position information, at least one of the channel data or the beamformed radio-frequency signals while the ultrasound probe is in the first position, and at least one of the channel data or the beamformed radio-frequency signals while the ultrasound probe is in the second position to provide a synthetic aperture that is larger than a physical aperture of the ultrasound probe.

18. The system of claim 17, wherein the robotic arm is configured to perform an adaptive sweep of the ultrasound probe based on the phase and amplitude information received by the ultrasound signal processor.

19. The system of claim 17, wherein the robotic arm is configured to perform a pre-programmed sweep of the ultrasound probe.

20. The system of claim 17, wherein the ultrasound signal processor is configured to receive an indication when a velocity of the ultrasound probe is within a pre-determined range for synthetic aperture imaging, and
wherein the ultrasound signal processor is further configured to enter a synthetic aperture imaging mode upon receipt of the indication.

* * * * *